US009970059B2

(12) United States Patent
Rimsza et al.

(10) Patent No.: US 9,970,059 B2
(45) Date of Patent: May 15, 2018

(54) SURVIVAL PREDICTOR FOR DIFFUSE LARGE B CELL LYMPHOMA

(71) Applicants: The United States of America, as represented by the Secretary, Department of Health and Human Services, Washington, DC (US); Arizona Board of Regents on behalf of the University of Arizona, Tucson, AZ (US); Queen Mary University of London, London (GB); Board of Regents of the University of Nebraska, Lincoln, NE (US); Oslo University Hospital HF, Oslo (NO); Oregon Health & Science University, Portland, OR (US); University of Rochester, Rochester, NY (US); Hospital Clinic de Barcelona, Barcelona (ES); Universitat De Barcelona, Barcelona (ES); British Columbia Cancer Agency Branch, Vancouver (CA); Julius-Maximilians-University of Wuerzburg, Wuerzburg (DE)

(72) Inventors: Lisa Rimsza, Tucson, AZ (US); Andrew T. Lister, London (GB); Wing C. Chan, Omaha, NE (US); Dennis Weisenburger, Elkhorn, NE (US); Jan Delabie, Oslo (NO); Erlend B. Smeland, Oslo (NO); Harald Holte, Oslo (NO); Stein Kvaloy, Oslo (NO); Rita M. Braziel, West Linn, OR (US); Richard I. Fisher, Pittsford, NY (US); Pedro Jares, Barcelona (ES); Armando Lopez-Guillermo, Barcelona (ES); Elias Campo Guerri, Barcelona (ES); Elaine S. Jaffe, Great Falls, VA (US); Georg Lenz, Berlin (DE); Wyndham H. Wilson, Washington, DC (US); George Wright, Rockville, MD (US); Sandeep S. Dave, Chapel Hill, NC (US); Louis M. Staudt, Bethesda, MD (US); Randy D. Gascoyne, North Vancouver (CA); Joseph M. Connors, Vancouver (CA); Hans-Konrad Muller-Hermelink, Wrzburg (DE); Andreas Rosenwald, Wuerzburg (DE); German Ott, Bietigheim-Bissingen (DE)

(73) Assignees: The United States of America, as represented by the Secretary, Department of Human Services, Washington, DC (US); Arizona Board of Regents on behalf of the University of Arizona, Tucson, AZ (US); Queen Mary University of London, London (GB); Board of Regents of the University of Nebraska, Lincoln, NE (US); Oslo University Hospital HF, Oslo (NO); Oregon Health & Science University, Portland, OR (US); University of Rochester, Rochester, NY (US); Hospital Clinic de Barcelona, Barcelona (ES); Universitat de Barcelona, Barcelona (ES); British Columbia Cancer Agency Branch, Vancouver (CA); Julius-Maximilians-University of Würzburg, Würzburg (DE)

( * ) Notice: Subject to any disclaimer, the term of this patent is extended or adjusted under 35 U.S.C. 154(b) by 588 days.

(21) Appl. No.: 14/540,302

(22) Filed: Nov. 13, 2014

(65) Prior Publication Data

US 2015/0132297 A1    May 14, 2015

Related U.S. Application Data

(63) Continuation of application No. 12/996,489, filed as application No. PCT/US2009/046421 on Jun. 5, 2009, now abandoned.

(Continued)

(51) Int. Cl.
*C12Q 1/68* (2018.01)
*G01N 33/574* (2006.01)

(52) U.S. Cl.
CPC ..... *C12Q 1/6886* (2013.01); *G01N 33/57407* (2013.01); *C12Q 2600/106* (2013.01);
(Continued)

(58) Field of Classification Search
None
See application file for complete search history.

(56) References Cited

U.S. PATENT DOCUMENTS

| 5,445,934 A | 8/1995 | Fodor et al. |
| 5,744,305 A | 4/1998 | Fodor et al. |

(Continued)

FOREIGN PATENT DOCUMENTS

| WO | WO 02/24956 A2 | 3/2002 |
| WO | WO 03/021229 A2 | 3/2003 |

(Continued)

OTHER PUBLICATIONS

Ganjoo, "Antiangiogenesis: A new approach to the treatment of lymphoma," (Leukemia and Lymphoma, vol. 48 (2007) pp. 454-455).*

(Continued)

*Primary Examiner* — Anna Skibinsky
(74) *Attorney, Agent, or Firm* — Leydig, Voit & Mayer, Ltd.

(57) ABSTRACT

The invention provides methods and materials related to a gene expression-based survival predictor for DLBCL patients.

16 Claims, 22 Drawing Sheets

Related U.S. Application Data

(60) Provisional application No. 61/059,678, filed on Jun. 6, 2008.

(52) U.S. Cl.
CPC .... *C12Q 2600/112* (2013.01); *G01N 2800/52* (2013.01); *G01N 2800/56* (2013.01)

(56) References Cited

U.S. PATENT DOCUMENTS

| | | | |
|---|---|---|---|
| 6,020,198 | A | 2/2000 | Bennett et al. |
| 6,410,229 | B1 | 6/2002 | Lockhart et al. |
| 7,711,492 | B2 | 5/2010 | Staudt et al. |
| 2002/0110820 | A1 | 8/2002 | Ramaswamy et al. |
| 2003/0194701 | A1 | 10/2003 | Golub et al. |
| 2003/0219760 | A1 | 11/2003 | Gordon et al. |
| 2005/0164231 | A1 | 7/2005 | Staudt et al. |
| 2008/0051379 | A1* | 2/2008 | Lerner ............ A61K 31/56 514/171 |
| 2008/0138336 | A1* | 6/2008 | Damschroder .... C07K 16/2803 424/133.1 |
| 2009/0023149 | A1* | 1/2009 | Knudsen ............ C12Q 1/6886 435/6.14 |

FOREIGN PATENT DOCUMENTS

| WO | WO 03/024956 A1 | 3/2003 |
|---|---|---|
| WO | WO 2005/024043 A2 | 3/2005 |

OTHER PUBLICATIONS

U.S. Appl. No. 12/996,489, filed Feb. 24, 2011.
U.S. Appl. No. 60/500,537, filed Sep. 3, 2003, Staudt et al.
Alizadeh et al., "Distinct Types of Diffuse Large B-Cell Lymphoma Identified by Gene Expression Profiling," *Nature*, 403, 503-511 (2000).
Alon et al., "Broad Patterns of Gene Expression Revealed by Clustering Analysis of Tumor and Normal Colon Tissues Probed by Oligonucleotide Arrays," *Proc. Nat'l. Acad. Sci. USA*, 96, 6745-6750 (1999).
Andreasson et al., "Genomic Amplification of CCND2 is Rare in Non-Hodgkin Lymphomas," *Cancer Genet. Cytogenet.*, 102, 81-82 (1998).
Basso et al., "Tracking CD40 Signaling During Germinal Center Development," *Blood*, 104 (13), 4088-4096 (2004).
Bea et al., "Diffuse Large B-Cell Lymphoma Subgroups Have Distinct Genetic Profiles That Influence Tumor Biology and Improve Gene-Expression-Based Survival Prediction," *Blood*, 106 (9), 3183-3190 (2005).
Bea et al., "Increased Number of Chromosomal Imbalances and High-Level DNA Amplifications in Mantle Cell Lymphoma Are Associated With Blastoid Variants," *Blood*, 93 (12), 4365-4374 (1999).
Bea et al., "Clinicopathologic Significance and Prognostic Value of Chromosomal Imbalances in Diffuse Large B-Cell Lymphomas," *J. Clin. Oncol.*, 22 (17), 3498-3506 (2004).
Berglund et al., "Chromosomal Imbalances in Diffuse Large B-Cell Lymphoma Detected by Comparative Genomic Hybridization," *Mod. Pathol.*, 15 (8), 807-817 (2002).
Bergsagel et al., "Critical Roles for Immunoglobulin Translocations and Cyclin D Dysregulation in Multiple Myeloma," *Immunol. Rev.*, 194, 96-104 (2003).
Bishop et al., "Burkitt's Lymphoma: Molecular Pathogenesis and Treatment," *Cancer Invest.*, 18 (6), 574-583 (2000).
Boxer et al., "Translocations Involving c-myc and c-myc Function," Oncogene, 20, 5595-5610 (2001).
Chiarle et al., "Increased Proteasome Degradation of Cyclin-Dependent Kinase Inhibitor p27 is Associated with a Decreased Overall Survival in Mantle Cell Lymphoma," *Blood*, 95, 619-626 (2000).
Cho et al., "A Genome-Wide Transcriptional Analysis of the Mitotic Cell Cycle," *Mol. Cell.*, 2, 65-73 (1998).
Chu et al., "The Transcriptional Program of Sporulation in Budding Yeast," *Science*, 282, 699-705 (1998).
Cigudosa et al., "Cytogenetic Analysis of 363 Consecutively Ascertained Diffuse Large B-Cell Lymphomas," *Genes Chromosomes Cancer*, 25, 123-133 (1999).
Coiffier et al., "Chop Chemotherapy Plus Rituximab Compared with Chop Alone in Elderly Patients with Diffuse Large B-Cell Lymphoma," *N. Engl. J. Med.*, 346 (4), 235-242 (2002).
Dave et al., "Cytogentic Characterization of Diffuse Large Cell Lymphoma Using Multi-Color Fluorescence In Situ Hybridization," *Cancer Genet. Cytogenet.*, 132, 125-132 (2002).
Dave et al., "Molecular Diagnosis of Burkitt's Lymphoma," *N. England J. Med.*, 354 (23), 2431-2442 (2006).
Davis et al., "Molecular Diagnosis of Lymphoid Malignancies by Gene Expression Profiling," *Curr. Opin. Hematol.*, 9, 333-338 (2002).
Davis et al., "Constitutive Nuclear Factor kB Activity is Required for Survival of Activated B Cell-like Diffuse Large B Cell Lymphoma Cells," *J. Exp. Med.*, 194 (12),1861-1874 (2001).
Delmer et al., "Overexpression of Cyclin D2 Chronic B-Cell Malignancies," *Blood*, 85 (10), 2870-2876 (1995).
Derisi et al., "Exploring the Metabolic and Genetic Control of Gene Expression on a Genomic Scale," *Science*, 278, 680-686 (1997).
Doglioni et al., "Cyclin D2 Expression in Normal, Reactive and Neoplastic Tissues," *J. Pathol.*, 185, 159-166 (1998).
Eisen et al., "Cluster Analysis and Display of Genome-wide Expression Patterns," *Proc. Nat'l. Acad. Sci. USA*, 95, 14863-14868 (1998).
European Search Report, Application No. 09170243.1, dated Jun. 24, 2010.
Feuerhake et al., "NFκB Activity, Function, and Target-Gene Signatures in Primary Mediastinal Large B-cell Lymphoma and Diffuse Large B-cell Lymphoma Subtypes," *Blood*, 106 (4), 1392-1399 (2005).
Fu et al., "Cyclin D1-negative Mantle Cell Lymphoma: a Clinicopathologic Study Based on Gene Expression Profiling," *Blood*, 106 (13), 4315-4321 (2005).
Gerbitz et al., "Deregulation of the Proto-oncogene c-myc through t(8;22) Translocation in Burkitt's Lymphoma," *Oncogene*, 18, 1745-1753 (1999).
Goff et al., "The Use of Real-time Quantitative Polymerase Chain Reaction and Comparative Genomic Hybridization to Identify Amplification of the REL gene in Follicular Lymphoma," *Br. J. Haematol.*, 111, 618-625 (2000).
Gress et al., "A Pancreatic Cancer-specific Expression Profile," *Oncogene*, 13, 1819-1830 (1996).
Haralambieva et al., "Clinical, Immunophenotypic, and Genetic Analysis of Adult Lymphomas with Morphologic Features of Burkitt Lymphoma," *Am. J. Surg. Pathol.*, 29 (8), 1086-1094 (2005).
Holstege et al., "Dissecting the Regulatory Circuitry of a Eukaryotic Genome," *Cell.*, 95, 717-728 (1998).
Huang et al., "The t(14;18) Defines a Unique Subset of Diffuse Large B-cell Lymphoma with a Germinal Center B-cell Gene Expression Profile," *Blood*, 99, 2285-2290 (2002).
Hummel et al., "A Biologic Definition of Burkitt's Lymphoma from Transcriptional and Genomic Profiling," *N. Engl. J. Med.*, 354 (23), 2419-2430 (2006).
Hyman et al., "Impact of DNA Amplification on Gene Expression Patterns in Breast Cancer," *Cancer Res.*, 62, 6240-6245 (2002).
Iqbal et al., "BCL2 Translocation Defines a Unique Tumor Subset within the Germinal Center B-Cell-Like Diffuse Large B-Cell Lymphoma," *Am. J. Pathol.*, 165 (1), 159-166 (2004).
International Search Report, Application No. PCT/US2007/016843, dated Oct. 30, 2008.
International Search Report, Application No. PCT/US04/29041, dated Aug. 26, 2005.
Jares et al., "Expression of Retinoblastoma Gene Product (pRb) in Mantle Cell Lymphomas—Correlation with Cyclin D1 (PRAD1/CCND1) mRNA Levels and Proliferative Activity," *Am. J. Pathol.*, 148 (5), 1591-1600 (1996).

(56) References Cited

OTHER PUBLICATIONS

Kramer et al., "Clinical Relevance of BCL2, BCL6, and MYC Rearrangements in Diffuse Large B-Cell Lymphoma," *Blood*, 92 (9), 3152-3162 (1998).
Lenz et al., "Stromal Gene Signatures in Large-B-Cell Lymphomas," *N. Engl. J. Med.*, 359 (22), 2313-2323 (2008) (with supplementary material).
Lenz et al., "Oncogenic CARD11 Mutations in Human Diffuse Large B Cell Lymphoma," *Science*, 319, 1676-1679 (2008).
Li, "Survival Prediction of Diffuse Large B-cell Lymphoma Based on Both Clinical and Gene Expression Information," *Bioinformatics*, 22 (4), 466-471 (2006).
Mahadevan et al., "Transcript Profiling in Peripheral T-cell Lymphoma, not Otherwise Specified, and Diffuse Large B-cell Lymphoma Identifies Distinct Tumor Profile Signatures," *Mol. Cancer Ther.*, 4 (12), 1867-1879 (2005).
Monni et al., "DNA Copy Number Changes in Diffuse Large B-Cell Lymphoma—Comparative Genomic Hybridization Study," *Blood*, 87 (12), 5269-5278 (1996).
Monti et al., "Molecular Profiling of Diffuse Large B-cell Lymphoma Identifies Robust Subtypes Including One Characterized by Host Inflammatory Response," *Blood*, 105,1851-1861(2005).
Mounier et al., "Rituximab Plus CHOP (R-CHOP) Overcomes bcl-2-associated Resistance to Chemotherapy in Elderly Patients with Diffuse Large B-cell Lymphoma (DLBCL)," *Blood*, 101, 4279-4284 (2003).
Neri et al., "Different Regions of the Immunoglobulin Heavy-Chain Locus are Involved in Chromosomal Translocations in Distinct Pathogenetic Forms of Burkitt Lymphoma," *Proc. Natl. Acad. Sci. USA*, 85, 2748-2752 (1988).
Ngo et al., "A Loss-of-function RNA Interference Screen for Molecular Targets in Cancer," *Nature*, 441, 106-110 (2006).
Nyman et al., "Prognostic Impact of Immunohistochemically Defined Germinal Center Phenotype in Diffuse Large B-cell Lymphoma Patients Treated with Immunochemotherapy," *Blood*, 109, 4930-4935 (2007).
Orsetti et al., "Genomic and Expression Profiling of Chromosome 17 in Breast Cancer Reveals Complex Patterns of Alterations and Novel Candidate Genes," *Cancer Res.*, 64, 6453-6460 (2004).
Ott et al., "Cyclin D1 Expressions in Mantle Cell Lymphoma is Accompanied by Downregulation of Cyclin D3 and is not Related to the Proliferative Activity," *Blood*, 90 (8), 3154-3159 (1997).
Pruneri et al., "Immunoreactivity for Cyclin D3 is Frequently Detectable in High-grade Primary Gastric Lymphomas in the Absence of the t(6;14)(p21.1;q32.3) Chromosomal Translocation," *J. Pathol.*, 200, 596-601 (2003).
Quintanilla-Martinez et al., "Mantle Cell Lymphomas Lack Expression of $p27^{klp1}$, a Cyclin-Dependent Kinase Inhibitor," *Am. J. Pathol.*, 153 (1), 175-182 (1998).
Ransohoff, "Rules of Evidence for Cancer Molecular-Marker Discovery and Validation," *Nat. Rev. Cancer*, 4, 309-314 (2004).
Rao et al., "Chromosomal and Gene Amplification in Diffuse Large B-Cell Lymphoma," *Blood*, 92 (1), 234-240 (1998).
Rimsza et al., "Loss of MHC Class II Gene and Protein Expression in Diffuse Large B-cell Lymphoma is Related to Decreased Tumor Immunosurveillance and Poor Patient Survival Regardless of Other Prognostic Factors: a Follow-Up Study from the Leukemia and Lymphoma Molecular Profiling Project," *Blood*, 103, 4251-4258 (2004).
Rogge et al., "Gene Profiling of Lymphoma, Myeloma, and AML," *Medscape from WebMed*, 5 (3), 1-8 (2003).
Rosenwald et al., "Molecular Diagnosis of Primary Mediastinal B Cell Lymphoma Identifies a Clinically Favorable Subgroup of Diffuse Large B Cell Lymphoma Related to Hodgkin Lymphoma," *J. Exp. Med.*, 198 (6), 851-862 (2003).
Rosenwald et al., "The Use of Molecular Profiling to Predict Survival after Chemotherpy for Diffuse Large B-Cell Lymphoma," *New Eng. J. Med.*, 346 (25),1937-1947 (2002).
Rosenwald, et al., "The Proliferation Gene Expression Signature is a Quantitative Integrator of Oncogenic Events that Predicts Survival in Mantle Cell Lymphoma," *Cancer Cell*, 3,185-197 (2003.
Savage et al., "The Molecular Signature of Mediastinal Large B-Cell Lymphoma Differs from that of Other Diffuse Large B-cell Lymphomas and Shares Features with Classical Hodgkin Lymphoma," *Blood*, 102, 3871-3879 (2003).
Schwaenen et al., "DNA Microarray Analysis in Malignant Lymphomas," *Ann Hematol.*, 82, 323-332 (2003).
Sehn et al., "The Revised International Prognostic Index (R-IPI) is a Better Predictor of Outcome than the Standard IPI for Patients with Diffuse Large B-cell Lymphoma Treated with R-CHOP," *Blood*, 109, 1857-1861 (2007).
Shaffer et al., "A Library of Gene Expression Signatures to Illuminate Normal and Pathological Lymphoid Biology," *Immunol. Rev.*, 210, 67-85 (2006).
Shaffer et al., "Lymphoid Malignancies: The Dark Side of B-Cell Differentiation," *Nature Reviews Immunol.*, 2, 920-932 (2002).
Shipp et al., "Diffuse Large B-cell Lymphoma Outcome Prediction by Gene-Expression Profiling and Supervised Machine Learning," *Nature Medicine*, 8 (1), 68-74 (2002).
Shipp et al., "A Predictive Model for Aggressive Non-Hodgkin's Lymphoma," *N. Engl. J. Med.*, 329, 987-994 (1993).
Sonoki et al., "Cyclin D3 is a Target Gene of t(6;14)(p21.1;q32.3) of Mature B-Cell Malignancies," *Blood*, 98, 2837-2844 (2001).
Spellman et al., "Comprehensive Identification of Cell Cycle-Regulated Genes of the Yeast *Saccharomyces cerevisiae* by Microarray Hybridization," Mol. *Biol. Cell*, 9, 3273-3297 (1998).
Staudt et al., "The Biology of Human Lymphoid Malignancies Revealed by Gene Expression Profiling," *Adv. Immunol.*, 87, 163-208 (2005).
Staudt et al., "Genomic Views of the Immune System," *Annu. Rev. Immunol.*, 18, 829-859 (2000).
Staudt, "Gene Expression Profiling of Lymphoid Malignancies," *Annu. Rev. Med.*, 53, 303-318 (2002).
Staudt, "It's ALL in the Diagnosis: The molecular diagnosis of human cancer will hasten the development of treatments tailored to the abnormalities present in each patient's tumor cells. Recent gene expression profiling studies of pediatric acute lymphoblastic leukemia (ALL) suggest that the molecular diagnosis of these diseases is right around the corner," *Cancer Cell*, 1, 109-110 (2002).
Staudt et al., "Focus on Lymphomas," *Cancer Cell*, 2, 363-366 (2002).
Staudt et al., "Molecular Diagnosis of the Hematologic Cancers," *N. Engl. J. Med.*, 348, 1777-1785 (2003).
Subramanian et al., "Gene Set Enrichment Analysis: A Knowledge-based approach for Interpreting Genome-Wide Expression Profiles," *Proc. Nat'l. Acad. Sci. USA*, 102 (43), 15545-15550 (2005).
Supplementary European Search Report, Application No. 04783330.6, dated Jul. 10, 2008.
Tagawa et al., "Comparison of Genome Profiles for Identification of Distinct Subgroups of Diffuse Large B-cell Lymphoma," *Blood*, 106, 1770-1777 (2005).
Tamayo et al., "Interpreting Patterns of Gene Expression with Self-Organizing Maps: Methods and Application to Hematopoietic Differentiation," *Proc. Nat'l. Acad. Sci. USA*, 96, 2907-2912 (1999).
Tavazoie et al., "Systematic Determination of Genetic Network Architecture," *Nature Genet.*, 22, 281-285 (1999).
Wells, "Lymphoma Microenvironment Impacts Therapy and Prognosis," *Hematology Times*, http://www.hematologytimes.com/ht/ p_article_print.do?id=437§ion (2008).
Winter et al., "Prognostic Significance of Bcl-6 Protein Expression in DLBCL treated with CHOP or R-CHOP: a Prospective Correlative Study," *Blood*, 107, 4207-4213 (2006).
Wright, et al., "A Gene Expression-based Method to Diagnose Clinically Distinct Subgroups of Diffuse Large B Cell Lymphoma," *Proc. Natl. Acad. Sci. USA*, 100 (17), 9991-9996 (2003).
Yatabe et al., "Significance of Cyclin D1 Overexpression for the diagnosis of Mantle Cell Lymphoma: a Clinicopathologic Comparison of Cyclin D1-positive MCL and Cyclin D1-negative MCL-like B-cell Lymphoma," *Blood*, 95 (7), 2253-2261 (2000).

(56) References Cited

OTHER PUBLICATIONS

Ye et al., "Variable Frequencies of t(11;18)(q21;q21) in MALT Lymphomas of Different Sites: Significant Association with CagA Strains of *H pylori* in gastric MALT Lymphoma," Blood, 102, 1012-1018 (2003).
Zeller et al., "An Integrated Database of Genes Responsive to the Myc Oncogenic Transcription Factor; identification of Direct Genomic Targets," *Genome Biol.*, 4 (10), R69.1-R69.10 (2003).

\* cited by examiner

SURVIVAL PREDICTOR FOR DIFFUSE LARGE B CELL LYMPHOMA

CROSS-REFERENCE TO RELATED APPLICATION

This application is a continuation application of U.S. patent application Ser. No. 12/996,489, filed Feb. 24, 2011, which is a U.S. National Phase of International Patent Application No. PCT/US2009/046421, flied Jun. 5, 2009, which claims the benefit of U.S. Provisional Patent Application No. 61/059,678, filed on Jun. 6, 2008, the disclosure of which is incorporated b reference.

STATEMENT REGARDING FEDERALLY SPONSORED RESEARCH AND DEVELOPMENT

This invention was made with government support under Grant No. U01 CA084967, awarded by NIH. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,231,765 Byte ASCII (Text) file named "719123ST25.TXT," created on Nov. 12, 2014.

BACKGROUND OF THE INVENTION

The current standard of care for the treatment of diffuse large B cell lymphoma (DLBCL) includes anthracycline-based chemotherapy regimens such as CHOP in combination with the administration of the anti-CD20 monoclonal antibody Rituximab. This combination regimen (R-CHOP) can cure about 60% of patients and has improved the overall survival of DLBCL patients by 10-15% (Coiffier et al., *N. Engl. J. Med*, 346: 235-42 (2002)). Nonetheless, the molecular basis of response or resistance to this therapy is unknown.

DLBCL is a molecularly heterogeneous disease (Staudt et al., *Adv. Immunol.*, 87: 163-208 (2005)), and different molecular subtypes of DLBCL can have very different prognoses following treatment. For example, gene expression profiling has identified two molecular subtypes of DLBCL that are biologically and clinically distinct (Rosenwald et al., *N. Engl. J. Med.*, 346: 1937-47 (2002); Alizadeh et al., *Nature*, 403: 503-11 (2000)). The germinal center B cell-like (GCB) DLBCL subtype likely arises from normal germinal center B cells, whereas the activated B cell-like (ABC) DLBCL subtype may arise from a post-germinal center B cell that is blocked during plasmacytic differentiation. Many oncogenic mechanisms distinguish these subtypes: GCB DLBCLs have recurrent t(14,18) translocations, whereas ABC DLBCLs have recurrent trisomy 3 and deletion of the INK4a/ARF locus as well as constitutive activation of the anti-apoptotic NF-kB signalling pathway (Rosenwald et al., *N. Engl. J. Med.*, 346: 1937-47 (2002); Bea et al., *Blood*, 106: 3183-90 (2005); Tagawa et al., *Blood*, 106: 1770-77 (2005); Davis et al., *J. Exp. Med.*, 194:1861-74 (2001); Ngo et al., *Nature*, 441: 106-10 (2006); Lenz et al., *Science*, 319: 1676-79 (2008)). When treated with CHOP-like chemotherapy, the overall survival rates of patients with GCB DLBCL and ABC DLBCL were 60% and 30%, respectively (Wright et al., *Proc. Nat'l. Acad. Sci. USA*, 100: 9991-96 (2003)). Thus, the prognosis for different DLBCL can vary widely.

A separate analytical approach identified four gene expression signatures that reflect distinct DLBCL tumor attributes and that were associated with distinct survival profiles in CHOP-treated DLBCL patients (Rosenwald et al., *N. Engl. J. Med.*, 346: 1937-47 (2002)). A "germinal center B cell" (GCB) signature was associated with a favorable prognosis and paralleled the distinction between ABC and GCB DLBCL. The "proliferation" signature was associated with an adverse prognosis and included MYC and its target genes. The "MHC class II" signature was silenced in the malignant cells in a subset of DLBCL cases, an event that was associated with inferior survival (Rosenwald et al., *N. Engl. J. Med.*, 346: 1937-47 (2002); Rimsza et al., *Blood*, 103: 4251-58 (2004)). A fourth prognostic signature, termed "lymph node" signature was associated with favorable prognosis and included components of the extracellular matrix, suggesting that it reflects the nature of the tumor-infiltrating non-malignant cells. These signatures predicted survival in a statistically independent fashion, indicating that multiple biological variables dictate the response to CHOP chemotherapy in DLBCL.

Reports have suggested that the benefit of Rituximab immunotherapy might be restricted to certain molecular subtypes of DLBCL. High expression of BCL-2 or low expression of BCL-6 was associated with inferior survival with CHOP therapy. However, this distinction disappeared with R-CHOP therapy (Mounier et al., *Blood*, 101: 4279-84 (2003); Winter et al., *Blood*, 107: 4207-13 (2006)). Immunohistochemistry has also been used to distinguish DLBCLs with a germinal center versus post-germinal center phenotype. Although such immunohistochemical phenotypes were prognostically significant in CHOP-treated cases, they were not prognostic for R-CHOP-treated cases (Nyman et al., *Blood*, 109: 4930-35 (2007)).

Accordingly, there is a need for new methods of distinguishing among DLBCL subtypes that is prognostically significant for R-CHOP-treated patients.

BRIEF SUMMARY OF THE INVENTION

The invention provides methods and arrays related to a gene expression-based survival predictor for DLBCL patients, including patients treated with the current standard of care, which includes chemotherapy and the administration of Rituximab.

The invention provides a method of predicting the survival outcome of a subject suffering from diffuse large B cell lymphoma (DLBCL) that includes obtaining a gene expression profile from one or more DLBCL biopsy samples from the subject. The gene expression profile, which can be derived from gene expression product isolated from the one or more biopsy samples, includes an expression level for each gene in a germinal center B cell (GCB) gene expression signature and each gene in a stromal-1 gene expression signature. From the gene expression profile, a GCB signature value and a stromal-1 signature value are derived. From these values, a survival predictor score can be calculated using an equation that includes subtracting [(x)*(the GCB signature value)] and subtracting [(y)*(the stromal-1 signature value)]. In the equation, (x) and (y) are scale factors. A lower survival predictor score indicates a more favorable survival outcome, and a higher survival predictor score indicates a less favorable survival outcome for the subject.

The invention also provides a method of generating a survival estimate curve for subjects suffering from DLBCL. Generally the method includes obtaining a gene expression profile from one or more DLBCL biopsy samples taken from each member of a plurality of subjects. Each gene expression profile, which can be derived from gene expression product isolated from the one or more biopsy samples taken from each subject, includes an expression level for each gene in a GCB expression signature, a stromal-1 gene expression signature, and a stromal-2 gene expression signature. For each subject, the GCB signature value, the stromal-1 signature value, and the stromal-2 signature value are determined from the subject's gene expression profile, and, for each subject, a survival predictor score is generated. Each subject's survival outcome following treatment for DLBCL is tracked. A survival estimate curve is generated which correlates the probability of the tracked survival outcome with time following treatment for DLBCL and which also correlates the tracked outcome over time with the survival predictor score for the subjects.

The invention additionally provides a method of predicting the survival outcome of a subject suffering from DLBCL. Generally, the method includes obtaining a gene expression profile from one or more DLBCL biopsy samples from the subject. The gene expression profile, which can be derived from gene expression product isolated from the one or more biopsy samples, includes an expression level for each gene in a GCB gene expression signature, each gene in a stromal-1 gene expression signature, and each gene in a stromal-2 gene expression signature. The GCB signature value, the stromal-1 signature value, and the stromal-2 signature value are determined from the gene expression profile. The method then includes calculating a survival predictor score using the equation:

survival predictor score=$A-[(x)$*(the GCB signature value)]$-[(y)$*(the stromal-1 signature value)]$+[(z)$*(the stromal-2 signature value)].

In this equation, A is an offset term, and (x), (y), and (z) are scale factors. The method further includes calculating the probability of a survival outcome for the subject beyond an amount of time t following treatment for DLBCL, wherein the subject's probability of the survival outcome P(SO) is calculated using the equation:

$$P(SO)=SO_0(t)^{(exp((s)*survival\ predictor\ score))}$$

In this equation, $SO_0(t)$ is the probability of the survival outcome, which corresponds to the largest time value smaller than t in a survival outcome curve, and wherein (s) is a scale factor.

Furthermore, the invention provides a method of evaluating a subject for antiangiogenic therapy of DLBCL. The method includes obtaining a gene expression profile from one or more DLBCL biopsy samples from the subject. The gene expression profile, which can be derived from gene expression product isolated from the one or more biopsy samples, includes an expression level for each gene in a stromal-2 signature. The subject's stromal-2 signature value is then derived from the gene expression profile and evaluated to determine whether the subject's stromal-2 signature value is higher or lower than a standard stromal-2 value. If the subject's stromal-2 signature value is higher than the standard stromal-2 value, then antiangiogenic therapy is indicated, and the subject can be treated with antiangiogenic therapy. If the subject's stromal-2 signature value is not higher than the standard stromal-2 value, then antiangiogenic therapy is not indicated.

The invention also provides a second method of evaluating a subject for antiangiogenic therapy of DLBCL. The method includes obtaining a gene expression profile from one or more DLBCL biopsy samples from the subject. The gene expression profile, which can be derived from gene expression product isolated from the one or more biopsy samples, includes an expression level for each gene in a stromal-1 signature and in a stromal-2 signature. The subject's stromal-1 signature value and stromal-2 signature value are then derived from the gene expression profile. The stromal-1 signature value is subtracted from the stromal-2 signature value to thereby obtain the subject's stromal score. The subject's stromal score is evaluated to determine whether it is higher or lower than a standard stromal score. If the subject's stromal score is higher than the standard stromal score, then antiangiogenic therapy is indicated, and the subject can be treated with antiangiogenic therapy. If the subject's stromal score is not higher than the standard stromal-score, then antiangiogenic therapy is not indicated.

Additionally, the invention provides a machine-readable medium containing a digitally encoded GCB signature value, a digitally encoded stromal-1 signature value, a digitally encoded stromal-2 signature, or any combination of the foregoing signature values obtained from a subject suffering from DLBCL.

In another embodiment the invention provides a machine-readable medium containing the digitally encoded survival predictor score obtained using a method disclosed herein for predicting the survival outcome of a subject suffering from diffuse large B cell lymphoma (DLBCL). In yet another embodiment, the invention provides a machine-readable medium containing the survival estimate curve obtained using a method disclosed herein for generating a survival estimate curve for subjects suffering from DLBCL. In still another embodiment, the invention provides a machine-readable medium containing the digitally encoded probability of survival calculated according to a method disclosed herein for predicting the survival outcome (e.g., progression-free survival or overall survival) of a subject suffering from DLBCL. Furthermore, the invention provides a machine-readable medium containing the digitally encoded stromal score generated by a method disclosed herein for evaluating a subject for antiangiogenic therapy of DLBCL.

The invention also provides a targeted array comprising at least one probe or at least one set of probes for each gene in a germinal center B cell gene (GCB) expression signature, a stromal-1 gene expression signature, and a stromal-2 gene expression signature. The array can include probes for fewer than 20,000 genes or fewer than 10,000 genes.

DETAILED DESCRIPTION OF THE INVENTION

Figure 1A:
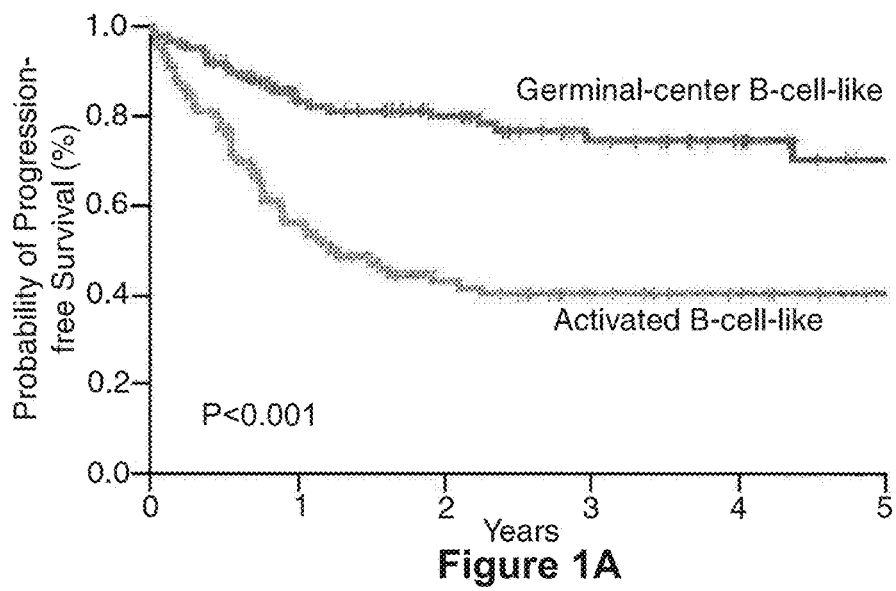
FIG. 1A is a Kaplan-Meier estimates plot depicting the probability of progression-free-survival versus time (in years) of patients with GCB DLBCL and ABC DLBCL. The plot indicates that GCB patients have a more favorable, i.e., higher probability of progression-free survival rate than ABC patients for at least five years following R-CHOP therapy.

The invention provides a gene expression-based survival predictor for DLBCL patients, including those patients receiving the current standard of care, R-CHOP. The survival predictor can be used to determine the relative probability of a survival outcome in a specific subject. The survival predictor can also be used to predict; i.e., determine the expected probability that a survival outcome will occur by a defined period following treatment for DLBCL. Such prognostic information can be very useful to both the patient and the physician. Patients with survival predictor scores that indicate inferior outcome with R-CHOP therapy could be candidates for a different therapeutic regimen, if, for example, they relapse from R-CHOP treatment. The survival predictor can also be used in the design of clinical studies and analysis of clinical data to provide a quantitative survey of the types of DLBCL patients from which clinical data was gathered. The predictor can be used to improve one or more comparisons between data from different sources (e.g., from different clinical trials), by enabling comparisons with respect to patient characteristics, which are manifested in the gene expression levels that determine and, thus, are embodied in the predictor. Furthermore, the invention provides information that can be very valuable to a DLBCL patient, since the patient may be inclined to order his or her life quite differently, depending on whether the patient has a high or low probability of surviving and/or remaining progression-free for a period of time following treatment.

The following abbreviations are used herein: ABC, activated B cell-like diffuse large B cell lymphoma; CHOP, cyclophosphamide, doxorubicine, vincristine, and prednisone; CI, confidence interval; COP, cyclophosphamide, vincristine, and prednisone; DLBCL, diffuse large B cell lymphoma; DOD, dead of disease; ECOG, Eastern Cooperative Oncology Group; FACS, fluorescence-activated cell sorting; FH, follicular hyperplasia; FISH, fluorescence in situ hybridization; FL, follicular lymphoma; GC, germinal center; GCB, germinal center B cell-like diffuse large B cell lymphoma; IPI, International Prognostic Index; LPC, lymphoplasmacytic lymphoma; MHC, major histocompatibility complex; NA, not available or not applicable; NK, natural killer; PCR, polymerase chain reaction; RQ-PCR, real-time quantitative PCR; RT-PCR, reverse transcriptase polymerase chain reaction; SAGE, serial analysis of gene expression; WHO, World Health Organization.

The term "R-CHOP" as used herein refers generally to any therapeutic regimen that includes chemotherapy and the administration of Rituximab. Accordingly, while the term can refer to a Rituximab combination therapy that includes a CHOP regimen of cyclophosphamide, doxorubicine, vincristine, and prednisone, the term R-CHOP can also refer to therapy that includes Rituximab in combination with a chemotherapeutic regimen other than CHOP.

The phrase "gene expression data" as well as "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a tumor or biopsy sample. Gene expression data and gene expression levels can be stored on computer readable media, e.g., the computer readable medium used in conjunction with a microarray or chip reading device. Such gene expression data can be manipulated to generate gene expression signatures.

The term "microarray," "array," or "chip" refers to a plurality of nucleic acid probes coupled to the surface of a substrate in different known locations. The substrate is preferably solid. Microarrays have been generally described in the art in, for example, U.S. Pat. No. 5,143,854 (Pirrung), U.S. Pat. No. 5,424,186 (Fodor), U.S. Pat. No. 5,445,934 (Fodor), U.S. Pat. No. 5,677,195 (Winkler), U.S. Pat. No. 5,744,305 (Fodor), U.S. Pat. No. 5,800,992 (Fodor), and U.S. Pat. No. 6,040,193 (Winkler), and Fodor et al., *Science*, 251: 767-777 (1991).

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer (Shaffer et al., *Immunity*, 15: 375-385 (2001)). Examples of gene expression signatures include lymph node, proliferation (Rosenwald et al., *New Engl. J. Med.*, 346: 1937-1947 (2002)), MHC class II, ABC DLBCL high, B cell differentiation, T-cell, macrophage, immune response-1, and immune response-2 signatures (U.S. Patent Application Publication No. 2007/0105136 (Staudt)).

The term "signature value" as used herein corresponds to a mathematical combination of measurements from expression levels of the genes in a gene expression signature. An exemplary signature value is a signature average which corresponds to the average or mean of the individual expression levels in a gene expression signature.

The phrase "survival predictor score" as used herein refers to a score generated by a multivariate model used to predict survival based on gene expression. A subject with a higher survival predictor score is predicted to have poorer survival than a subject with a lower survival predictor score.

The term "survival" or "overall survival" as used herein may refer to the probability or likelihood of a subject surviving for a particular period of time. Alternatively, it may refer to the likely term of survival for a subject, such as expected mean or median survival time for a subject with a particular gene expression pattern.

The term "progression free survival" as used herein can refer to the probability or likelihood of a subject surviving without significant progression or worsening of disease for a particular period of time. Alternatively, it may refer to the likely term for a subject of survival without significant progression or worsening of disease, such as expected mean or median survival time for a subject with a particular gene expression pattern without significant progression or worsening of disease.

The term "survival outcome" as used herein may refer to survival, overall survival, or progression free survival.

The phrase "scale factor" as used herein refers to a factor that relates change in gene expression to prognosis. An example of a scale factor is a factor obtained by maximizing the partial likelihoods of the Cox proportional hazards model.

The gene expression signatures, signature values, survival predictor scores, stromal scores, survival estimate curves, and probabilities of survival disclosed herein may be stored in digitally encoded format on computer readable media, e.g., computer readable media used in conjunction with microarray or chip reading devices or computer readable media used to store patient data during treatment for DLBCL. Such media and the specialized devices that use them, e.g., for diagnostic and clinical applications, are known in the art.

The invention provides a method for predicting a survival outcome in a subject diagnosed with DLBCL using gene expression data. Such data may be gathered using any effective method of quantifying gene expression. For example, gene expression data may be measured or estimated using one or more microarrays. The microarrays may be of any effective type, including, but not limited to, nucleic acid based or antibody based. Gene expression may also be measured by a variety of other techniques, including, but not limited to, PCR, quantitative RT-PCR, real-time PCR, RNA amplification, in situ hybridization, immunohistochemistry, immunocytochemistry, FACS, serial analysis of gene expression (SAGE) (Velculescu et al., *Science*, 270: 484-87 (1995)), Northern blot hybridization, or western blot hybridization.

Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the gene expression product from the sample. This gene expression product may be, for example, total cellular mRNA, rRNA, or cDNA obtained by reverse transcription of total cellular mRNA. The gene expression product from a sample is labeled with a radioactive, fluorescent, or other label to allow for detection. Following hybridization, the microarray is washed, and hybridization of the gene expression product to each nucleic acid probe on the microarray is detected and quantified using a detection device such as a phosphorimager or scanning confocal microscope.

There are two broad classes of microarrays: cDNA and oligonucleotide arrays. cDNA arrays consist of hundreds or thousands of cDNA probes immobilized on a solid support. These cDNA probes are usually 100 nucleotides or greater in size. There are two commonly used designs for cDNA arrays. The first is the nitrocellulose filter array, which is generally prepared by robotic spotting of purified DNA fragments or lysates of bacteria containing cDNA clones onto a nitrocellulose filter (Southern et al., *Genomics*, 13: 1008-17 (1992); Southern et al., *Nucl Acids Res* 22: 1368-73 (1994); Gress et al., *Oncogene*, 13: 1819-30 (1996); Pietu et al., *Genome Res.*, 6: 492-503 (1996)). The other commonly used cDNA arrays is fabricated by robotic spotting of PCR fragments from cDNA clones onto glass microscope slides (Schena et al., *Science*, 270: 467-70 (1995); DeRisi et al., *Nature Genet.*, 14: 457-60 (1996); Schena et al., *Proc. Nat'l. Acad. Sci. USA*, 93: 10614-19 (1996); Shalon et al., *Genome Res.*, 6: 639-45 (1996); DeRisi et al., *Science*, 278: 680-86 (1997); Heller et al., *Proc. Nat'l. Acad. Sci. USA*, 94: 2150-55 (1997); Lashkari et al., *Proc. Nat'l. Acad. Sci. USA*, 94: 13057-62 (1997)). These cDNA microarrays are simultaneously hybridized with two fluorescent cDNA probes, each labeled with a different fluorescent dye (typically Cy3 or Cy5). In this format, the relative mRNA expression in two samples is directly compared for each gene on the microarray. Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques (Pease et al., *Proc. Nat'l. Acad. Sci. USA*, 91: 5022-26 (1994); Lipshutz et al., *Biotechniques* 19: 442-47 (1995); Chee et al., *Science*, 274: 610-14 (1996); Lockhart et al., *Nature Biotechnol.*, 14: 1675-80 (1996); Wodicka et al., *Nature Biotechnol.*, 15: 1359-6714 (1997)). The solid support for oligonucleotide arrays is typically a glass or silicon surface.

Methods and techniques applicable to array synthesis and use have been described in, for example, U.S. Pat. No. 5,143,854 (Pirrung), U.S. Pat. No. 5,242,974 (Holmes), U.S. Pat. No. 5,252,743 (Barrett), U.S. Pat. No. 5,324,633 (Fodor), U.S. Pat. No. 5,384,261 (Winkler), U.S. Pat. No. 5,424,186 (Fodor), U.S. Pat. No. 5,445,934 (Fodor), U.S. Pat. No. 5,451,683 (Barrett), U.S. Pat. No. 5,482,867 (Barrett), U.S. Pat. No. 5,491,074 (Aldwin), U.S. Pat. No. 5,527,681 (Holmes), U.S. Pat. No. 5,550,215 (Holmes), U.S. Pat. No. 5,571,639 (Hubbell), U.S. Pat. No. 5,578,832 (Trulson), U.S. Pat. No. 5,593,839 (Hubbell), U.S. Pat. No. 5,599,695 (Pease), U.S. Pat. No. 5,624,711 (Sundberg), U.S. Pat. No. 5,631,734 (Stern), U.S. Pat. No. 5,795,716 (Chee), U.S. Pat. No. 5,831,070 (Pease), U.S. Pat. No. 5,837,832 (Chee), U.S. Pat. No. 5,856,101 (Hubbell), U.S. Pat. No. 5,858,659 (Sapolsky), U.S. Pat. No. 5,936,324 (Montagu), U.S. Pat. No. 5,968,740 (Fodor), U.S. Pat. No. 5,974,164 (Chee), U.S. Pat. No. 5,981,185 (Matson), U.S. Pat. No. 5,981,956 (Stern), U.S. Pat. No. 6,025,601 (Trulson), U.S. Pat. No. 6,033,860 (Lockhart), U.S. Pat. No. 6,040,193 (Winkler), U.S. Pat. No. 6,090,555 (Fiekowsky), and U.S. Pat. No. 6,410,229 (Lockhart), and U.S. Patent Application Publication No. 2003/0104411 (Fodor).

Microarrays may generally be produced using a variety of techniques, such as mechanical or light directed synthesis methods that incorporate a combination of photolithographic methods and solid phase synthesis methods. Techniques for the synthesis of microarrays using mechanical synthesis methods are described in, for example, U.S. Pat. No. 5,384,261 (Winkler) and U.S. Pat. No. 6,040,193 (Winkler). Although a planar array surface is preferred, the microarray may be fabricated on a surface of virtually any shape, or even on a multiplicity of surfaces. Microarrays may be nucleic acids on beads, gels, polymeric surfaces, fibers such as fiber optics, glass, or any other appropriate substrate. See, for example, U.S. Pat. No. 5,708,153 (Dower), U.S. Pat. No. 5,770,358 (Dower), U.S. Pat. No. 5,789,162 (Dower), U.S. Pat. No. 5,800,992 (Fodor), and U.S. Pat. No. 6,040,193 (Winkler).

Microarrays can be packaged in such a manner as to allow for diagnostic use, or they can be all-inclusive devices. See, for example, U.S. Pat. No. 5,856,174 (Lipshutz) and U.S. Pat. No. 5,922,591 (Anderson).

Microarrays directed to a variety of purposes are commercially available from Affymetrix (Santa Clara, Calif.). For instance, these microarrays may be used for genotyping and gene expression monitoring.

Gene expression data can be used to identify genes that are coordinately regulated. Genes that encode components of the same multi-subunit protein complex are often coordinately regulated. Coordinate regulation is also observed among genes whose products function in a common differentiation program or in the same physiological response pathway. Recent application of gene expression profiling to the immune system has shown that lymphocyte differentiation and activation are accompanied by parallel changes in expression among hundreds of genes. Gene expression databases may be used to interpret the pathological changes in gene expression that accompany autoimmunity, immune deficiencies, cancers of immune cells and of normal immune responses.

Scanning and interpreting large bodies of relative gene expression data is a formidable task. This task is greatly facilitated by algorithms designed to organize the data in a way that highlights systematic features, and by visualization tools that represent the differential expression of each gene as varying intensities and hues of color (Eisen et al., *Proc. Nat'l. Acad. Sci. USA*, 95: 14863-68 (1998)). The development of microarrays, which are capable of generating massive amounts of expression data in a single experiment, has greatly increased the need for faster and more efficient methods of analyzing large-scale expression data sets. In order to effectively utilize microarray gene expression data for the prediction of survival in DLBCL patients, there is a need for new algorithms to be developed, which can identify important information and convert it to a more manageable format. In addition, the microarrays used to generate this data can be streamlined to incorporate probe sets that are useful for survival outcome prediction.

Mathematical analysis of gene expression data is a rapidly evolving science based on a rich mathematics of pattern recognition developed in other contexts (Kohonen, *Self-Organizing Maps*, Springer Press (Berlin 1997)). Mathematical analysis of gene expression data can be used, for example, to identify groups of genes that are coordinately regulated within a biological system, to recognize and interpret similarities between biological samples on the basis of similarities in gene expression patterns, and/or to recognize and identify those features of a gene expression pattern that are related to distinct biological processes or phenotypes.

Mathematical analysis of gene expression data often begins by establishing the expression pattern for each gene on an array across a number (n) of experimental samples. The expression pattern of each gene can be represented by a point in n-dimensional space, with each coordinate specified by an expression measurement in one of the n samples (Eisen et al., *Proc. Nat'l. Acad. Sci. USA*, 95: 14863-68 (1998)). A clustering algorithm that uses distance metrics can then be applied to locate clusters of genes in this n-dimensional space. These clusters indicate genes with similar patterns of variation in expression over a series of experiments. Clustering methods that have been applied to microarray data in the past include hierarchical clustering (Eisen et al., supra), self-organizing maps (SOMs) (Tamayo et al., *Proc. Nat'l. Acad. Sci. USA*, 96: 2907-12 (1999)), k-means (Tavazoie et al., *Nature Genet.*, 22: 281-85 (1999)), and deterministic annealing (Alon et al., *Proc. Nat'l. Acad. Sci. USA*, 96: 6745-50 (1999)).

A variety of different algorithms, each emphasizing distinct orderly features of the data, may be required to glean the maximal biological insight from a set of samples (Alizadeh et al., *J. Clin. Immunol.*, 18: 373-79 (1998)). One such algorithm, hierarchical clustering, begins by determining the gene expression correlation coefficients for each pair of the n genes studied. Genes with similar gene expression correlation coefficients are grouped next to one another in a hierarchical fashion. Generally, genes with similar expression patterns under a particular set of conditions can encode protein products with related roles in the physiological adaptation to those conditions. Novel genes of unknown function that are clustered with a large group of functionally related genes likely participate in similar or related biological process. Likewise, other clustering methods mentioned herein can also group genes together that encode proteins with related biological function.

In such clustering methods, genes that are clustered together reflect a particular biological function, and are termed gene expression signatures (Shaffer et al., *Immunity* 15: 375-85 (2001)). One general type of gene expression signature includes genes that are characteristically expressed in a particular cell type or at a particular stage of cellular differentiation or activation. Another general type of gene expression signature includes genes that are regulated in their expression by a particular biological process such as proliferation, or by the activity of a particular transcription factor or signaling pathway.

The pattern of gene expression in a biological sample can provide a distinctive and accessible molecular picture of its functional state and identity (DeRisi et al., *Science*, 278: 680-86 (1997); Cho et al., *Mol. Cell.*, 2: 65-73 (1998); Chu et al., *Science*, 282: 699-705 (1998); Holstege et al., *Cell.*, 95: 717-728 (1998); Spellman et al., *Mol. Biol. Cell*, 9: 3273-97 (1998)). Each cell transduces variations in its environment, internal state, and developmental state into readily measured and recognizable variations in its gene expression patterns. Two different samples with related gene expression patterns are therefore likely to be biologically and functionally similar to one another. Thus, a specific gene expression signature in a sample can provide important biological insights into its cellular composition and the function of various intracellular pathways within those cells.

Databases of gene expression signatures have proven useful in elucidating the complex gene expression patterns of various cancers. For example, the expression pattern of genes in the germinal center B cell signature in a lymphoma biopsy indicates that the lymphoma includes cells derived from the germinal center stage of differentiation. In the same lymphoma biopsy, the expression of genes from the T cell signature can be used to estimate the degree of infiltration of the tumor by host T cells, while the expression of genes from the proliferation signature can be used to quantitate the tumor cell proliferation rate. In this manner, gene expression signatures provide an "executive summary" of the biological properties of a tumor specimen. Gene expression signatures can also be helpful in interpreting the results of a supervised analysis of gene expression data. A supervised analysis generates a list of genes with expression patterns that correlate with survival. Gene expression signatures can be useful in assigning these "predictive" genes to functional categories. In building a multivariate model of survival based on gene expression data, this functional categorization helps to limit the inclusion of multiple genes in the model that measure the same aspect of tumor biology.

This following approach was utilized to create the survival prediction models for DLBCL of the invention. Gene expression profiles were used to create multivariate models for predicting survival. The methods for creating these models were "supervised" in that they used clinical data to guide the selection of genes to be used in the prognostic classification. The method identified genes with expression patterns that correlated with the length of overall survival following chemotherapy. Generally the process for identifying the multivariate model for predicting survival included the following steps:

1. Genes were identified having expression patterns univariately associated with a particular clinical outcome using a Cox proportional hazards model. Generally, a univariate p-value of <0.01 is considered the cut-off for significance (however, another criterion can be used). These genes were termed "predictor" genes.
2. Within a set of predictor genes, gene expression signatures were identified.
3. For each gene expression signature significantly associated with survival, the average expression of each component genes within this signature was used to generate a gene expression signature value.
4. A multivariate Cox model of clinical outcome using the gene expression signature values was built.
5. Additional genes were added to the model, which added to the statistical power of the model.

The model of the invention generates a survival predictor score, with a higher score being associated with worse clinical outcome. The resulting model can be used separately to predict a survival outcome. Alternatively, the model can be used in conjunction with one or more other models, disclosed herein or in other references, to predict a survival outcome.

The present invention discloses several gene expression signatures related to the clinical outcome of DLBCL patients. The signatures were identified using the clinical data and methods described below in Examples 1 and 2. Three of these gene expression signatures are the germinal center B cell (GCB) signature, the stromal-1 signature, and the stromal-2 signature. Each component gene of these signatures is identified in Table 1 according to its GenBank accession number, its GeneID assigned by Entrez Gene, a common gene symbol, and a descriptive gene title. Table 1 also provides the Affymetrix Probe Set ID, which can be used (e.g., on the Affymetrix U133+ (Affymetrix, Santa Clara, Calif.) microarray) to determine the gene expression level for the indicated gene. The computer-readable sequence listing filed herewith includes a representative fragment sequence (of about 100 bp or greater) for each genomic target sequence listed in Table 1, followed by the sequence for each probe in the corresponding Affymetrix probe set listed in Table 1.

TABLE 1

| Signature | GenBank Accession No. | Entrez GeneID | Gene Symbol | Gene Title | Affymetrix Probe Set ID |
|---|---|---|---|---|---|
| GCB | NM_052932 | 114908 | TMEM123 | transmembrane protein 123 | 211967_at |
| GCB | NM_001014380 | 84056 | KATNAL1 | katanin p60 subunit A-like 1 | 227713_at |
| GCB | NM_004665 | 8875 | VNN2 | vanin 2 | 205922_at |
| GCB | NM_004760 | 9263 | STK17A | serine/threonine kinase 17a (apoptosis-inducing) | 202693_s_at |
| GCB | CR590554 | | | Full-length cDNA clone CS0DF007YJ21 of Fetal brain of *Homo sapiens* (human) | 228464_at |
| GCB | NM_017599 | 55591 | VEZT | vezatin, adherens junctions transmembrane protein | 223089_at |
| GCB | NM_018351 | 55785 | FGD6 | FYVE, RhoGEF and PH domain containing 6 | 1555136_at |
| GCB | NM_001007075 | 51088 | KLHL5 | kelch-like 5 (*Drosophila*) | 226001_at |
| GCB | NM_004845 | 9468 | PCYT1B | phosphate cytidylyltransferase 1, choline, beta | 228959_at |
| GCB | AK026881 | | | CDNA: FLJ23228 fis, clone CAE06654 | 226799_at |
| GCB | NM_018440 | 55824 | PAG1 | phosphoprotein associated with glycosphingolipid microdomains 1 | 225626_at |
| GCB | NM_004965 | 3150 | HMGN1 | high-mobility group nucleosome binding domain 1 | 200944_s_at |
| GCB | NM_001706 | 604 | BCL6 | B cell CLL/lymphoma 6 (zinc finger protein 51) | 228758_at |

TABLE 1-continued

| Signature | GenBank Accession No. | Entrez GeneID | Gene Symbol | Gene Title | Affymetrix Probe Set ID |
|---|---|---|---|---|---|
| GCB | NM_020747 | 57507 | ZNF608 | zinc finger protein 608 | 229817_at |
| GCB | NM_001001695 | 400941 | FLJ42418 | FLJ42418 protein | 231455_at |
| GCB | NM_015055 | 23075 | SWAP70 | SWAP-70 protein | 209306_s_at |
| GCB | NM_005607 | 5747 | PTK2 | PTK2 protein tyrosine kinase 2 | 208820_at |
| GCB | XM_027236 | 23508 | TTC9 | tetratricopeptide repeat domain 9 | 213172_at |
| GCB | BQ213652 | 440864 | LOC440864 | hypothetical gene supported by BC040724 | 1569034_a_at |
| GCB | NM_005574 | 4005 | LMO2 | LIM domain only 2 (rhombotin-like 1) | 204249_s_at |
| GCB | NM_014667 | 9686 | VGLL4 | vestigial like 4 (*Drosophila*) | 212399_s_at |
| GCB | NM_002221 | 3707 | ITPKB | inositol 1,4,5-trisphosphate 3-kinase B | 203723_at |
| GCB | NM_000902 | 4311 | MME | membrane metallo-endopeptidase (neutral endopeptidase, enkephalinase) | 203434_s_at |
| GCB | NM_012446 | 23635 | SSBP2 | single-stranded DNA binding protein 2 | 203787_at |
| GCB | NM_024613 | 79666 | PLEKHF2 | pleckstrin homology domain containing, family F (with FYVE domain) member 2 | 222699_s_at |
| GCB | AV705976 | | | Transcribed locus | 204681_s_at |
| GCB | NM_012108 | 26228 | BRDG1 | BCR downstream signaling 1 | 220059_at |
| GCB | NM_014397 | 10783 | NEK6 | NIMA (never in mitosis gene a)-related kinase 6 | 223158_s_at |
| GCB | NM_018981 | 54431 | DNAJC10 | DnaJ (Hsp40) homolog, subfamily C, member 10 | 225174_at |
| GCB | NM_001379 | 1786 | DNMT1 | DNA (cytosine-5-)-methyltransferase 1 | 227684_at |
| GCB | NM_006152 | 4033 | LRMP | lymphoid-restricted membrane protein | 35974_at |
| GCB | NM_024701 | 79754 | ASB13 | ankyrin repeat and SOCS box-containing 13 | 218862_at |
| GCB | NM_006085 | 10380 | BPNT1 | 3'(2'), 5'-bisphosphate nucleotidase 1 | 232103_at |
| GCB | NM_023009 | 65108 | MARCKSL1 | MARCKS-like 1 | 200644_at |
| GCB | NM_033121 | 88455 | ANKRD13A | ankyrin repeat domain 13A | 224810_s_at |
| GCB | NM_015187 | 23231 | KIAA0746 | KIAA0746 protein | 235353_at |
| GCB | NM_175739 | 327657 | SERPINA9 | serpin peptidase inhibitor, clade A (alpha-1 antiproteinase, antitrypsin), member 9 | 1553499_s_at |
| GCB | NM_001012391 | 400509 | RUNDC2B | RUN domain containing 2B | 1554413_s_at |
| GCB | XM_034274 | 4603 | MYBL1 | v-myb myeloblastosis viral oncogene homolog (avian)-like 1 | 213906_at |
| Stromal-1 | NM_024579 | 79630 | C1orf54 | chromosome 1 open reading frame 54 | 219506_at |
| Stromal-1 | NM_001645 | 341 | APOC1 | apolipoprotein C-I | 213553_x_at |
| Stromal-1 | NM_001562 | 3606 | IL18 | interleukin 18 (interferon-gamma-inducing factor) | 206295_at |
| Stromal-1 | NM_014479 | 27299 | ADAMDEC1 | ADAM-like, decysin 1 | 206134_at |
| Stromal-1 | NM_003465 | 1118 | CHIT1 | chitinase 1 (chitotriosidase) | 208168_s_at |
| Stromal-1 | NM_000954 | 5730 | PTGDS | prostaglandin D2 synthase 21 kDa (brain) | 211748_x_at |
| Stromal-1 | NM_001056 | 6819 | SULT1C1 | sulfotransferase family, cytosolic, 1C, member 1 | 211470_s_at |
| Stromal-1 | NM_018000 | 55686 | MREG | melanoregulin | 219648_at |
| Stromal-1 | NM_001018058 | 22797 | TFEC | transcription factor EC | 206715_at |
| Stromal-1 | NM_000239 | 4069 | LYZ | lysozyme (renal amyloidosis) | 213975_s_at |
| Stromal-1 | NM_006834 | 10981 | RAB32 | RAB32, member RAS oncogene family | 204214_s_at |
| Stromal-1 | NM_000416 | 3459 | IFNGR1 | interferon gamma receptor 1 | 202727_s_at |
| Stromal-1 | NM_004666 | 8876 | VNN1 | vanin 1 | 205844_at |
| Stromal-1 | NM_031491 | 83758 | RBP5 | retinol binding protein 5, cellular | 223820_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | NM_001276 | 1116 | CHI3L1 | chitinase 3-like 1 (cartilage glycoprotein-39) | 209396_s_at |
| Stromal-1 | NM_138434 | 113763 | C7orf29 | chromosome 7 open reading frame 29 | 227598_at |
| Stromal-1 | NM_001005340 | 10457 | GPNMB | glycoprotein (transmembrane) nmb | 201141_at |
| Stromal-1 | NM_002294 | 3920 | LAMP2 | lysosomal-associated membrane protein 2 | 203041_s_at |
| Stromal-1 | NM_002888 | 5918 | RARRES1 | retinoic acid receptor responder (tazarotene induced) 1 | 221872_at |
| Stromal-1 | NM_172248 | 1438 | CSF2RA | colony stimulating factor 2 receptor, alpha, low-affinity (granulocyte-macrophage) | 210340_s_at |
| Stromal-1 | NM_018344 | 55315 | SLC29A3 | solute carrier family 29 (nucleoside transporters), member 3 | 219344_at |
| Stromal-1 | NM_032413 | 84419 | C15orf48 | chromosome 15 open reading frame 48 | 223484_at |
| Stromal-1 | NM_001001851 | 80760 | ITIH5 | inter-alpha (globulin) inhibitor H5 | 1553243_at |
| Stromal-1 | NM_000211 | 3689 | ITGB2 | integrin, beta 2 (complement component 3 receptor 3 and 4 subunit) | 1555349_a_at |
| Stromal-1 | NM_005213 | 1475 | CSTA | cystatin A (stefin A) | 204971_at |
| Stromal-1 | NM_003874 | 8832 | CD84 | CD84 molecule | 205988_at |
| Stromal-1 | NM_000228 | 3914 | LAMB3 | laminin, beta 3 | 209270_at |
| Stromal-1 | NM_005651 | 6999 | TDO2 | tryptophan 2,3-dioxygenase | 205943_at |
| Stromal-1 | NM_001005266 | 283651 | C15orf21 | chromosome 15 open reading frame 21 | 242649_x_at |
| Stromal-1 | AV659177 | | | Transcribed locus | 230391_at |
| Stromal-1 | NM_001747 | 822 | CAPG | capping protein (actin filament), gelsolin-like | 201850_at |
| Stromal-1 | NM_000784 | 1593 | CYP27A1 | cytochrome P450, family 27, subfamily A, polypeptide 1 | 203979_at |
| Stromal-1 | NM_052998 | 113451 | ADC | arginine decarboxylase | 228000_at |
| Stromal-1 | NM_016240 | 51435 | SCARA3 | scavenger receptor class A, member 3 | 219416_at |
| Stromal-1 | Z74615 | | COL1A1 | Collagen, type I, alpha 1 | 217430_x_at |
| Stromal-1 | NM_052947 | 115701 | ALPK2 | alpha-kinase 2 | 228367_at |
| Stromal-1 | NM_021136 | 6252 | RTN1 | reticulon 1 | 210222_s_at |
| Stromal-1 | AL049370 | | | Full-length cDNA clone CL0BB018ZE07 of Neuroblastoma of *Homo sapiens* (human) | 213100_at |
| Stromal-1 | NM_006042 | 9955 | HS3ST3A1 | heparan sulfate (glucosamine) 3-O-sulfotransferase 3A1 | 219985_at |
| Stromal-1 | NM_000041 | 348 | APOE | apolipoprotein E | 203382_s_at |
| Stromal-1 | NM_004994 | 4318 | MMP9 | matrix metallopeptidase 9 (gelatinase B, 92 kDa gelatinase, 92 kDa type IV collagenase) | 203936_s_at |
| Stromal-1 | NM_001831 | 1191 | CLU | clusterin | 222043_at |
| Stromal-1 | NM_002305 | 3956 | LGALS1 | lectin, galactoside-binding, soluble, 1 (galectin 1) | 201105_at |
| Stromal-1 | NM_032024 | 83938 | C10orf11 | chromosome 10 open reading frame 11 | 223703_at |
| Stromal-1 | NM_001025201 | 1123 | CHN1 | chimerin (chimaerin) 1 | 212624_s_at |
| Stromal-1 | NM_003489 | 8204 | NRIP1 | nuclear receptor interacting protein 1 | 202599_s_at |
| Stromal-1 | NM_032646 | 94015 | TTYH2 | tweety homolog 2 (*Drosophila*) | 223741_s_at |
| Stromal-1 | NM_001312 | 1397 | CRIP2 | cysteine-rich protein 2 | 208978_at |
| Stromal-1 | NM_023075 | 65258 | MPPE1 | metallophosphoesterase 1 | 213924_at |
| Stromal-1 | NM_004364 | 1050 | CEBPA | CCAAT/enhancer binding protein (C/EBP), alpha | 204039_at |
| Stromal-1 | NM_000248 | 4286 | MITF | microphthalmia-associated transcription factor | 207233_s_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | NM_002185 | 3575 | IL7R | interleukin 7 receptor | 226218_at |
| Stromal-1 | NM_021638 | 60312 | AFAP | actin filament associated protein | 203563_at |
| Stromal-1 | NM_003786 | 8714 | ABCC3 | ATP-binding cassette, sub-family C (CFTR/MRP), member 3 | 208161_s_at |
| Stromal-1 | | 730351 | LOC730351 | hypothetical protein LOC730351 | 229407_at |
| Stromal-1 | NM_012153 | 26298 | EHF | ets homologous factor | 225645_at |
| Stromal-1 | NM_004887 | 9547 | CXCL14 | chemokine (C-X-C motif) ligand 14 | 222484_s_at |
| Stromal-1 | NM_002030 | 2359 | FPRL2 | formyl peptide receptor-like 2 | 230422_at |
| Stromal-1 | NM_001321 | 1466 | CSRP2 | cysteine and glycine-rich protein 2 | 207030_s_at |
| Stromal-1 | NM_001945 | 1839 | HBEGF | heparin-binding EGF-like growth factor | 203821_at |
| Stromal-1 | NM_031412 | 23710 | GABARAPL1 | GABA(A) receptor-associated protein like 1 | 208869_s_at |
| Stromal-1 | NM_006022 | 8848 | TSC22D1 | TSC22 domain family, member 1 | 215111s_at |
| Stromal-1 | NM_016174 | 51148 | CEECAM1 | cerebral endothelial cell adhesion molecule 1 | 224794_s_at |
| Stromal-1 | NM_015103 | 23129 | PLXND1 | plexin D1 | 212235_at |
| Stromal-1 | NM_003270 | 7105 | TSPAN6 | tetraspanin 6 | 209109_s_at |
| Stromal-1 | NM_000887 | 3687 | ITGAX | integrin, alpha X (complement component 3 receptor 4 subunit) | 210184_at |
| Stromal-1 | NM_001864 | 1346 | COX7A1 | cytochrome c oxidase subunit VIIa polypeptide 1 (muscle) | 204570_at |
| Stromal-1 | CR599008 | | GPR157 | Full-length cDNA clone CS0DJ007YL22 of T cells (Jurkat cell line) Cot 10-normalized of Homo sapiens (human) | 227970_at |
| Stromal-1 | NM_198580 | 376497 | SLC27A1 | solute carrier family 27 (fatty acid transporter), member 1 | 226728_at |
| Stromal-1 | NM_025106 | 80176 | SPSB1 | splA/ryanodine receptor domain and SOCS box containing 1 | 226075_at |
| Stromal-1 | NM_020130 | 56892 | C8orf4 | chromosome 8 open reading frame 4 | 218541_s_at |
| Stromal-1 | NM_173833 | 286133 | SCARA5 | scavenger receptor class A, member 5 (putative) | 229839_at |
| Stromal-1 | NM_007223 | 11245 | GPR176 | G protein-coupled receptor 176 | 227846_at |
| Stromal-1 | NM_013437 | 29967 | LRP12 | low density lipoprotein-related protein 12 | 219631_at |
| Stromal-1 | NM_007332 | 8989 | TRPA1 | transient receptor potential cation channel, subfamily A, member 1 | 228438_at |
| Stromal-1 | NM_152744 | 221935 | SDK1 | sidekick homolog 1 (chicken) | 229912_at |
| Stromal-1 | NM_001409 | 1953 | MEGF6 | multiple EGF-like-domains 6 | 226869_at |
| Stromal-1 | NM_012082 | 23414 | ZFPM2 | zinc finger protein, multitype 2 | 219778_at |
| Stromal-1 | NM_080430 | 140606 | SELM | selenoprotein M | 226051_at |
| Stromal-1 | NM_030971 | 81855 | SFXN3 | sideroflexin 3 | 217226_s_at |
| Stromal-1 | NM_003246 | 7057 | THBS1 | thrombospondin 1 | 201109_s_at |
| Stromal-1 | NM_003882 | 8840 | WISP1 | WNT1 inducible signaling pathway protein 1 | 235821_at |
| Stromal-1 | NM_005202 | 1296 | COL8A2 | collagen, type VIII, alpha 2 | 221900_at |
| Stromal-1 | NM_003711 | 8611 | PPAP2A | phosphatidic acid phosphatase type 2A | 210946_at |
| Stromal-1 | NM_004995 | 4323 | MMP14 | matrix metallopeptidase 14 (membrane-inserted) | 202828_s_at |
| Stromal-1 | NM_001005336 | 1759 | DNM_1 | dynamin 1 | 215116_s_at |
| Stromal-1 | NM_153717 | 2121 | EVC | Ellis van Creveld syndrome | 219432_at |
| Stromal-1 | NM_173462 | 89932 | PAPLN | papilin, proteoglycan-like sulfated glycoprotein | 226435_at |
| Stromal-1 | XM_496707 | 441027 | FLJ12993 | hypothetical LOC441027 | 229623_at |
| Stromal-1 | NM_001839 | 1266 | CNN3 | calponin 3, acidic | 228297_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | NM_015429 | 25890 | ABI3BP | ABI gene family, member 3 (NESH) binding protein | 223395_at |
| Stromal-1 | NM_002840 | 5792 | PTPRF | protein tyrosine phosphatase, receptor type, F | 200636_s_at |
| Stromal-1 | NM_001001522 | 6876 | TAGLN | transgelin | 1555724_s_at |
| Stromal-1 | NM_017637 | 54796 | BNC2 | basonuclin 2 | 229942_at |
| Stromal-1 | NM_003391 | 7472 | WNT2 | wingless-type MMTV integration site family member 2 | 205648_at |
| Stromal-1 | NM_015461 | 25925 | ZNF521 | zinc finger protein 521 | 226677_at |
| Stromal-1 | NM_006475 | 10631 | POSTN | periostin, osteoblast specific factor | 210809_s_at |
| Stromal-1 | NM_005418 | 6764 | ST5 | suppression of tumorigenicity 5 | 202440_s_at |
| Stromal-1 | NM_005203 | 1305 | COL13A1 | collagen, type XIII, alpha 1 | 211343_s_at |
| Stromal-1 | NM_000681 | 150 | ADRA2A | adrenergic, alpha-2A-, receptor | 209869_at |
| Stromal-1 | NM_006622 | 10769 | PLK2 | polo-like kinase 2 (*Drosophila*) | 201939_at |
| Stromal-1 | AL528626 | | | Full-length cDNA clone CS0DD001YA12 of Neuroblastoma Cot 50-normalized of *Homo sapiens* (human) | 228573_at |
| Stromal-1 | AF180519 | 23766 | GABARAPL3 | GABA(A) receptors associated protein like 3 | 211458_s_at |
| Stromal-1 | NM_024723 | 79778 | MICALL2 | MICAL-like 2 | 219332_at |
| Stromal-1 | NM_057177 | 117583 | PARD3B | par-3 partitioning defective 3 homolog B (*C. elegans*) | 228411_at |
| Stromal-1 | NM_004949 | 1824 | DSC2 | desmocollin 2 | 226817_at |
| Stromal-1 | NM_032784 | 84870 | RSPO3 | R-spondin 3 homolog (*Xenopus laevis*) | 228186_at |
| Stromal-1 | NM_007039 | 11099 | PTPN21 | protein tyrosine phosphatase, non-receptor type 21 | 226380_at |
| Stromal-1 | NM_031935 | 83872 | HMCN1 | hemicentin 1 | 235944_at |
| Stromal-1 | AK022877 | | | Clone TUA8 Cri-du-ch region mRNA | 213169_at |
| Stromal-1 | AK127644 | | | CDNA FLJ45742 fis, clone KIDNE2016327 | 236297_at |
| Stromal-1 | AK056963 | | | Full length insert cDNA clone ZE03F06 | 226282_at |
| Stromal-1 | NM_000899 | 4254 | KITLG | KIT ligand | 226534_at |
| Stromal-1 | NM_002387 | 4163 | MCC | mutated in colorectal cancers | 226225_at |
| Stromal-1 | NM_198270 | 4810 | NHS | Nance-Horan syndrome (congenital cataracts and dental anomalies) | 228933_at |
| Stromal-1 | NM_183376 | 91947 | ARRDC4 | arrestin domain containing 4 | 225283_at |
| Stromal-1 | NM_000216 | 3730 | KAL1 | Kallmann syndrome 1 sequence | 205206_at |
| Stromal-1 | NM_001008224 | 55075 | UACA | uveal autoantigen with coiled-coil domains and ankyrin repeats | 223279_s_at |
| Stromal-1 | NM_133493 | 135228 | CD109 | CD109 molecule | 226545_at |
| Stromal-1 | NM_005545 | 3671 | ISLR | immunoglobulin superfamily containing leucine-rich repeat | 207191_s_at |
| Stromal-1 | NM_014365 | 26353 | HSPB8 | heat shock 22 kDa protein 8 | 221667_s_at |
| Stromal-1 | NM_014476 | 27295 | PDLIM3 | PDZ and LIM domain 3 | 209621_s_at |
| Stromal-1 | NM_020962 | 57722 | NOPE | likely ortholog of mouse neighbor of Punc E11 | 227870_at |
| Stromal-1 | NM_018357 | 55323 | LARP6 | La ribonucleoprotein domain family, member 6 | 218651_s_at |
| Stromal-1 | NM_012323 | 23764 | MAFF | v-maf musculoaponeurotic fibrosarcoma oncogene homolog F (avian) | 36711_at |
| Stromal-1 | NM_003713 | 8613 | PPAP2B | phosphatidic acid phosphatase type 2B | 212230_at |
| Stromal-1 | NM_023016 | 65124 | ANKRD57 | ankyrin repeat domain 57 | 227034_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | NM_032777 | 25960 | GPR124 | G protein-coupled receptor 124 | 65718_at |
| Stromal-1 | NM_001554 | 3491 | CYR61 | cysteine-rich, angiogenic inducer, 61 | 201289_at |
| Stromal-1 | NM_145117 | 89797 | NAV2 | neuron navigator 2 | 218330_s_at |
| Stromal-1 | NM_001002292 | 79971 | GPR177 | G protein-coupled receptor 177 | 228950_s_at |
| Stromal-1 | NM_001401 | 1902 | EDG2 | endothelial differentiation, lysophosphatidic acid G-protein-coupled receptor, 2 | 204036_at |
| Stromal-1 | NM_198282 | 340061 | TMEM173 | transmembrane protein 173 | 224929_at |
| Stromal-1 | NM_014934 | 22873 | DZIP1 | DAZ interacting protein 1 | 204556_s_at |
| Stromal-1 | NM_001901 | 1490 | CTGF | connective tissue growth factor | 209101_at |
| Stromal-1 | NM_024600 | 79652 | C16orf30 | chromosome 16 open reading frame 30 | 219315_s_at |
| Stromal-1 | NM_138370 | 91461 | LOC91461 | hypothetical protein BC007901 | 225380_at |
| Stromal-1 | NM_014632 | 9645 | MICAL2 | microtubule associated monoxygenase, calponin and LIM domain containing 2 | 212472_at |
| Stromal-1 | NM_032866 | 84952 | CGNL1 | cingulin-like 1 | 225817_at |
| Stromal-1 | NM_003687 | 8572 | PDLIM4 | PDZ and LIM domain 4 | 211564_s_at |
| Stromal-1 | BM544548 | | | Transcribed locus | 236179_at |
| Stromal-1 | NM_001856 | 1307 | COL16A1 | collagen, type XVI, alpha 1 | 204345_at |
| Stromal-1 | XM_087386 | 57493 | HEG1 | HEG homolog 1 (zebrafish) | 213069_at |
| Stromal-1 | NM_003887 | 8853 | DDEF2 | development and differentiation enhancing factor 2 | 206414_s_at |
| Stromal-1 | NM_002844 | 5796 | PTPRK | protein tyrosine phosphatase, receptor type, K | 203038_at |
| Stromal-1 | NM_022138 | 64094 | SMOC2 | SPARC related modular calcium binding 2 | 223235_s_at |
| Stromal-1 | NM_001006624 | 10630 | PDPN | podoplanin | 204879_at |
| Stromal-1 | NM_003174 | 6840 | SVIL | supervillin | 202565_s_at |
| Stromal-1 | NM_002845 | 5797 | PTPRM | protein tyrosine phosphatase, receptor type, M | 1555579_s_at |
| Stromal-1 | NM_002889 | 5919 | RARRES2 | retinoic acid receptor responder (tazarotene induced) 2 | 209496_at |
| Stromal-1 | NM_006094 | 10395 | DLC1 | deleted in liver cancer 1 | 210762_s_at |
| Stromal-1 | NM_022463 | 64359 | NXN | nucleoredoxin | 219489_s_at |
| Stromal-1 | AK027294 | | | CDNA FLJ14388 fis, clone HEMBA1002716 | 229802_at |
| Stromal-1 | NM_005711 | 10085 | EDIL3 | EGF-like repeats and discoidin I-like domains 3 | 225275_at |
| Stromal-1 | NM_000177 | 2934 | GSN | gelsolin (amyloidosis, Finnish type) | 200696_s_at |
| Stromal-1 | NM_016639 | 51330 | TNFRSF12A | tumor necrosis factor receptor superfamily, member 12A | 218368_s_at |
| Stromal-1 | NM_004460 | 2191 | FAP | fibroblast activation protein, alpha | 209955_s_at |
| Stromal-1 | NM_000064 | 718 | C3 | complement component 3 | 217767_at |
| Stromal-1 | NM_016206 | 389136 | VGLL3 | vestigial like 3 (Drosophila) | 227399_at |
| Stromal-1 | NM_004339 | 754 | PTTG1IP | pituitary tumor-transforming 1 interacting protein | 200677_at |
| Stromal-1 | NM_003255 | 7077 | TIMP2 | TIMP metallopeptidase inhibitor 2 | 224560_at |
| Stromal-1 | NM_002998 | 6383 | SDC2 | syndecan 2 (heparan sulfate proteoglycan 1, cell surface-associated, fibroglycan) | 212158_at |
| Stromal-1 | NM_012223 | 4430 | MYO1B | myosin IB | 212364_at |
| Stromal-1 | NM_020650 | 57333 | RCN3 | reticulocalbin 3, EF-hand calcium binding domain | 61734_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | AL573464 | | | Transcribed locus | 229554_at |
| Stromal-1 | AK001903 | | | CDNA FLJ11041 fis, clone PLACE1004405 | 227140_at |
| Stromal-1 | NM_005928 | 4240 | MFGE8 | milk fat globule-EGF factor 8 protein | 210605_s_at |
| Stromal-1 | NM_000943 | 5480 | PPIC | peptidylprolyl isomerase C (cyclophilin C) | 204518_s_at |
| Stromal-1 | NM_001008397 | 493869 | LOC493869 | similar to RIKEN cDNA 2310016C16 | 227628_at |
| Stromal-1 | AK025431 | 768211 | RELL1 | receptor expressed in lymphoid tissues like 1 | 226430_at |
| Stromal-1 | NM_000297 | 5311 | PKD2 | polycystic kidney disease 2 (autosomal dominant) | 203688_at |
| Stromal-1 | NM_002975 | 6320 | CLEC11A | C-type lectin domain family 11, member A | 211709_s_at |
| Stromal-1 | NM_001920 | 1634 | DCN | decorin | 211813_x_at |
| Stromal-1 | NM_001723 | 667 | DST | dystonin | 215016_x_at |
| Stromal-1 | CR749529 | | | MRNA; cDNA DKFZp686I18116 (from clone DKFZp686I18116) | 227554_at |
| Stromal-1 | NM_000165 | 2697 | GJA1 | gap junction protein, alpha 1, 43 kDa (connexin 43) | 201667_at |
| Stromal-1 | NM_012104 | 23621 | BACE1 | beta-site APP-cleaving enzyme 1 | 217904_s_at |
| Stromal-1 | NM_001957 | 1909 | EDNRA | endothelin receptor type A | 204464_s_at |
| Stromal-1 | NM_138455 | 115908 | CTHRC1 | collagen triple helix repeat containing 1 | 225681_at |
| Stromal-1 | NM_001331 | 1500 | CTNND1 | catenin (cadherin-associated protein), delta 1 | 208407_s_at |
| Stromal-1 | NM_001613 | 59 | ACTA2 | actin, alpha 2, smooth muscle, aorta | 200974_at |
| Stromal-1 | NM_002192 | 3624 | INHBA | inhibin, beta A (activin A, activin AB alpha polypeptide) | 210511_s_at |
| Stromal-1 | NM_000935 | 5352 | PLOD2 | procollagen-lysine, 2-oxoglutarate 5-dioxygenase 2 | 202620_s_at |
| Stromal-1 | NM_015170 | 23213 | SULF1 | sulfatase 1 | 212354_at |
| Stromal-1 | NM_006039 | 9902 | MRC2 | mannose receptor, C type 2 | 37408_at |
| Stromal-1 | NM_005261 | 2669 | GEM | GTP binding protein overexpressed in skeletal muscle | 204472_at |
| Stromal-1 | NM_001008707 | 2009 | EML1 | echinoderm microtubule associated protein like 1 | 204797_s_at |
| Stromal-1 | NM_001031679 | 253827 | MSRB3 | methionine sulfoxide reductase B3 | 225782_at |
| Stromal-1 | NM_001004125 | 286319 | TUSC1 | tumor suppressor candidate 1 | 227388_at |
| Stromal-1 | NM_005965 | 4638 | MYLK | myosin, light chain kinase | 202555_s_at |
| Stromal-1 | NM_016205 | 56034 | PDGFC | platelet derived growth factor C | 218718_at |
| Stromal-1 | NM_015976 | 51375 | SNX7 | sorting nexin 7 | 205573_s_at |
| Stromal-1 | NM_130830 | 131578 | LRRC15 | leucine rich repeat containing 15 | 213909_at |
| Stromal-1 | NM_002026 | 2335 | FN1 | fibronectin 1 | 212464_s_at |
| Stromal-1 | NM_006855 | 11015 | KDELR3 | KDEL (Lys-Asp-Glu-Leu) endoplasmic reticulum protein retention receptor 3 | 204017_at |
| Stromal-1 | NM_002292 | 3913 | LAMB2 | laminin, beta 2 (laminin S) | 216264_s_at |
| Stromal-1 | NM_002658 | 5328 | PLAU | plasminogen activator, urokinase | 205479_s_at |
| Stromal-1 | NM_005529 | 3339 | HSPG2 | heparan sulfate proteoglycan 2 (perlecan) | 201655_s_at |
| Stromal-1 | NM_001235 | 871 | SERPINH1 | serpin peptidase inhibitor, clade H (heat shock protein 47), member 1, (collagen binding protein 1) | 207714_s_at |
| Stromal-1 | AJ318805 | | | CDNA FLJ44429 fis, clone UTERU2015653 | 227061_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | NM_000396 | 1513 | CTSK | cathepsin K | 202450_s_at |
| Stromal-1 | NM_031302 | 83468 | GLT8D2 | glycosyltransferase 8 domain containing 2 | 227070_at |
| Stromal-1 | NM_080821 | 116151 | C20orf108 | chromosome 20 open reading frame 108 | 224690_at |
| Stromal-1 | NM_002345 | 4060 | LUM | lumican | 201744_s_at |
| Stromal-1 | NM_005110 | 9945 | GFPT2 | glutamine-fructose-6-phosphate transaminase 2 | 205100_at |
| Stromal-1 | NM_002941 | 6091 | ROBO1 | roundabout, axon guidance receptor, homolog 1 (Drosophila) | 213194_at |
| Stromal-1 | NM_005429 | 7424 | VEGFC | vascular endothelial growth factor C | 209946_at |
| Stromal-1 | NM_002213 | 3693 | ITGB5 | integrin, beta 5 | 201125_s_at |
| Stromal-1 | XM_051017 | 23363 | OBSL1 | obscurin-like 1 | 212775_at |
| Stromal-1 | NM_181724 | 338773 | TMEM119 | transmembrane protein 119 | 227300_at |
| Stromal-1 | NM_003474 | 8038 | ADAM12 | ADAM metallopeptidase domain 12 (meltrin alpha) | 213790_at |
| Stromal-1 | NM_018222 | 55742 | PARVA | parvin, alpha | 217890_s_at |
| Stromal-1 | NM_006478 | 10634 | GAS2L1 | growth arrest-specific 2 like 1 | 31874_at |
| Stromal-1 | NM_000093 | 1289 | COL5A1 | collagen, type V, alpha 1 | 212489_at |
| Stromal-1 | NM_006288 | 7070 | THY1 | Thy-1 cell surface antigen | 208851_s_at |
| Stromal-1 | CD357685 | | TIMP2 | Transcribed locus, strongly similar to XP_511714.1 similar to Metalloproteinase inhibitor 2 precursor (TIMP-2) (Tissue inhibitor of metalloproteinases-2) (CSC-21K) [Pan troglodytes] | 231579_s_at |
| Stromal-1 | NM_003247 | 7058 | THBS2 | thrombospondin 2 | 203083_at |
| Stromal-1 | NM_000088 | 1277 | COL1A1 | collagen, type I, alpha 1 | 1556499_s_at |
| Stromal-1 | NM_006832 | 10979 | PLEKHC1 | pleckstrin homology domain containing, family C (with FERM domain) member 1 | 209210_s_at |
| Stromal-1 | NM_021961 | 7003 | TEAD1 | TEA domain family member 1 (SV40 transcriptional enhancer factor) | 224955_at |
| Stromal-1 | AK128814 | | | CDNA FLJ25106 fis, clone CBR01467 | 213675_at |
| Stromal-1 | NM_153367 | 219654 | C10orf56 | chromosome 10 open reading frame 56 | 212423_at |
| Stromal-1 | AK092048 | | | MRNA; cDNA DKFZp313C0240 (from clone DKFZp313C0240) | 227623_at |
| Stromal-1 | NM_005245 | 2195 | FAT | FAT tumor suppressor homolog 1 (Drosophila) | 201579_at |
| Stromal-1 | NM_001129 | 165 | AEBP1 | AE binding protein 1 | 201792_at |
| Stromal-1 | NM_002403 | 4237 | MFAP2 | microfibrillar-associated protein 2 | 203417_at |
| Stromal-1 | NM_004342 | 800 | CALD1 | caldesmon 1 | 201616_s_at |
| Stromal-1 | NM_005576 | 4016 | LOXL1 | lysyl oxidase-like 1 | 203570_at |
| Stromal-1 | NM_199511 | 151887 | CCDC80 | coiled-coil domain containing 80 | 225242_s_at |
| Stromal-1 | NM_012098 | 23452 | ANGPTL2 | angiopoietin-like 2 | 213001_at |
| Stromal-1 | NM_002210 | 3685 | ITGAV | integrin, alpha V (vitronectin receptor, alpha polypeptide, antigen CD51) | 202351_at |
| Stromal-1 | NM_000366 | 7168 | TPM1 | tropomyosin 1 (alpha) | 210986_at |
| Stromal-1 | NM_198474 | 283298 | OLFML1 | olfactomedin-like 1 | 217525_at |
| Stromal-1 | NM_001424 | 2013 | EMP2 | epithelial membrane protein 2 | 225078_at |
| Stromal-1 | NM_032575 | 84662 | GLIS2 | GLIS family zinc finger 2 | 223378_at |
| Stromal-1 | NM_007173 | 11098 | PRSS23 | protease, serine, 23 | 226279_at |
| Stromal-1 | NM_001015880 | 9060 | PAPSS2 | 3'-phosphoadenosine 5'-phosphosulfate synthase 2 | 203060_s_at |
| Stromal-1 | NM_015645 | 114902 | C1QTNF5 | C1q and tumor necrosis factor related protein 5 | 223499_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | AK130049 | | | CDNA FLJ26539 fis, clone KDN09310 | 213429_at |
| Stromal-1 | NM_001849 | 1292 | COL6A2 | collagen, type VI, alpha 2 | 209156_s_at |
| Stromal-1 | NM_001014796 | 4921 | DDR2 | discoidin domain receptor family, member 2 | 225442_at |
| Stromal-1 | NM_015463 | 25927 | C2orf32 | chromosome 2 open reading frame 32 | 226751_at |
| Stromal-1 | AK055628 | | ADAM12 | CDNA FLJ31066 fis, clone HSYRA2001153 | 226777_at |
| Stromal-1 | NM_014799 | 9843 | HEPH | hephaestin | 203903_s_at |
| Stromal-1 | NM_004385 | 1462 | CSPG2 | chondroitin sulfate proteoglycan 2 (versican) | 221731_x_at |
| Stromal-1 | NM_152330 | 122786 | FRMD6 | FERM domain containing 6 | 225481_at |
| Stromal-1 | BQ917964 | | PPP4R2 | Transcribed locus | 235733_at |
| Stromal-1 | NM_002615 | 5176 | SERPINF1 | serpin peptidase inhibitor, clade F (alpha-2 antiplasmin, pigment epithelium derived factor), member 1 | 202283_at |
| Stromal-1 | NM_032348 | 54587 | MXRA8 | matrix-remodelling associated 8 | 213422_s_at |
| Stromal-1 | NM_006106 | 10413 | YAP1 | Yes-associated protein 1, 65 kDa | 224894_at |
| Stromal-1 | NM_020182 | 56937 | TMEPAI | transmembrane, prostate androgen induced RNA | 222449_at |
| Stromal-1 | CB999028 | | | Transcribed locus | 226834_at |
| Stromal-1 | NM_001711 | 633 | BGN | biglycan | 201261_x_at |
| Stromal-1 | NM_006902 | 5396 | PRRX1 | paired related homeobox 1 | 226695_at |
| Stromal-1 | NM_000428 | 4053 | LTBP2 | latent transforming growth factor beta binding protein 2 | 204682_at |
| Stromal-1 | NM_004369 | 1293 | COL6A3 | collagen, type VI, alpha 3 | 201438_at |
| Stromal-1 | NM_000393 | 1290 | COL5A2 | collagen, type V, alpha 2 | 221730_at |
| Stromal-1 | NM_015419 | 25878 | MXRA5 | matrix-remodelling associated 5 | 209596_at |
| Stromal-1 | NM_001102 | 87 | ACTN1 | actinin, alpha 1 | 208637_x_at |
| Stromal-1 | NM_000877 | 3554 | IL1R1 | interleukin 1 receptor, type I | 202948_at |
| Stromal-1 | NM_015927 | 7041 | TGFB1I1 | transforming growth factor beta 1 induced transcript 1 | 209651_at |
| Stromal-1 | NM_032772 | 84858 | ZNF503 | zinc finger protein 503 | 227195_at |
| Stromal-1 | NM_020440 | 5738 | PTGFRN | prostaglandin F2 receptor negative regulator | 224937_at |
| Stromal-1 | NM_000138 | 2200 | FBN1 | fibrillin 1 | 202765_s_at |
| Stromal-1 | NM_031442 | 83604 | TMEM47 | transmembrane protein 47 | 209656_s_at |
| Stromal-1 | NM_001734 | 716 | C1S | complement component 1, s subcomponent | 208747_s_at |
| Stromal-1 | NM_002290 | 3910 | LAMA4 | laminin, alpha 4 | 202202_s_at |
| Stromal-1 | CN312045 | | PPP4R2 | Transcribed locus, weakly similar to NP_001013658.1 protein LOC6387873 [*Homo sapiens*] | 222288_at |
| Stromal-1 | NM_000089 | 1278 | COL1A2 | collagen, type I, alpha 2 | 202403_s_at |
| Stromal-1 | NM_004530 | 4313 | MMP2 | matrix metallopeptidase 2 (gelatinase A, 72 kDa gelatinase, 72 kDa type IV collagenase) | 201069_at |
| Stromal-1 | NM_001387 | 1809 | DPYSL3 | dihydropyrimidinase-like 3 | 201431_s_at |
| Stromal-1 | NM_138389 | 92689 | FAM114A1 | family with sequence similarity 114, member A1 | 213455_at |
| Stromal-1 | NM_006670 | 7162 | TPBG | trophoblast glycoprotein | 203476_at |
| Stromal-1 | NM_000304 | 5376 | PMP22 | peripheral myelin protein 22 | 210139_s_at |
| Stromal-1 | NM_002775 | 5654 | HTRA1 | HtrA serine peptidase 1 | 201185_at |
| Stromal-1 | NM_002593 | 5118 | PCOLCE | procollagen C-endopeptidase enhancer | 202465_at |
| Stromal-1 | NM_003118 | 6678 | SPARC | secreted protein, acidic, cysteine-rich (osteonectin) | 212667_at |

TABLE 1-continued

| Signature | GenBank Accession No. | Entrez GeneID | Gene Symbol | Gene Title | Affymetrix Probe Set ID |
|---|---|---|---|---|---|
| Stromal-1 | NM_007085 | 11167 | FSTL1 | follistatin-like 1 | 208782_at |
| Stromal-1 | NM_001080393 | 727936 | | predicted glycosyl-transferase 8 domain containing 4 | 235371_at |
| Stromal-1 | NM_018153 | 84168 | ANTXR1 | anthrax toxin receptor 1 | 224694_at |
| Stromal-1 | NM_001733 | 715 | C1R | complement component 1, r subcomponent | 212067_s_at |
| Stromal-1 | NM_001797 | 1009 | CDH11 | cadherin 11, type 2, OB-cadherin (osteoblast) | 207173_x_at |
| Stromal-1 | NM_016938 | 30008 | EFEMP2 | EGF-containing fibulin-like extracellular matrix protein 2 | 209356_x_at |
| Stromal-2 | NM_014601 | 30846 | EHD2 | EH-domain containing 2 | 45297_at |
| Stromal-2 | NM_017789 | 54910 | SEMA4C | sema domain, immunoglobulin domain (Ig), transmembrane domain (TM) and short cytoplasmic domain, semaphorin 4C | 46665_at |
| Stromal-2 | NM_000484 | 351 | APP | amyloid beta (A4) precursor protein (peptidase nexin-II, Alzheimer disease) | 200602_at |
| Stromal-2 | NM_004684 | 8404 | SPARCL1 | SPARC-like 1 (mast9, hevin) | 200795_at |
| Stromal-2 | NM_002291 | 3912 | LAMB1 | laminin, beta 1 | 201505_at |
| Stromal-2 | NM_000210 | 3655 | ITGA6 | integrin, alpha 6 | 201656_at |
| Stromal-2 | NM_000552 | 7450 | VWF | von Willebrand factor | 202112_at |
| Stromal-2 | NM_001233 | 858 | CAV2 | caveolin 2 | 203323_at |
| Stromal-2 | NM_006404 | 10544 | PROCR | protein C receptor, endothelial (EPCR) | 203650_at |
| Stromal-2 | NM_000609 | 6387 | CXCL12 | chemokine (C-X-C motif) ligand 12 (stromal cell-derived factor 1) | 203666_at |
| Stromal-2 | NM_002253 | 3791 | KDR | kinase insert domain receptor (a type III receptor tyrosine kinase) | 203934_at |
| Stromal-2 | NM_001442 | 2167 | FABP4 | fatty acid binding protein 4, adipocyte | 203980_at |
| Stromal-2 | NM_016315 | 51454 | GULP1 | GULP, engulfment adaptor PTB domain containing 1 | 204237_at |
| Stromal-2 | NM_006307 | 8406 | SRPX | sushi-repeat-containing protein, X-linked | 204955_at |
| Stromal-2 | NM_000163 | 2690 | GHR | growth hormone receptor | 205498_at |
| Stromal-2 | NM_000950 | 5638 | PRRG1 | proline rich Gla (G-carboxyglutamic acid) 1 | 205618_at |
| Stromal-2 | NM_002666 | 5346 | PLIN | perilipin | 205913_at |
| Stromal-2 | NM_000459 | 7010 | TEK | TEK tyrosine kinase, endothelial (venous malformations, multiple cutaneous and mucosal) | 206702_at |
| Stromal-2 | NM_004797 | 9370 | ADIPOQ | adiponectin, C1Q and collagen domain containing | 207175_at |
| Stromal-2 | NM_000442 | 5175 | PECAM1 | platelet/endothelial cell adhesion molecule (CD31 antigen) | 208981_at |
| Stromal-2 | NM_198098 | 358 | AQP1 | aquaporin 1 (Colton blood group) | 209047_at |
| Stromal-2 | NM_021005 | 7026 | NR2F2 | nuclear receptor subfamily 2, group F, member 2 | 209120_at |
| Stromal-2 | NM_014220 | 4071 | TM4SF1 | transmembrane 4 L six family member 1 | 209386_at |
| Stromal-2 | NM_001001549 | 2887 | GRB10 | growth factor receptor-bound protein 10 | 209409_at |
| Stromal-2 | NM_006108 | 10418 | SPON1 | spondin 1, extracellular matrix protein | 209436_at |
| Stromal-2 | NM_001003679 | 3953 | LEPR | leptin receptor | 209894_at |
| Stromal-2 | NM_000599 | 3488 | IGFBP5 | insulin-like growth factor binding protein 5 | 211959_at |
| Stromal-2 | NM_001753 | 857 | CAV1 | caveolin 1, caveolae protein, 22 kDa | 212097_at |
| Stromal-2 | NM_005841 | 10252 | SPRY1 | sprouty homolog 1, antagonist of FGF signaling (*Drosophila*) | 212558_at |

TABLE 1-continued

| Signature | GenBank Accession No. | Entrez GeneID | Gene Symbol | Gene Title | Affymetrix Probe Set ID |
|---|---|---|---|---|---|
| Stromal-2 | NM_015345 | 23500 | DAAM2 | dishevelled associated activator of morphogenesis 2 | 212793_at |
| Stromal-2 | NM_015234 | 221395 | GPR116 | G protein-coupled receptor 116 | 212950_at |
| Stromal-2 | NM_006108 | 10418 | SPON1 | spondin 1, extracellular matrix protein | 213993_at |
| Stromal-2 | NM_016215 | 51162 | EGFL7 | EGF-like-domain, multiple 7 | 218825_at |
| Stromal-2 | NM_022481 | 64411 | CENTD3 | centaurin, delta 3 | 218950_at |
| Stromal-2 | XM_371262 | 64123 | ELTD1 | EGF, latrophilin and seven transmembrane domain containing 1 | 219134_at |
| Stromal-2 | NM_016563 | 51285 | RASL12 | RAS-like, family 12 | 219167_at |
| Stromal-2 | NM_006094 | 10395 | DLC1 | deleted in liver cancer | 224822_at |
| Stromal-2 | NM_019035 | 54510 | PCDH18 | protocadherin 18 | 225975_at |
| Stromal-2 | NM_019055 | 54538 | ROBO4 | roundabout homolog 4, magic roundabout (*Drosophila*) | 226028_at |
| Stromal-2 | NM_002207 | 3680 | ITGA9 | integrin, alpha 9 | 227297_at |
| Stromal-2 | XM_930608 | 641700 | ECSM2 | endothelial cell-specific molecule 2 | 227779_at |
| Stromal-2 | XM_037493 | 85358 | SHANK3 | SH3 and multiple ankyrin repeat domains 3 | 227923_at |
| Stromal-2 | NM_052954 | 116159 | CYYR1 | cysteine/tyrosine-rich 1 | 228665_at |
| Stromal-2 | NM_002837 | 5787 | PTPRB | protein tyrosine phosphatase, receptor type, B | 230250_at |
| Stromal-2 | NM_019558 | 3234 | HOXD8 | homeobox D8 | 231906_at |
| Stromal-2 | NM_001442 | 2167 | FABP4 | fatty acid binding protein 4, adipocyte | 235978_at |
| Stromal-2 | NM_024756 | 79812 | MMRN2 | multimerin 2 | 236262_at |
| Stromal-2 | BQ897248 | | | Transcribed locus | 242680_at |
| Stromal-2 | NM_020663 | 57381 | RHOJ | ras homolog gene family, member J | 243481_at |
| Stromal-2 | AK091419 | | | CDNA FLJ34100 fis, clone FCBBF3007597 | 1558397_at |
| Stromal-2 | NM_015719 | 50509 | COL5A3 | collagen, type V, alpha 3 | 52255_s_at |
| Stromal-2 | NM_012072 | 22918 | CD93 | CD93 molecule | 202878_s_at |
| Stromal-2 | NM_000300 | 5320 | PLA2G2A | phospholipase A2, group IIA (platelets, synovial fluid) | 203649_s_at |
| Stromal-2 | NM_019105 | 7148 | TNXB | tenascin XB | 206093_x_at |
| Stromal-2 | NM_030754 | 6289 | SAA2 | serum amyloid A2 | 208607_s_at |
| Stromal-2 | NM_019105 | 7148 | TNXB | tenascin XB | 208609_s_at |
| Stromal-2 | NM_014220 | 4071 | TM4SF1 | transmembrane 4 L six family member 1 | 209387_s_at |
| Stromal-2 | NM_000668 | 125 | ADH1B | alcohol dehydrogenase IB (class I), beta polypeptide | 209612_s_at |
| Stromal-2 | NM_000668 | 125 | ADH1B | alcohol dehydrogenase IB (class I), beta polypeptide | 209613_s_at |
| Stromal-2 | NM_001354 | 1646 | AKR1C2 | aldo-keto reductase family 1, member C2 (dihydrodiol dehydrogenase 2; bile acid binding protein; 3-alpha hydroxysteroid dehydrogenase, type III) | 209699_x_at |
| Stromal-2 | NM_001032281 | 7035 | TFPI | tissue factor pathway inhibitor (lipoprotein-associated coagulation inhibitor) | 210664_s_at |
| Stromal-2 | NM_001001924 | 57509 | MTUS1 | mitochondrial tumor suppressor 1 | 212096_s_at |
| Stromal-2 | NM_019105 | 7148 | TNXB | tenascin XB | 213451_x_at |
| Stromal-2 | NM_004449 | 2078 | ERG | v-ets erythroblastosis virus E26 oncogene homolog (avian) | 213541_s_at |
| Stromal-2 | NM_018407 | 55353 | LAPTM4B | lysosomal associated protein transmembrane 4 beta | 214039_s_at |
| Stromal-2 | NM_000331 | 6288 | SAA1 | serum amyloid A1 | 214456_x_at |
| Stromal-2 | NM_019105 | 7148 | TNXB | tenascin XB | 216333_x_at |
| Stromal-2 | NM_001034954 | 10580 | SORBS1 | sorbin and SH3 domain containing 1 | 218087_s_at |
| Stromal-2 | NM_017734 | 54873 | PALMD | palmdelphin | 218736_s_at |
| Stromal-2 | NM_024756 | 79812 | MMRN2 | multimerin 2 | 219091_s_at |

TABLE 1-continued

| Signature | GenBank Accession No. | Entrez GeneID | Gene Symbol | Gene Title | Affymetrix Probe Set ID |
|---|---|---|---|---|---|
| Stromal-2 | NM_006744 | 5950 | RBP4 | retinol binding protein 4, plasma | 219140_s_at |
| Stromal-2 | NM_001034954 | 10580 | SORBS1 | sorbin and SH3 domain containing 1 | 222513_s_at |

The DLBCL survival predictors of the invention were generated using expression data and methods described in Examples 1 and 2, below. The first bivariate survival predictor incorporates the GCB and stromal-1 gene expression signatures. Fitting the Cox proportional hazards model to the gene expression data obtained from these two signatures resulted in a bivariate model survival predictor score calculated using the following generalized equation:

Bivariate DLBCL survival predictor score=$A-[(x)*$(GCB signature value)]$-[(y)*$(stromal-1 signature value)].

In this equation, A is an offset term, while (x) and (y) are scale factors. The GCB signature value and the stromal-1 signature value can correspond to the average of the expression levels of all genes in the GCB signature and the stromal-1 signature, respectively. A lower survival predictor score indicates a more favorable survival outcome, and a higher survival predictor score indicates a less favorable survival outcome for the subject.

The bivariate survival predictor was refined into a multivariate survival predictor that incorporates GCB, stromal-1, and stromal-2 gene expression signatures. Fitting the Cox proportional hazards model to the gene expression data obtained from these three signatures resulted in a multivariate model survival predictor score calculated using the following generalized equation:

General multivariate DLBCL survival predictor score=$A-[(x)*$(GCB signature value)]$-[(y)*$(stromal-1 signature value)]$+[(z)*$(stromal-2 signature value)].

In this equation, A is an offset term, while (x), (y), and (z) are scale factors. The GCB signature value, the stromal-1 signature value, and the stromal-2 signature value can correspond to the average of the expression levels of all genes in the GCB signature, the stromal-1 signature, and the stromal-2 signature, respectively. A lower survival predictor score indicates a more favorable survival outcome and a higher survival predictor score indicates a less favorable survival outcome for the subject.

In one embodiment, the invention provides the following multivariate survival predictor equation:

Multivariate DLBCL survival predictor score=8.11$-$[0.419*(GCB signature value)]$-$[1.015*(stromal-1 signature value)]$+$[0.675*(stromal-2 signature value)]

In this equation, a lower survival predictor score indicates a more favorable survival outcome, and a higher survival predictor score indicates a poorer survival outcome for the subject.

In other embodiments of the multivariate DLBCL survival predictor score equation, the offset term (A) or (8.11) can be varied without affecting the equation's usefulness in predicting clinical outcome. Scale factors (x), (y), and (z) can also be varied, individually or in combination. For example, scale factor (x) can be from about 0.200 or more, from about 0.225 or more, from about 0.250 or more, from about 0.275 or more, from about 0.300, from about 0.325 or more, from about 0.350 or more, from about 0.375 or more, or from about 0.400 or more. Alternatively, or in addition, scale factor (x) can be about 0.625 or less, about 0.600 or less, about 0.575 or less, about 0.550 or less, about 0.525 or less, about 0.500 or less, about 0.475 or less, about 0.450 or less, or about 0.425 or less. Thus, scale factor (z) can be one that is bounded by any two of the previous endpoints. For example scale factor (x) can be a value from 0.200-0.625, from 0.350-0.550, from 0.350-0.475, or from 0.400-0.425. Similarly, scale factor (y) can be from about 0.800 or more, from about 0.825 or more, from about 0.850 or more, from about 0.875 or more, from about 0.900 or more, from about 0.925 or more, from about 0.950 or more, from about 0.975 or more, or from about 1.000 or more. Alternatively, or in addition, scale factor (y) can be, e.g., about 1.250 or less, e.g., about 1.225 or less, about 1.200, about 1.175 or less, about 1.150 or less, about 1.125 or less, about 1.100 or less, about 1.075 or less, about 1.050 or less, or about 1.025 or less. Thus, scale factor (y) can be one that is bounded by any two of the previous endpoints. For example, scale factor (y) can be a value from 0.800-1.250, a value from 0.950-1.1025, a value from 0.950-1.200 or a value from 1.000-1.025. Also similarly, scale factor (z) can be from about 0.450 or more, about 0.475 or more, about 0.500 or more, about 0.525 or more, about 0.550 or more, about 0.575 or more, about 0.600 or more, about 0.625 or more, or about 0.650 or more. Alternatively, or in addition, scale factor (z) can be, e.g., about 0.900 or less, e.g., about 0.875 or less, about 0.850, about 0.825 or less, about 0.800 or less, about 0.775 or less, about 0.750 or less, or about 0.725 or less. Thus, scale factor (z) can be one that is bounded by any two of the previous endpoints. For example, scale factor (z) can be a value from 0.450-0.900, any value from 0.650-0.725, any value from 0.625-0.775 or any value from 0.650-0.700.

Furthermore, the invention includes any set of scale factors (x), (y), and (z) in conjunction in the general multivariate DLBCL survival predictor score that creates a function that is monotonically related to a multivariate DLBCL survival predictor score equation using any combination of the foregoing specified scale factor (x), (y), and (z) values.

In some embodiments of the invention, a survival predictor score can be calculated using fewer than all of the gene components of the GCB signature, the stromal-1 signature, and/or the stromal-2 signature listed in Table 1. For example, the survival prediction equations disclosed herein can be calculated using mathematical combinations of the expressions of 98% (38), 95% (37), 93% (36), or 90% (35) of the genes listed in Table 1 for the GCB signature, about 99% (about 280), about 98% (about 277), 97% (about 275), about 96% (about 272), about 95% (about 270), about 94% (about 266), about 93% (about 263), about 92% (about 260), about 91% (about 257), or about 90% (about 255) of the genes listed in Table 1 for the stromal-1 signature, and/or 99% (71), 97% (70), 96% (69), 95% (68) 93% (67), 92% (66), or 90% (65) of the genes listed in Table 1 for the stromal-2 signature (instead of using all of the genes corresponding to a gene signature in Table 1 to calculate the GCB signature value, the stromal-1 signature value, and/or stromal-2 signature value, respectively). In other embodiments, the survival prediction equations disclosed herein can be calculated using mathematical combinations of the expressions of 88% (34 genes), 85% (33 genes), 82% (32 genes), 80% (31 genes) of the genes listed in Table 1 for the GCB signature, about 89% (about 252), about 88% (about 249), about 87% (about 246), about 86% (about 243), about 85% (about 241), about 84% (about 238), about 83% (about 235), about 82% (about 232), about 81% (about 229), or about 80% (about 226) of the genes listed in Table 1 for the stromal-1 signature, and/or 89% (64), 88% (63), 86% (62), 85% (61), 83% (60), 82% (59) or 80% (58) of the genes listed in Table 1 for the stromal-2 signature (instead of using all of the genes corresponding to a gene signature in Table 1 to calculate the GCB signature value, the stromal-1 signature value, and/or stromal-2 signature value, respectively).

The invention also provides a method of using a DLBCL survival predictor score to predict the probability of a survival outcome beyond an amount of time t following treatment for DLBCL. The method includes calculating the probability of a survival outcome for a subject using the following general equation:

$$P(SO)=SO_0(t)^{(exp((s)*(survival\ predictor\ score)))}$$

In this equation, P(SO) is the subject's probability of the survival outcome beyond time t following treatment for DLBCL, $SO_0(t)$ is the probability of survival outcome, which corresponds to the largest time value smaller than t in a survival outcome curve, and (s) is a scale factor. Treatment for DLBCL can include chemotherapy and the administration of Rituximab. A survival curve can be calculated using statistical methods, such as the Cox Proportional Hazard Model. Additional information regarding survival outcome curves is set forth in Lawless, *Statistical Models and Methods for Lifetime Data*, John Wiley and Sons (New York 1982) and Kalbfleisch et al., *Biometrika*, 60: 267-79 (1973).

In one embodiment, the method of the invention includes calculating the probability of overall survival for a subject beyond an amount of time t following treatment for DLBCL. The method includes calculating the probability of a survival outcome for a subject using the following general equation:

$$P(OS)=SO_0(t)^{(exp(survival\ predictor\ score))}$$

In the equation, P(OS) is the subject's probability of overall survival beyond time t following treatment for DLBCL, $SO_0(t)$ is the curve probability of survival outcome, which corresponds to the largest time value in a survival curve which is smaller than t, and the general equation scale factor (s)=1. Treatment for DLBCL can include chemotherapy alone or in combination with the administration of Rituximab (R-CHOP).

In another embodiment, the method of the invention includes calculating the probability of progression-free survival for a subject beyond an amount of time t following treatment for DLBCL. The method includes calculating the probability of a survival outcome for a subject using the following general equation:

$$P(PFS)=SO_0(t)^{(exp(0.976*(survival\ predictor\ score)))}$$

In this equation, P(PFS) is the subject's probability of progression-free survival beyond time t following treatment for DLBCL, $SO_0(t)$ is the curve probability of progression-free survival, which corresponds to the largest time value in a survival curve which is smaller than t, and the general equation scale factor (s)=0.976. The treatment for DLBCL can include chemotherapy alone or in combination with the administration of Rituximab (R-CHOP).

The foregoing equations for P(OS) and P(PFS) were generated by maximizing the partial likelihoods of the Cox proportional hazards model within the LLMPP CHOP data described below in Examples 1 and 2. Separate single variable Cox proportional hazards models were considered for overall survival P(OS) and for progression free survival P(PFS) based on this model score formulation. The single variable scale factor (1.0 for overall survival and 0.997 for progression free survival) were generated for each model by maximization of the partial likelihoods within the R-CHOP patients described below in Examples 1 and 2.

In other embodiments, the scale factor in the foregoing P(PFS) can be varied such that (instead of 0.976) scale factor (s) is a value between 0.970 and 0.980, e.g. 0.971, 0.972, 0.973, 0.973, 0.974, 0.975, 0.977, 0.978, and 0.979.

The invention also provides a method of selecting a subject for antiangiogenic therapy of DLBCL based on the subject's high relative expression of stromal-2 signature genes. As discussed more fully below in Example 4, the stromal-2 signature includes a number of genes whose expression or gene products are related to angiogenesis. Thus, high relative expression of stromal-2 signature genes in DLBCL can be indicative of high angiogenic activity. Moreover, high relative expression of stromal-2 signature genes can be related to the heavy infiltration of some DLBCL tumors with myeloid lineage cells. Accordingly, subjects with high relative expression of stromal-2 signature genes are good candidates for treatment with antiangiogenic therapy, either alone or in combination with other anti-oncogenic therapies. Furthermore, as also discussed more fully in Example 4, a stromal score, which was obtained by subtracting the stromal-1 signature value from the stromal-2 signature value, was observed to correlate with high tumor blood vessel density.

In this regard, the antiangiogenic monoclonal antibody to vascular endothelial growth factor bevacizumab has been clinically tested in patients with DLBCL (Ganjoo et al., *Leuk. Lymphoma*, 47: 998-1005 (2006)). Other antiangiogenic therapies can include small molecule inhibitors of SDF-1 receptor, such as CXCR4 (Petit et al., *Trends Immunol.*, 28: 299-307 (2007). Still another example of an antiangiogenic therapy can include blocking antibodies to the myeloid lineage cell marker CTGF, which has been implicated in angiogenesis. Moreover, anti-CTGF antibodies have been shown to have anti-cancer activity in pre-clinical models of cancer (Aikawa et al., *Mol. Cancer Ther.*, 5: 1108-16 (2006)).

In one embodiment, the method of the invention for selecting a subject for antiangiogenic therapy includes obtaining a gene expression profile from a DLBCL biopsy from the subject. The subject's stromal-2 signature value is determined. The subject's stromal-2 signature value is then compared to a standard stromal-2 value. A standard stromal-2 value corresponds to the average of multiple stromal-2 signature values in DLBCL biopsy samples from a plurality of randomly selected subjects with DLBCL, e.g., more than 10, 20, 30, 40, 50, 60, 70, 80, 90, 100, 150, 200, or 250 randomly selected subjects with DLBCL. If the subject's stromal-2 signature value is significantly higher than the standard stromal-2 value, then the subject can be treated with anti-angiogenic therapy.

In another embodiment, the method of the invention for selecting a subject for anti-angiogenic therapy includes obtaining a gene expression profile from a DLBCL biopsy from the subject. The subject's stromal 1 signature value and stromal-2 signature value are determined. The stromal-1 signature value is then subtracted from the stromal-2 signature value to obtain a stromal score. The subject's stromal score is then compared to a standard stromal score. A standard stromal score corresponds to the average of multiple stromal scores (each stromal score=[stromal-2 signature value])–[stromal-1 signature value]) derived from DLBCL biopsy samples from a plurality of randomly selected subjects with DLBCL, e.g., more than 10, 20, 30, 40, 50, 60, 70, 80, 90, 100, 150, 200, or 250 randomly selected subjects with DLBCL. If the subject's stromal score is significantly higher than the standard stromal score, then the subject can be treated with anti-angiogenic therapy.

The invention further provides a targeted array that can be used to detect the expression levels of all or most of the genes in a germinal center B cell gene (GCB) expression signature, a stromal-1 gene expression signature, and/or a stromal-2 gene expression signature. A targeted array, as used herein, is an array directed to a limited set of genes and thus differs from a whole genome array. The targeted array of the invention can include probes for fewer than 20,000 genes, fewer than 15,000 genes, fewer than 10,000 genes, fewer than 8,000 genes, fewer than 7,000 genes, fewer than 6,000 genes, fewer than 5,000 genes, or fewer than 4,000 genes. Generally, the targeted array includes probes for at least 80% of the genes in a germinal center B cell gene (GCB) expression signature, a stromal-1 gene expression signature, and/or a stromal-2 gene expression signature. The targeted arrays of the invention can be used, for example, to detect expression levels for use in the methods described herein.

The invention provides a targeted array that includes probes for all of the genes in the stromal-1 gene expression signature. The invention also provides a targeted array that includes probes for all of the genes in the stromal-2 gene expression signature. Additionally, the invention provides a targeted array that includes probes for all of the genes in the stromal-1 gene expression signature and all of the genes in the stromal-2 gene expression signature. Moreover, the invention provides a targeted array that includes probes for all of the genes, in the stromal-1 gene expression signature, all of the genes in the stromal-2 gene expression signature, and all of the genes in the GCB signature.

In certain embodiments, the arrays of the invention can include 98% (38), 95% (37), 93% (36), or 90% (35) of the genes listed in Table 1 for the GCB signature, about 99% (about 280), about 98% (about 277), 97% (about 275), about 96% (about 272), about 95% (about 270), about 94% (about 266), about 93% (about 263), about 92% (about 260), about 91% (about 257), or about 90% (about 255) of the genes listed in Table 1 for the stromal-1 signature, and/or 99% (71), 97% (70), 96% (69), 95% (68) 93% (67), 92% (66), or 90% (65) of the genes listed in Table 1 for the stromal-2 signature (instead of all of the genes listed in Table 1 for the GCB signature average, the stromal-1 signature average, and/or stromal-2 signature average, respectively). In certain embodiments, the arrays of the invention can include 88% (34 genes), 85% (33 genes), 82% (32 genes), 80% (31 genes) of the genes listed in Table 1 for the GCB signature, about 89% (about 252), about 88% (about 249), about 87% (about 246), about 86% (about 243), about 85% (about 241), about 84% (about 238), about 83% (about 235), about 82% (about 232), about 81% (about 229), or about 80% (about 226) of the genes listed in Table 1 for the stromal-1 signature, and/or 89% (64), 88% (63), 86% (62), 85% (61), 83% (60), 82% (59) or 80% (58) of the genes listed in Table 1 for the stromal-2 signature (instead of all of the genes listed in Table 1 for the GCB signature average, the stromal-1 signature average, and/or stromal-2 signature average, respectively).

The following examples further illustrate the invention but, of course, should not be construed as in any way limiting its scope.

Example 1

This example demonstrates that significant differences were found between the survival outcomes for R-CHOP treated ABC DLBCL and GCB DLBCL patients and that survival outcome correlated with three prognostic gene expression signatures.

Pre-treatment tumor biopsy specimens and clinical data were obtained from 414 patients with de novo DLBCL treated at 10 institutions in North America and Europe and studied according to a protocol approved by the National Cancer Institute's Institutional Review Board. Patients included in a "LLMP CHOP cohort" of 181 patients were treated with anthracycline-based combinations, most often cyclophosphamide, doxorubicin, vincristine, and prednisone (CHOP) or similar regimens, as previously described (Rosenwald et al., *N. Engl. J. Med.*, 346: 1937-47 (2002)). The remaining 233 patients constituted an R-CHOP cohort that received similar chemotherapy plus Rituximab. The median follow-up in the R-CHOP cohort was 2.1 years (2.8 years for survivors). A panel of expert hematopathologists confirmed the diagnosis of DLBCL using current WHO criteria. Additional clinical patient characteristics for the R-CHOP cohort are described in Table 2. Additional analysis used a second "MMMNLP CHOP" cohort of 177 patients studied by the Molecular Mechanisms of Non-Hodgkin's Lymphoma Network Project (Hummel et al., *N. Engl. J. Med.*, 354: 2419-30 (2006)).

TABLE 2

Clinical characteristics of DLBCL patients treated with R-CHOP

| Characteristic | % Total (N = 233) | % Germinal center B cell-like DLBCL (N = 107) | % Activated B cell-like DLBCL (N = 93) | % Unclassified DLBCL (N = 33) | P-value |
|---|---|---|---|---|---|
| Age > 60 yr | 52 | 47 | 63 | 39 | 0.02 |
| Ann Arbor stage > II | 54 | 48 | 62 | 50 | 0.06 |
| Lactate Dehydrogenase > 1x Normal | 48 | 43 | 58 | 41 | 0.06 |
| No. of extranodal sites > 1 | 15 | 14 | 15 | 14 | 0.8 |

TABLE 2-continued

Clinical characteristics of DLBCL patients treated with R-CHOP

| Characteristic | % Total (N = 233) | % Germinal center B cell-like DLBCL (N = 107) | % Activated B cell-like DLBCL (N = 93) | % Unclassified DLBCL (N = 33) | P-value |
|---|---|---|---|---|---|
| Eastern Cooperative Oncology Group (ECOG) performance status | 25 | 17 | 33 | 27 | 0.02 |
| International Prognostic Index (IPI) Score | | | | | <0.001 |
| 0 or 1 | 41 | 55 | 21 | 50 | |
| 2 or 3 | 46 | 33 | 63 | 38 | |
| 4 or 5 | 13 | 12 | 15 | 12 | |
| Revised IPI Score | | | | | <0.001 |
| 0 | 19 | 27 | 5 | 28 | |
| 1 or 2 | 56 | 52 | 64 | 48 | |
| 3-5 | 25 | 21 | 31 | 24 | |

Gene expression profiling was performed using Affymetrix U133+ 2.0 microarrays. Gene expression profiling data are available through the National Center for Biotechnology Information web site as described in Lenz et al., *New Engl. J. Med*, 359: 2313-23 (2008), at page 2314. All gene expression array data were normalized using MAS 5.0 software, and were log 2 transformed. To account for technical differences in the microarray processing between the R-CHOP cohort data and the LLMPP CHOP cohort data, the expression values of each gene in the R-CHOP cohort data were adjusted so that its median matched the median of the LLMPP CHOP data.

Gene expression signature identification and survival predictor model development were based solely on the data from the LLMPP CHOP training set. No prior survival analysis or subgroup analysis was performed with the test sets (MMMLNP CHOP and R-CHOP cohorts). The Cox model was used to identify genes associated with survival in the CHOP training set and to build multivariate survival models. The models and their associated scaling coefficients were fixed based on the CHOP training set and then evaluated on the test sets. The P-values of survival effects of continuous variables such as gene expression or signature expression were calculated with the Cox likelihood ratio test. The significance of survival effects based on discrete variables such as lymphoma subtype or International Prognostic Index (IPI) was calculated using the log rank test. Validation P-values presented are one-sided in the direction observed in the training set. All other P-values were two sided. Survival curves were estimated using the Kaplan-Meier method.

All aspects of gene expression signature identification and survival predictor model development were based solely on the data from the CHOP training set. No prior survival analysis or subgroup analysis was performed with the test sets (MMMLNP CHOP and R-CHOP cohorts). The Cox model was used to identify genes associated with survival in the CHOP training set and to build multivariate survival models. The models and their associated scale factors were fixed based on the CHOP training set, and then evaluated on the test sets.

Figure 1B:
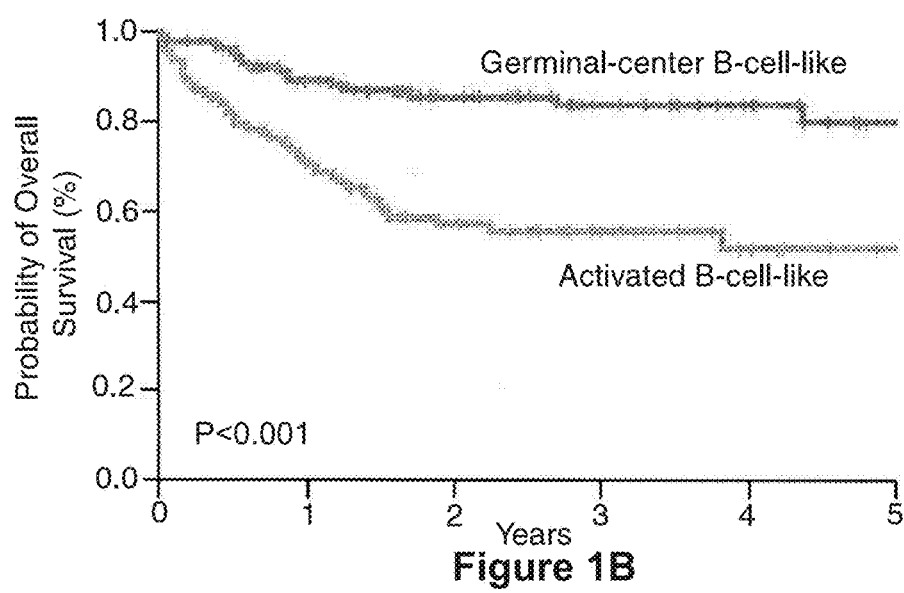
FIG. 1B a Kaplan-Meier estimates plot depicting the probability of overall survival versus time (in years) of patients with GCB DLBCL and ABC DLBCL. The plot indicates that GCB patients have a more favorable, i.e., higher probability, of overall survival than ABC patients for at least five years following R-CHOP therapy.
Figure 6A:
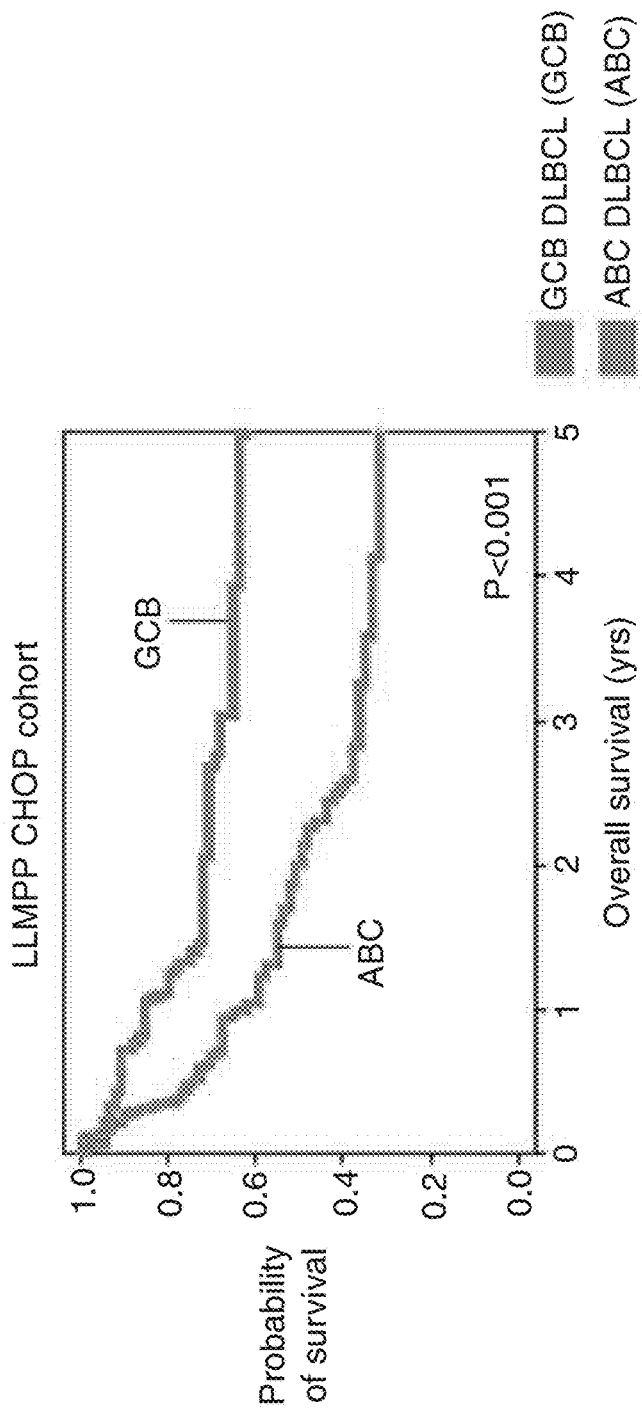
FIG. 6A is a Kaplan-Meier estimates plot depicting the probability of overall survival versus time (in years) for "LLMPP CHOP" patients with DLBCL following therapy. The plot indicates that in this cohort, patients with GCB DLBCL show significantly superior overall survival compared to patients with ABC DLBCL following CHOP therapy.
Figure 6B:
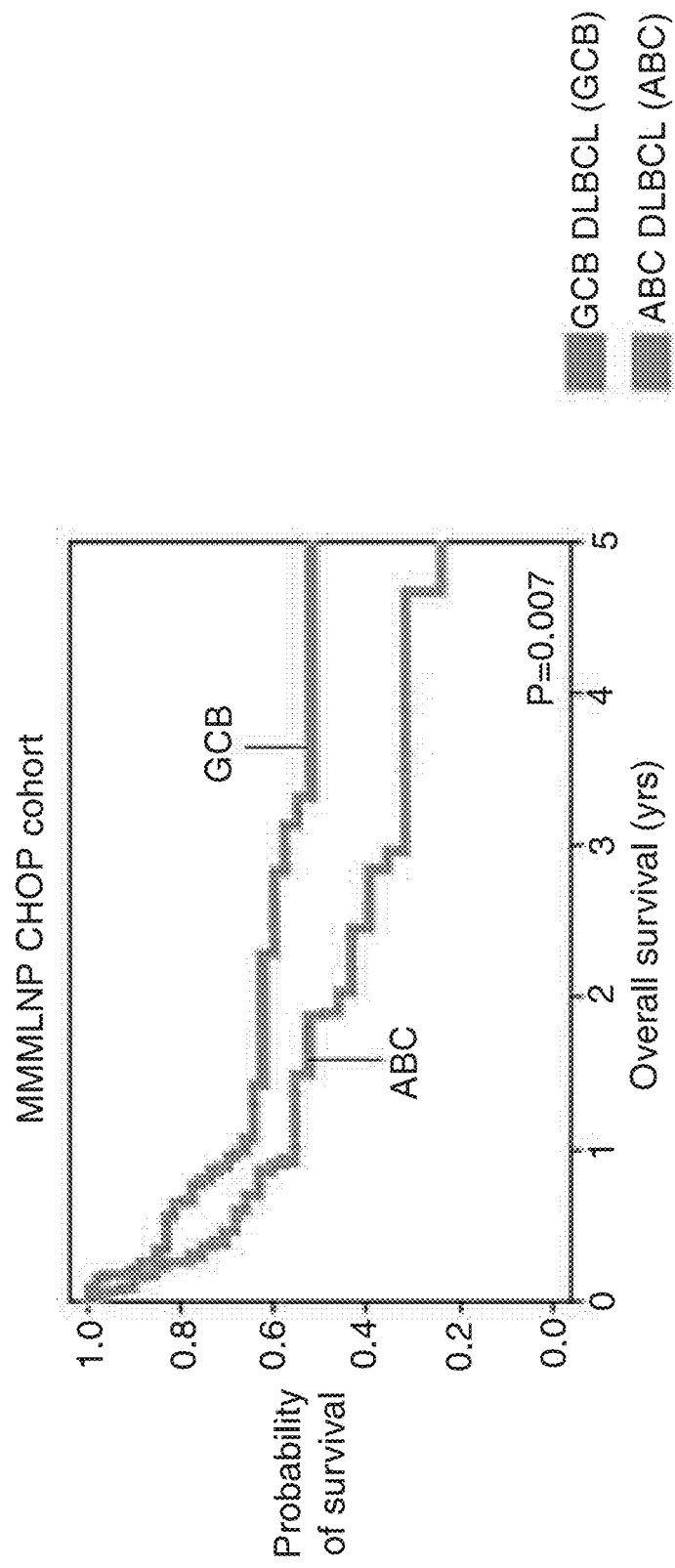
FIG. 6B is a is a Kaplan-Meier estimates plot depicting depicting the probability of overall survival versus time (in years) for "MMMLNP CHOP" patients with DLBCL following therapy. In this cohort, patients with GCB DLBCL show significantly superior overall survival compared to patients with ABC DLBCL following CHOP therapy.

Since ABC and GCB DLBCL subtypes have distinct overall survival rates with CHOP chemotherapy (Rosenwald et al., *N. Engl. J. Med.*, 346: 1937-47 (2002); Alizadeh et al., *Nature*, 403:503-11(2000); Hummel et al., *N. Engl. J. Med.*, 354:2419-30 (2006); Monti, *Blood*, 105:1851-61(2005)), whether this distinction remains prognostically significant among patients treated with R-CHOP was tested (Coiffier et al, *N. Engl. J. Med.*, 346: 235-42 (2002)). Gene expression profiles were determined for pre-treatment biopsy samples from a "training set" of 181 patients treated with CHOP or CHOP-like chemotherapy alone and from a "test set" of 233 patients treated with R-CHOP. The patients in these two cohorts were comparable with respect to age range and distribution of the clinical prognostic variables that constitute the International Prognostic Index (IPI) (Table 2). In the R-CHOP cohort, patients with GCB DLBCL had better survival rates than those with ABC DLBCL. Specifically, R-CHOP treated GCB DLBCL and ABC DLBCL patients had 3-year overall survival rates of 84% and 56%, respectively, and 3-year progression-free survival rates of 74% and 40%, respectively (FIGS. 1A and 1B). In the CHOP training set, and in a second "MMMLMP" CHOP cohort (Hummel et al., supra), the overall survival rates for ABC DLBCL and GCB DLBCL were lower than in the R-CHOP cohort (FIG. 6). Multivariate analysis indicated that the relative benefit (i.e., change in survival outcome) due to R-CHOP therapy (as compared to CHOP) was not significantly different between ABC and GCB DLBCL.

Figure 7:
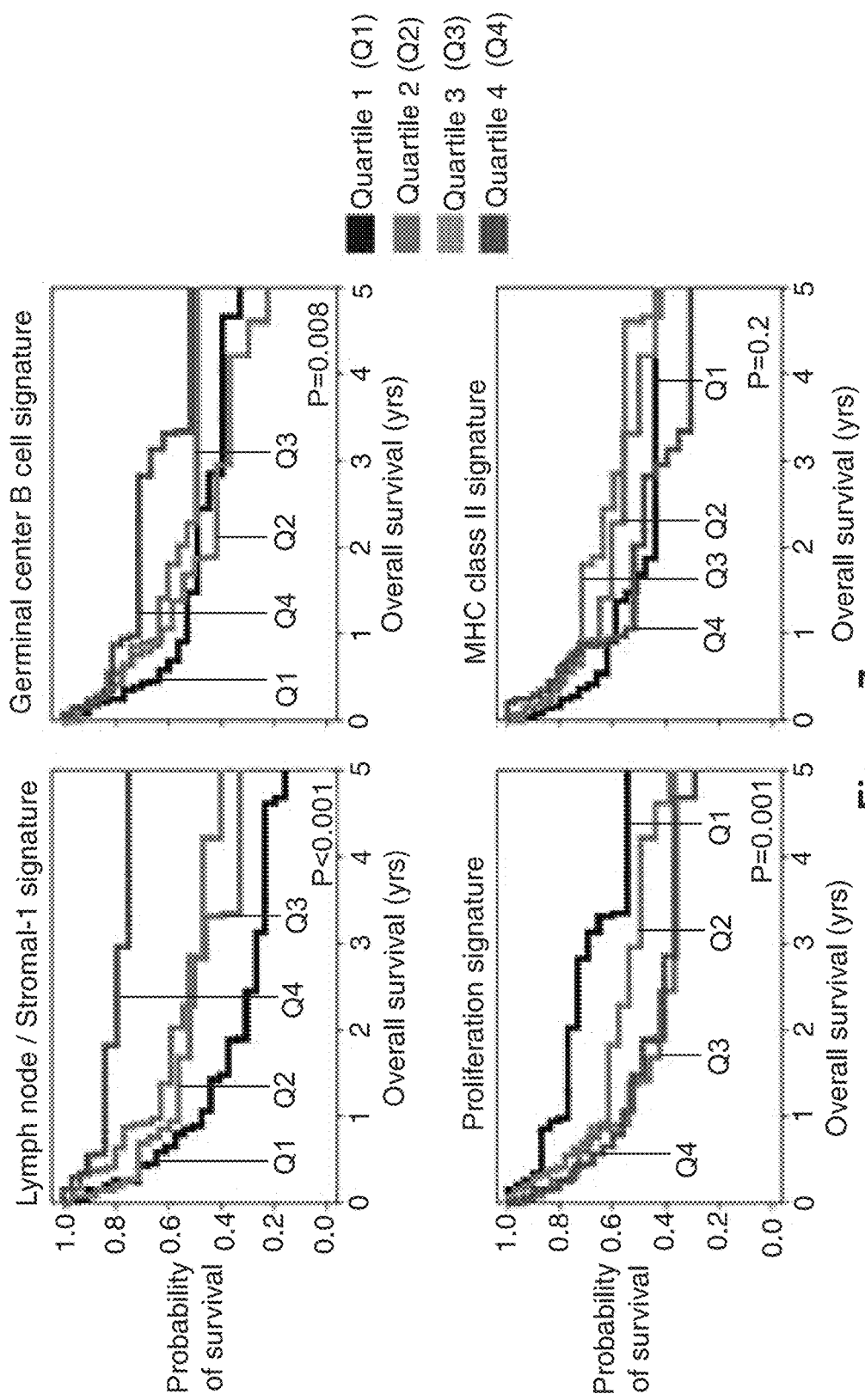
FIG. 7 is a set of four Kaplan-Meier estimates plots depicting the probability of overall survival versus time (in years) in a "MMMLNP CHOP" cohort. Each of the four plots correlates the probability of overall survival with the lymph node/stromal-1, germinal center B cell, proliferation, or MHC class II gene expression signature, respectively. Moreover, in each plot, the average expression of the signature genes in each biopsy sample was used to rank cases and divide the cohort into quartile groups as indicated.

Four gene expression signatures have been previously shown to have prognostic significance in DLBCL patients treated with CHOP (Rosenwald et al., supra). Of these, the GCB signature and lymph node signature were associated with favorable survival, and the proliferation signature was associated with inferior survival within the CHOP training set, in the MMMLNP CHOP cohort (see the corresponding signature panels in FIG. 7), and in the R-CHOP cohort (see corresponding signature panels in FIG. 1C). Thus, the biological differences among DLBCL tumors reflected by these three signatures remain prognostically important in Rituximab treated patients, even though Rituximab treatment generally improved survival in DLBCL.

Figure 1C:
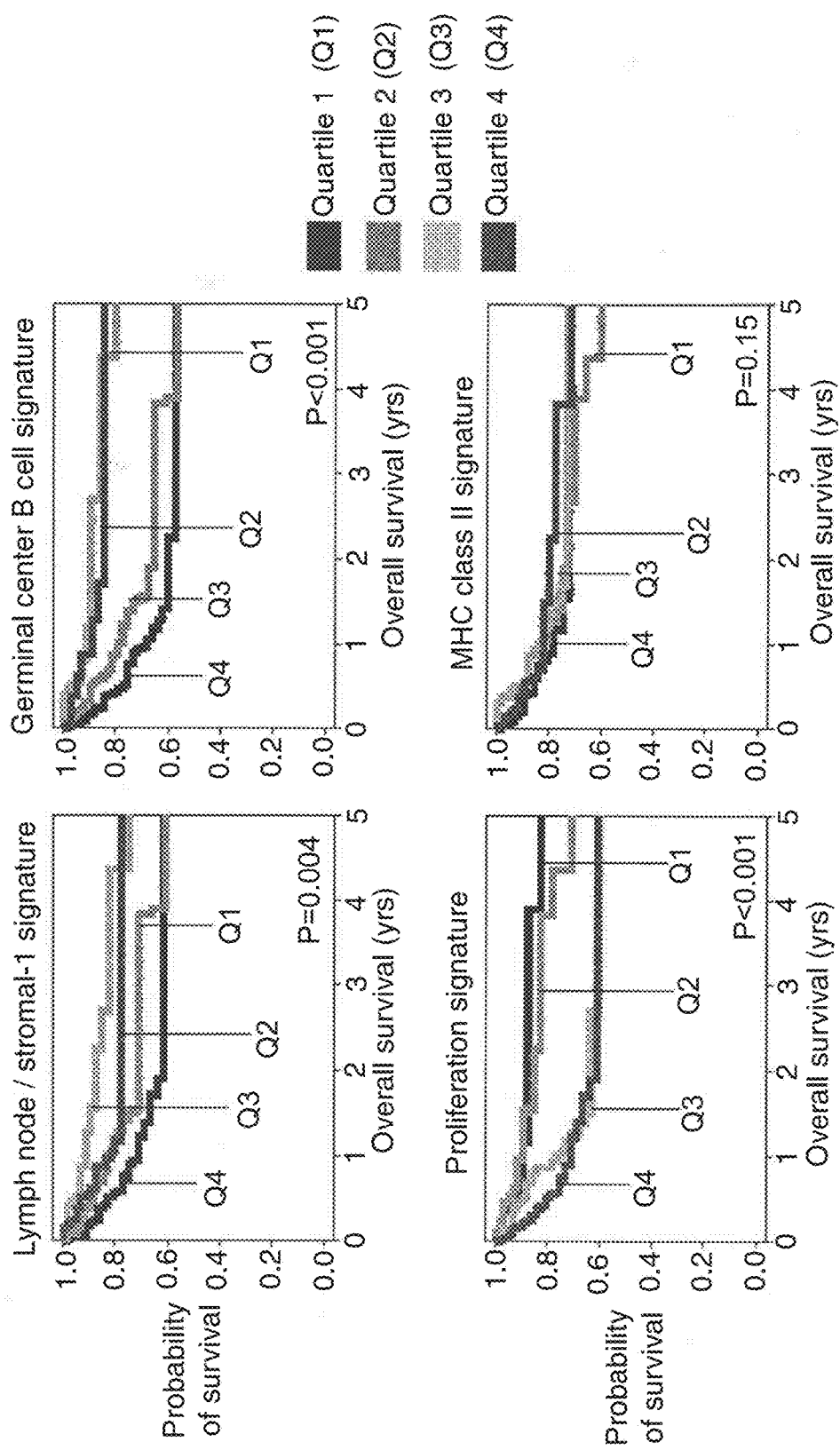
FIG. 1C is a series of four Kaplan-Meier estimates plots depicting the probabilities of overall survival versus time (in years) in DLBCL patients. Each of the four plots correlates the probability of overall survival with the lymph node/stromal-1, germinal center B cell, proliferation, or MHC class II gene expression signature, respectively. Moreover, in each plot, the average expression of the signature genes in each biopsy sample was used to rank cases and divide the cohort into quartile groups as indicated.
Figure 8A:
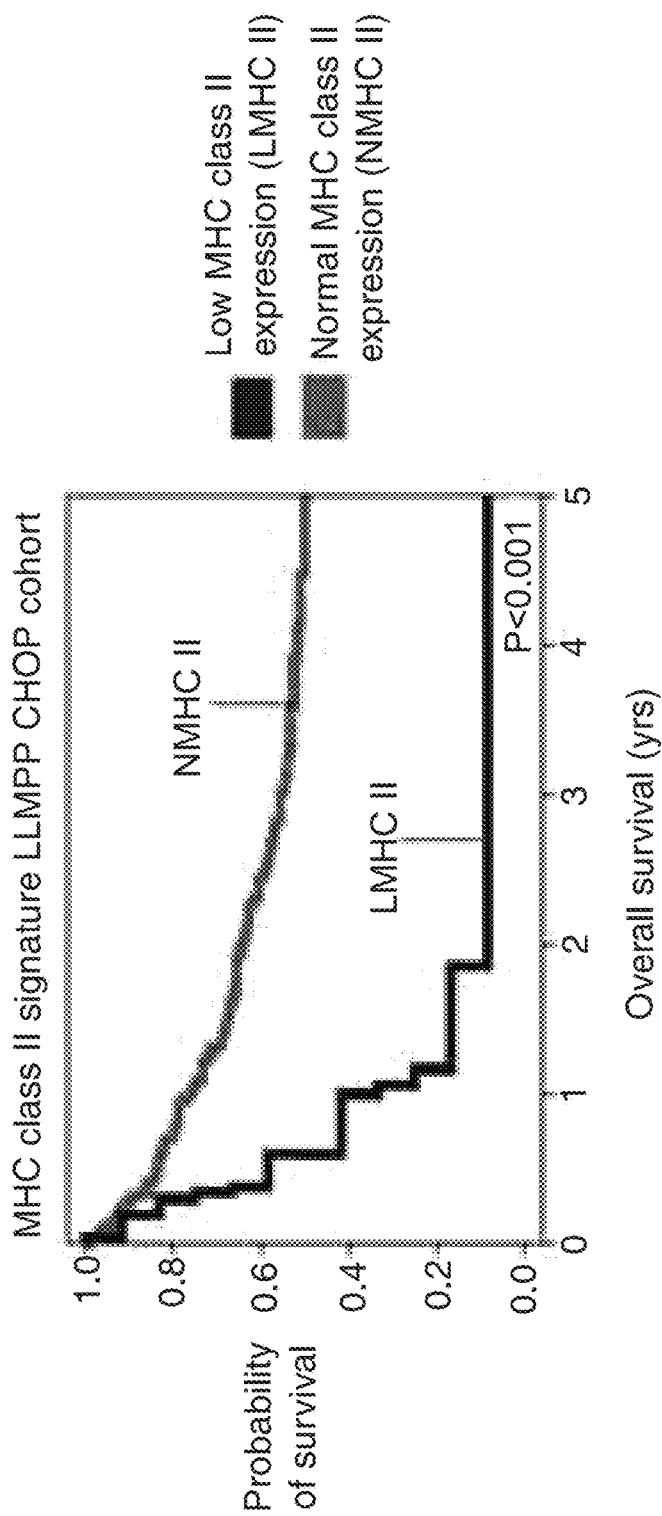
FIG. 8A is a Kaplan-Meier estimates plot depicting the probability of overall survival versus time (in years) in a "LLMPP CHOP" cohort, which was divided according to MHC class II signature expression levels. Patients with low MHC class II signature expression have significantly inferior overall survival compared to patients with normal MHC class II expression.
Figure 8B:
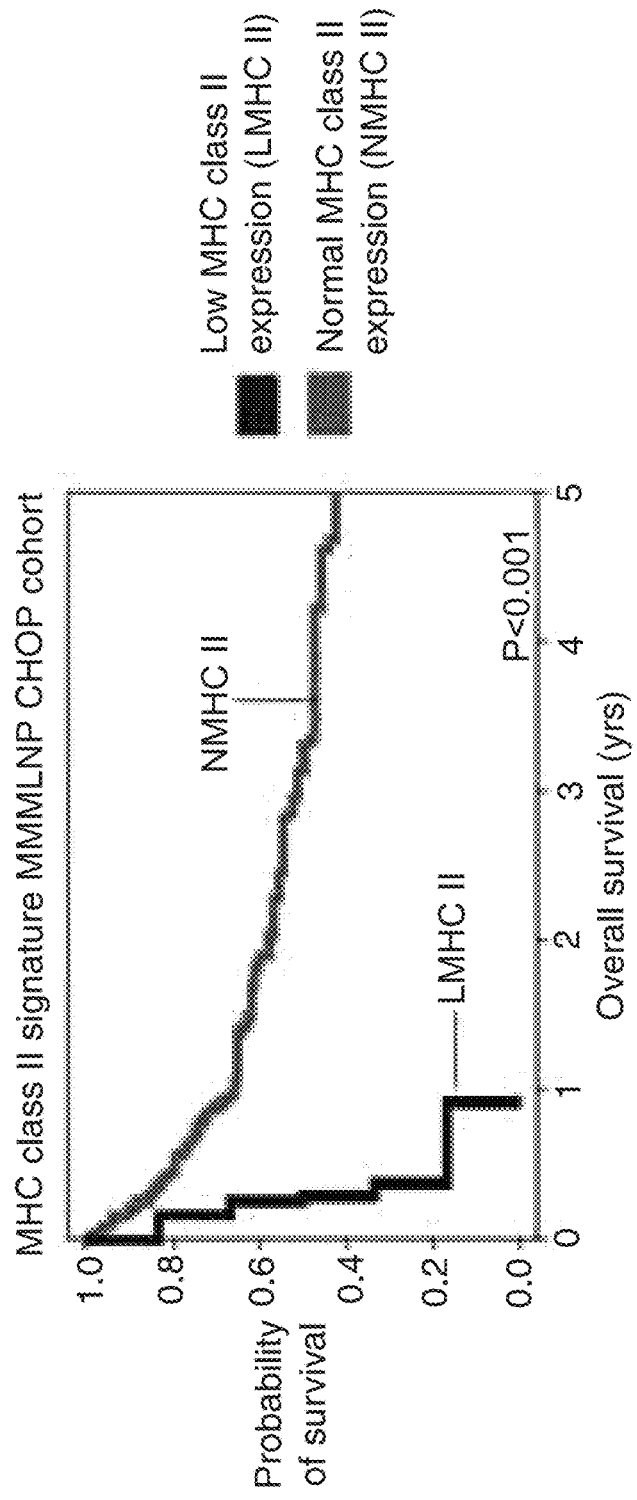
FIG. 8B is a Kaplan-Meier estimates plot depicting the probability of overall survival versus time (in years) in a "MMMLNP CHOP" cohort, which was divided according to MHC class II signature expression levels. Patients with low MHC class II signature expression have significantly inferior overall survival compared to patients with normal MHC class II expression.
Figure 8C:
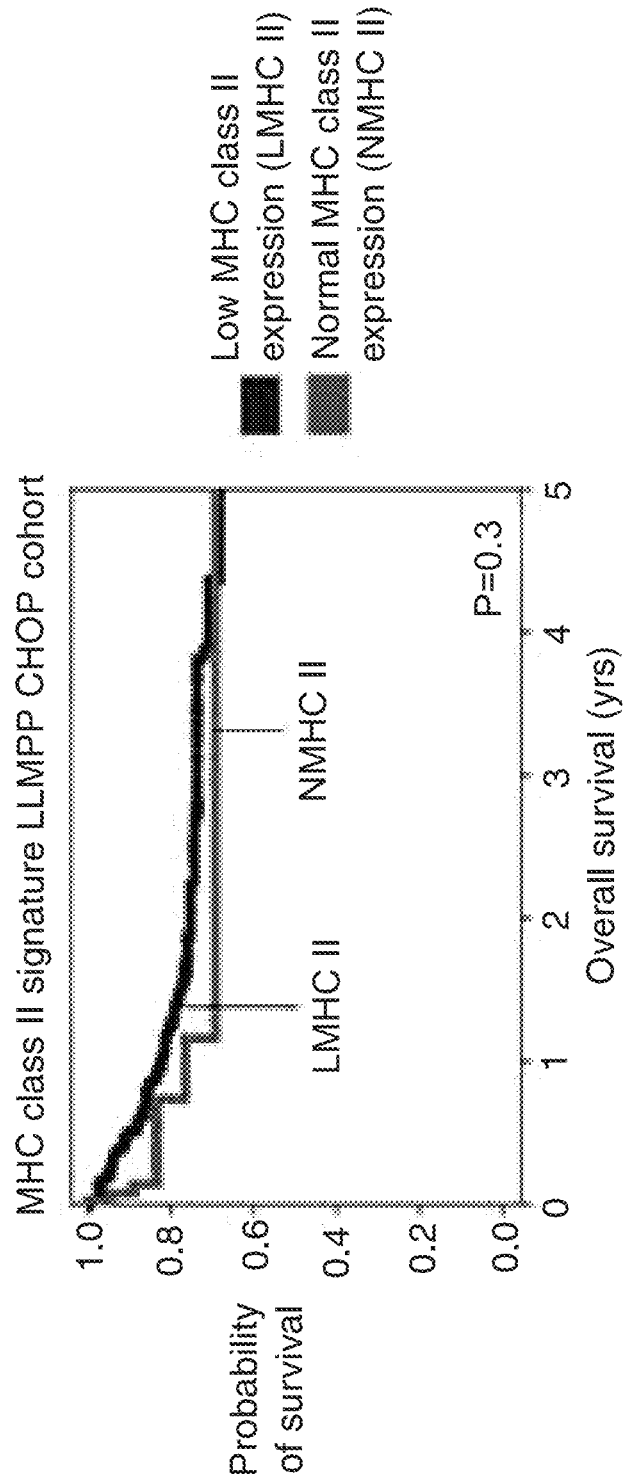
FIG. 8C is a Kaplan-Meier estimates plot depicting the probability of overall survival versus time (in years) in a "LLMPP R-CHOP" cohort, which was divided according to MHC class II signature expression levels. There was no significant difference in the overall survival of patients with low MHC class II signature expression as compared to patients with normal MHC class II expression.

The remaining fourth gene expression signature, the MHC class II signature, which was associated with survival in the CHOP training set when treated as a continuous variable, was not associated with survival in the R-CHOP cohort (see MHC class II signature panel in FIG. 1C). Moreover, tumors with extremely low "outlier" expression of this signature were associated with inferior survival in both CHOP cohorts (see FIGS. 8A and 8B), but not in the R-CHOP cohort (see FIG. 8C).

The foregoing results indicate that Rituximab immunotherapy combined with chemotherapy (R-CHOP) benefits both the ABC and GCB subtypes of DLBCL and that gene expression signatures that predicted survival in the context of CHOP chemotherapy retained their prognostic power among R-CHOP-treated patients.

The foregoing results also indicate that the biological variation among DLBCL tumors, as measured by gene expression signatures, has a consistent relationship to therapeutic response regardless of the treatment regimen used. There is a striking difference in 3-year progression-free survival between ABC DLBCL patients and GCB DLBCL patients treated with R-CHOP (40% vs. 74%). This difference is likely due to genetic and biological differences between these DLBCL subtypes (Staudt et al., *Adv. Immunol.*, 87: 163-208 (2005)).

Hence, future clinical trials in DLBCL should incorporate quantitative methods to discern these biological differences so that patient cohorts in different trials can be compared and treatment responses can be related to defined tumor phenotypes.

Example 2

This example demonstrates the development of GCB, stromal-1, and stromal-2 survival signatures and a related multivariate model of survival for R-CHOP-treated DLBCL.

Unless otherwise indicated, patient cohorts and methods of gene expression analysis are as described in Example 1.

In the LLMPP CHOP cohort data, 936 genes were identified as associated with poor prognosis $p<0.01$ (1-sided). For genes having multiple array probe sets associated with survival, only the probe set with the strongest association with survival was used. The expression values of the probe sets in the LLMPP CHOP cohort data were then clustered. The largest cluster with an average correlation of >0.6 and containing myc was identified as the proliferation survival signature. 1396 genes were identified as associated with favorable outcome. The largest cluster with average correlation of >0.6 and containing BCL6 was identified as the germinal center B cell (GCB) survival signature. A cluster with average correlation of >0.6 and containing FN1 was identified as the stromal-1 survival signature, whereas another cluster with average correlation of >0.6 containing HLADRA was identified as the MHC class II survival signature. The expression levels of genes within each signature were then averaged to create a "signature average" for each biopsy specimen. For the MMMLNP CHOP data set, the average was calculated for those array elements represented on the Affymetrix U133A microarray.

Figure 2A:
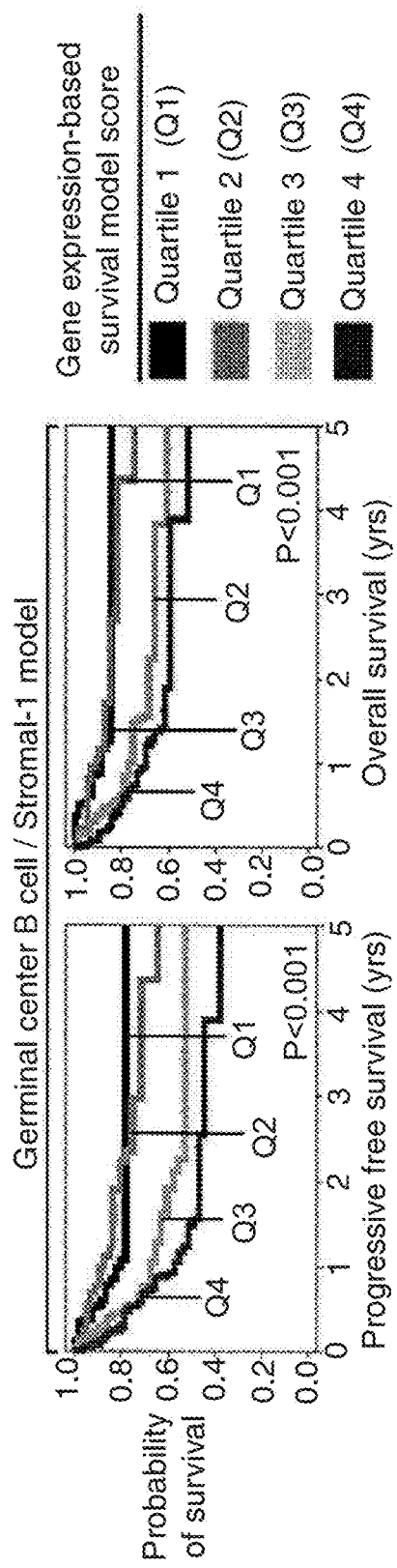
FIG. 2A is a pair of Kaplan-Meier estimates plots depicting the probability of progression-free-survival and the probability of overall survival, as indicated, versus time (in years) among DLBCL patients treated with R-CHOP. Patient samples were ranked according to a bivariate model created using the germinal center B cell (GCB) and stromal-1 signatures and divided into quartile groups.
Figure 9A:
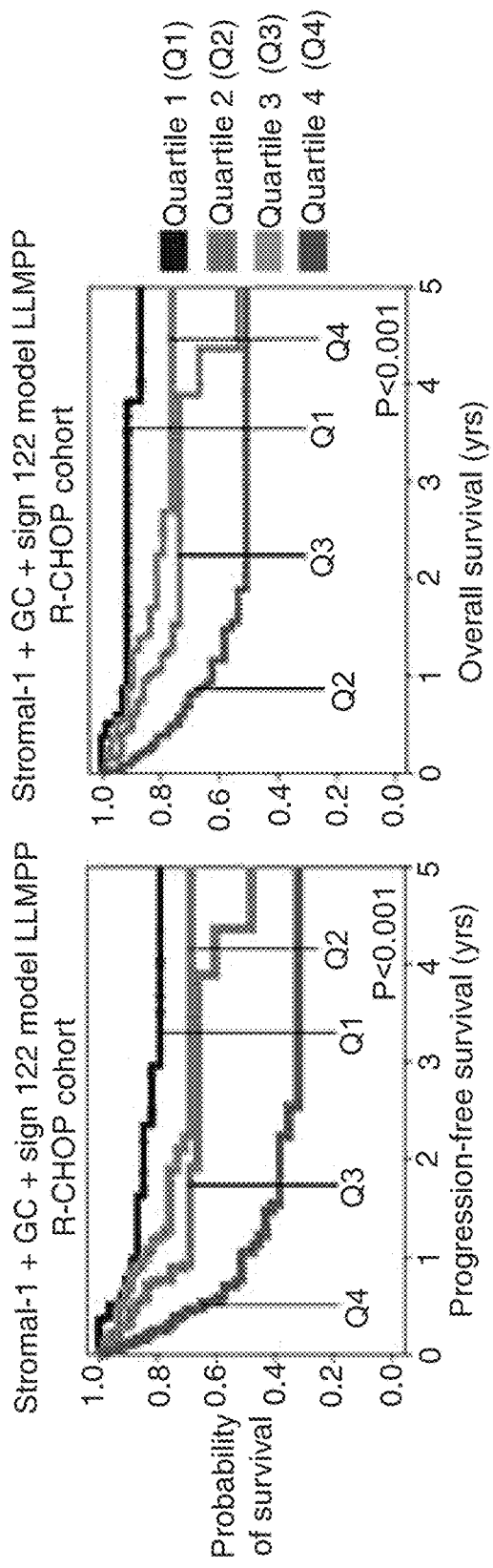
FIG. 9A is a pair of Kaplan-Meier estimates plots depicting the probabilities of progression-free survival or overall survival, as indicated, versus time (in years) among patients grouped into quartiles according to a gene expression model consisting of stromal-1 signature, GCB signature, and signature 122 following R-CHOP therapy.

From the four prognostic clusters or signatures, two signatures, the stromal-1 and the GCB signatures were used to create the best two variable survival model. Neither the proliferation nor the MHC class II signatures added to the prognostic value of this two variable model. This bivariate model performed well in the MMMLNP CHOP cohort (FIG. 9A) and in the R-CHOP cohort (FIG. 2A).

The CHOP training set was used to discover and refine signatures that added to the prognostic significance of this bivariate model, and the resulting multivariate models were tested in the R-CHOP cohort. 563 genes were identified as adding to the model in the direction of adverse prognosis. These genes were clustered by hierarchical clustering, and three clusters of more than 10 genes with an average correlation of >0.6 were identified. In addition, 542 genes were identified which added to the stromal-1 and GCB signature model in the direction of favorable prognosis. These genes were clustered, and two clusters of more than 10 genes with an average correlation of >0.6 were identified. Signature averages were determined for these clusters, and three variable models containing the stromal-1 and GCB signature and each of the cluster averages were formed on the MMMLNP CHOP and R-CHOP data sets. Of the five cluster averages, two were found to add statistical significance ($p<0.02$) in the MMMLNP CHOP data as compared to a model containing the stromal-1 and GCB signatures alone. By contrast, in the R-CHOP data, three of the five cluster averages were found to add significance ($p<0.02$) to the bivariate model. One of these cluster averages added significantly to the bivariate model in both the MMMLNP CHOP and R-CHOP data. This signature, designated Signature 122, was also found to add to the stromal-1 and GCB signature far more significantly than any of the four other signatures on the LLMPP CHOP data and, thus, was retained for further analysis.

Figure 2B:
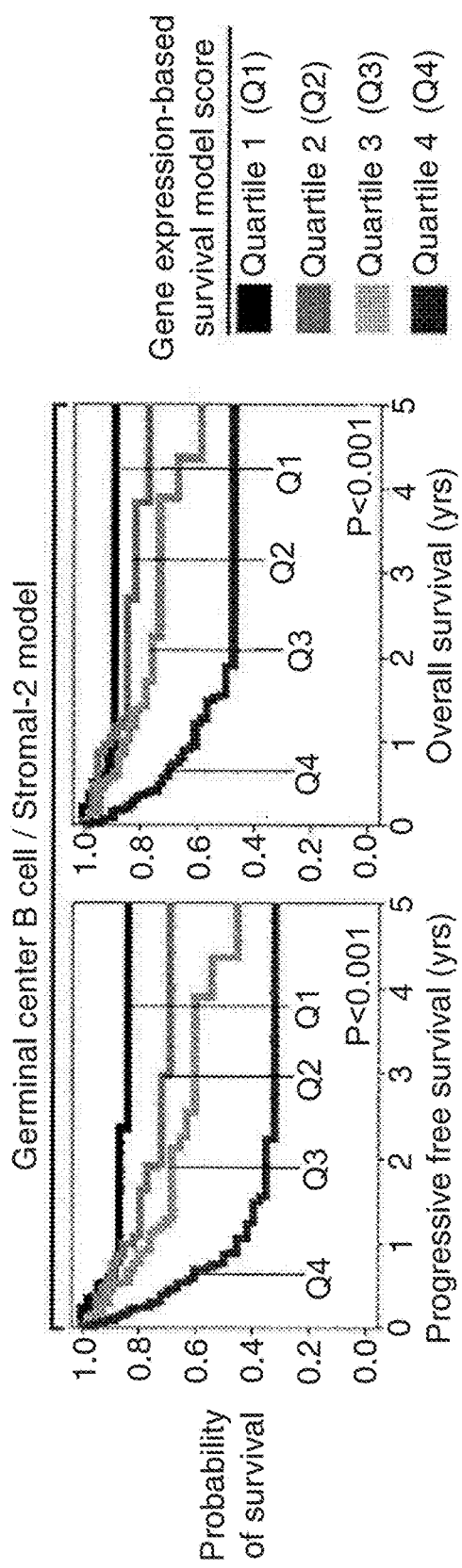
FIG. 2B is a pair of Kaplan-Meier plots depicting the probability of progression-free-survival and the probability of overall survival, as indicated, versus time (in years) among DLBCL patients treated with R-CHOP. Patient samples were ranked according to a survival predictor score derived from a model incorporating the germinal center B cell, stromal-1, and stromal-2 signatures and divided into quartile groups.
Figure 9B:
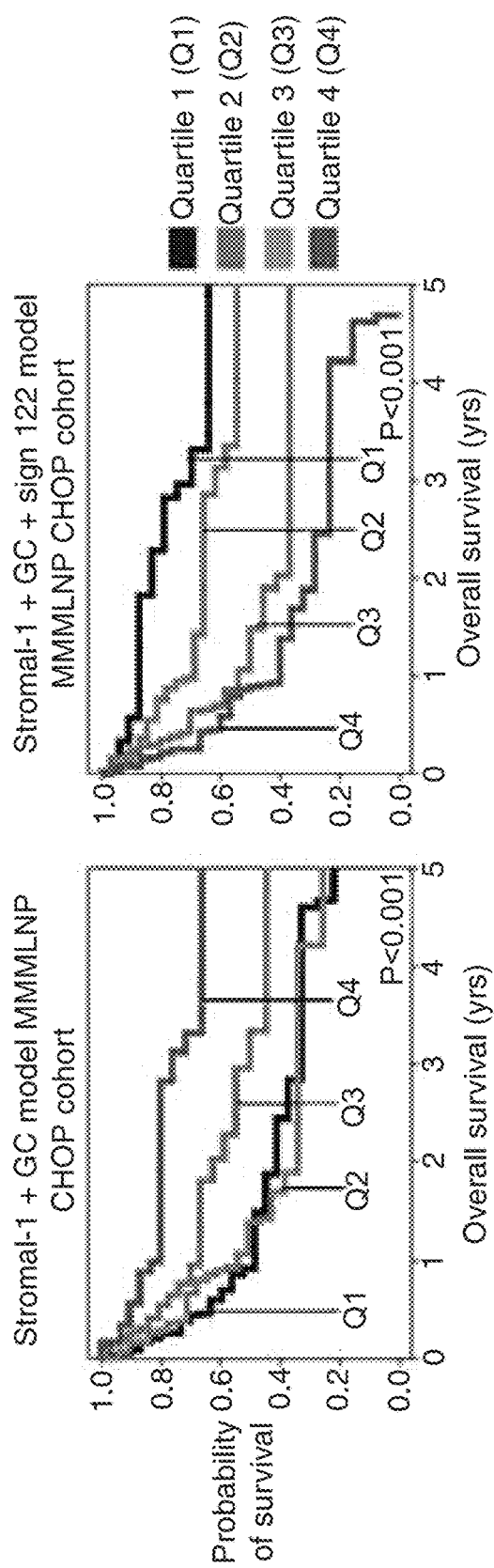
FIG. 9B is a pair Kaplan-Meier estimates plots depicting the probabilities of overall survival versus time (in years) among "MMMLNP CHOP" cohort patients grouped into quartiles according to a gene expression model consisting of either stromal-1 signature and GCB signature or stromal-1, GCB signature, and signature 122, as indicated, following CHOP therapy.
Figure 9C:
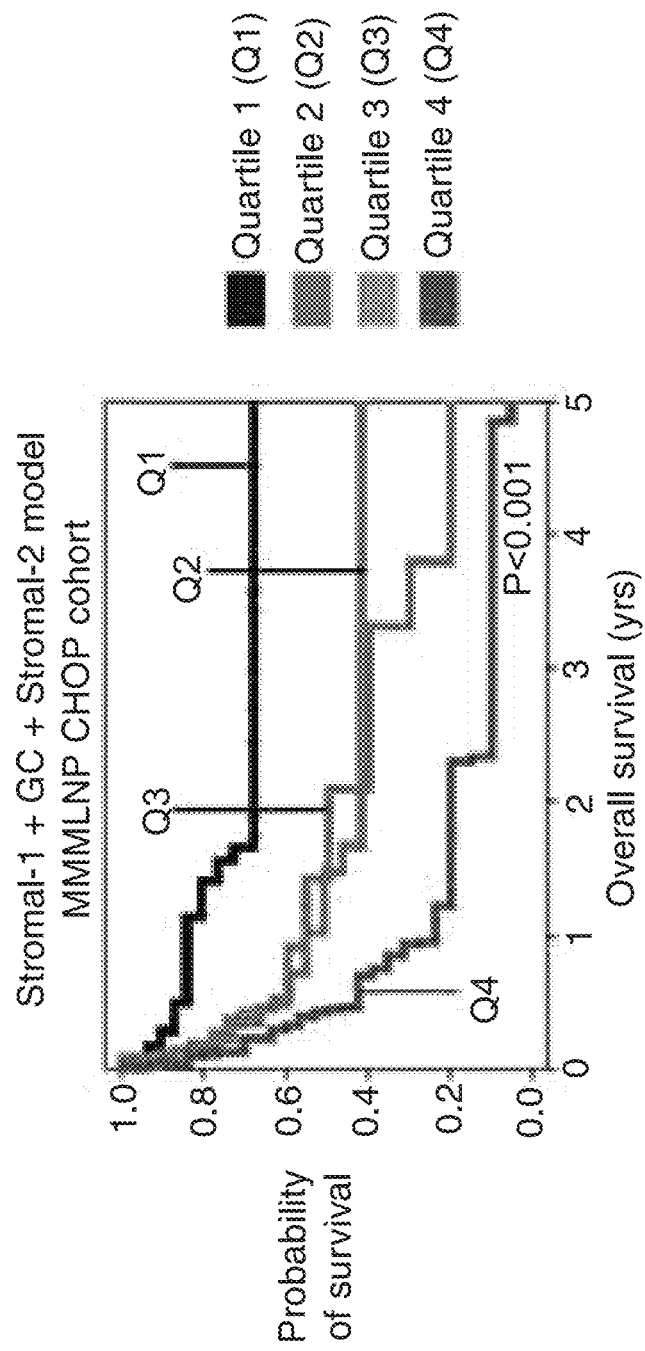
FIG. 9C is a Kaplan-Meier estimates plot depicting the probabilities of overall survival versus time (in years) among "MMMLNP CHOP" cohort patients grouped into quartiles according to a gene expression model consisting of stromal-1 signature, GCB signature, and stromal-2 signature following CHOP therapy.

Signature 122 added significantly to the bivariate model in both the MMMLNP CHOP cohort ($p=0.011$) and in the R-CHOP cohort ($p=0.001$) (FIGS. 9B and 9C). This Signature 122 positively correlated with the stromal-1 signature, although it was associated with adverse survival when added to the bivariate model. To further refine our model, we identified genes that were more correlated with Signature 122 than with the stromal-1 signature ($p<0.02$). These genes were organized by hierarchical clustering, and three sets of correlated genes ($r>0.6$) were observed. One of these clusters, the stromal-2 signature, added to the significance of the bivariate model in both the MMMLNP CHOP cohort ($p=0.002$) and the R-CHOP cohort ($p<0.001$) (FIGS. 2B and 9D).

Figure 3:
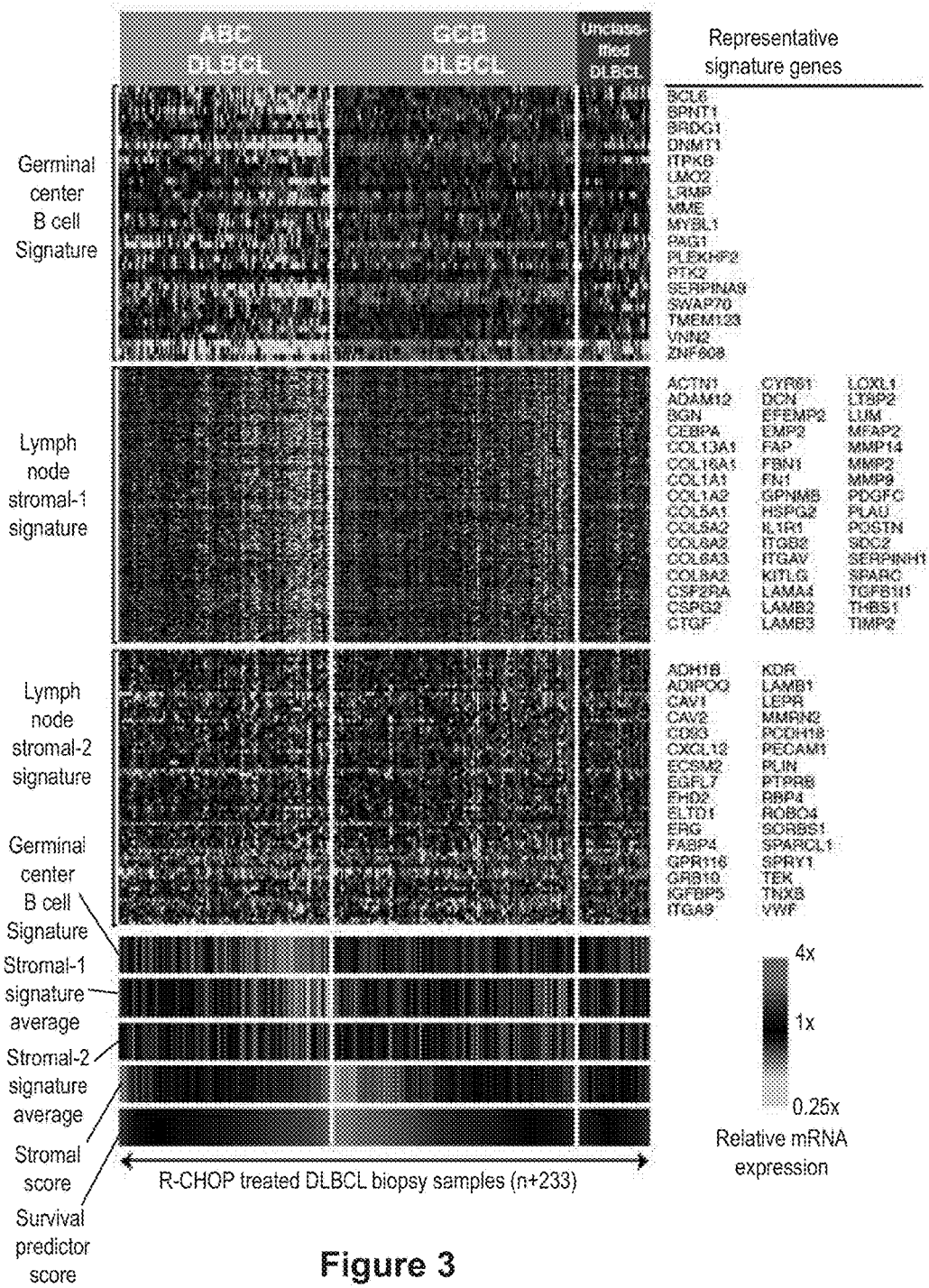
FIG. 3 depicts the expression levels of the indicated GCB cell, stromal-1, and stromal-2 signature genes in ABC, GCB, and unclassified DLBCL biopsy samples. Relative levels of gene expression are depicted according to the scale shown. Shown at the bottom are the signature averages for each patient. Also shown is the stromal score, which is the component of the survival model contributed by the difference between the stromal-2 and stromal-1 signature averages. The survival predictor score is shown for each patient and was used to order the cases, after grouping into ABC DLBCL, GCB DLBCL, and unclassified categories.

A multivariate survival model was formed by fitting a Cox model with the GCB, stromal-1, and stromal-2 signatures to the LLMPP CHOP cohort data shown in Table 3. This final multivariate model with its associated scaling coefficients was then evaluated on the MMLLMPP CHOP and R-CHOP cohort data sets. Survival predictor scores from the final model were used to divide the R-CHOP cohort into quartile groups with 3-year overall survival rates of 89%, 82%, 74%, and 48%, and 3-year progression-free survival rates of 84%, 69%, 61% and 33% (FIG. 2B). The survival predictor scores from the final model are illustrated in FIG. 3 along with the three component signatures and representative genes of each signature.

TABLE 3

| Patient | Time to death or last follow up (years) | Status at last follow up (1 = dead, 0 = alive) | Time to death, progression, or last follow up (years) | Status at last follow up (1 = progressed or died, 0 = no progression) | Germinal Center Signature Average | Stromal-1 Signature Average | Stromal-2 Signature Average | Model Score |
|---|---|---|---|---|---|---|---|---|
| 2 | 2.75 | 0 | 2.75 | 0 | 9.238 | 8.778 | 7.475 | 0.376 |
| 3 | 2.67 | 0 | 2.67 | 0 | 9.942 | 8.227 | 7.102 | 0.387 |
| 5 | 1.27 | 1 | 0.72 | 1 | 8.859 | 9.033 | 8.716 | 1.113 |

TABLE 3-continued

| Patient | Time to death or last follow up (years) | Status at last follow up (1 = dead, 0 = alive) | Time to death, progression, or last follow up (years) | Status at last follow up (1 = progressed or died, 0 = no progression) | Germinal Center Signature Average | Stromal-1 Signature Average | Stromal-2 Signature Average | Model Score |
|---|---|---|---|---|---|---|---|---|
| 21 | 2.39 | 0 | 2.40 | 0 | 10.573 | 8.519 | 6.959 | −0.270 |
| 22 | 2.38 | 0 | 2.38 | 0 | 8.737 | 8.686 | 7.598 | 0.761 |
| 23 | 2.52 | 0 | 2.52 | 0 | 10.694 | 10.322 | 8.817 | −0.897 |
| 24 | 5.11 | 0 | 5.11 | 0 | 11.376 | 7.854 | 7.598 | 0.500 |
| 26 | 4.01 | 0 | 4.01 | 0 | 9.829 | 9.956 | 8.507 | −0.372 |
| 28 | 3.96 | 0 | 3.96 | 0 | 10.957 | 9.277 | 8.248 | −0.330 |
| 41 | 0.52 | 1 | 0.52 | 1 | 9.273 | 9.437 | 8.202 | 0.183 |
| 47 | 1.53 | 1 | 0.77 | 1 | 9.548 | 8.802 | 8.061 | 0.617 |
| 48 | 0.37 | 1 | 0.12 | 1 | 8.660 | 8.279 | 6.891 | 0.729 |
| 49 | 2.37 | 0 | 2.35 | 1 | 10.915 | 8.988 | 6.847 | −0.965 |
| 53 | 3.89 | 0 | 2.23 | 1 | 9.530 | 9.792 | 9.693 | 0.721 |
| 61 | 0.90 | 1 | 0.46 | 1 | 8.649 | 8.038 | 8.104 | 1.798 |
| 65 | 4.04 | 0 | 4.04 | 0 | 10.744 | 9.330 | 7.930 | −0.508 |
| 66 | 4.04 | 0 | 4.04 | 0 | 10.714 | 10.016 | 7.536 | −1.459 |
| 95 | 0.62 | 1 | 0.44 | 1 | 9.244 | 9.197 | 8.105 | 0.373 |
| 96 | 5.37 | 0 | 5.37 | 0 | 10.107 | 8.723 | 7.608 | 0.157 |
| 97 | 5.07 | 0 | 5.07 | 0 | 9.777 | 9.192 | 7.359 | −0.349 |
| 98 | 0.94 | 1 | 0.59 | 1 | 8.794 | 7.711 | 7.367 | 1.571 |
| 99 | 0.40 | 1 | 0.40 | 1 | 9.024 | 9.272 | 9.160 | 1.101 |
| 103 | 0.03 | 1 | 0.02 | 1 | 8.883 | 8.190 | 7.742 | 1.301 |
| 104 | 3.76 | 0 | 3.76 | 0 | 9.785 | 9.866 | 7.929 | −0.652 |
| 106 | 2.95 | 0 | 2.95 | 0 | 10.585 | 7.797 | 6.824 | 0.367 |
| 107 | 2.94 | 0 | 2.94 | 0 | 11.535 | 8.358 | 6.660 | −0.711 |
| 108 | 2.73 | 0 | 2.73 | 0 | 9.653 | 8.495 | 7.550 | 0.539 |
| 109 | 0.16 | 1 | 0.11 | 1 | 9.301 | 9.376 | 7.994 | 0.092 |
| 110 | 2.46 | 0 | 2.46 | 0 | 10.254 | 8.980 | 7.324 | −0.357 |
| 111 | 2.44 | 0 | 2.44 | 0 | 10.137 | 10.691 | 8.948 | −0.949 |
| 113 | 2.12 | 0 | 2.12 | 0 | 10.746 | 8.555 | 6.942 | −0.390 |
| 114 | 1.98 | 0 | 0.88 | 1 | 8.562 | 8.159 | 7.120 | 1.047 |
| 115 | 1.92 | 0 | 1.92 | 0 | 10.313 | 9.385 | 8.157 | −0.231 |
| 118 | 1.64 | 0 | 1.64 | 0 | 10.209 | 10.194 | 8.231 | −0.959 |
| 119 | 1.60 | 0 | 1.60 | 0 | 11.059 | 8.852 | 7.479 | −0.461 |
| 1087 | 0.05 | 1 | 0.05 | 1 | 8.756 | 8.491 | 7.949 | 1.188 |
| 1089 | 5.12 | 0 | 1.27 | 1 | 9.863 | 9.135 | 8.034 | 0.129 |
| 1091 | 5.15 | 0 | 5.15 | 0 | 10.454 | 9.918 | 8.742 | −0.437 |
| 1092 | 5.06 | 0 | 5.07 | 0 | 9.452 | 9.467 | 8.912 | 0.556 |
| 1093 | 3.83 | 1 | 1.62 | 1 | 9.915 | 9.138 | 7.747 | −0.090 |
| 1096 | 4.02 | 0 | 4.02 | 0 | 8.887 | 9.236 | 7.795 | 0.274 |
| 1097 | 1.26 | 1 | 1.08 | 1 | 11.219 | 9.234 | 8.321 | −0.347 |
| 1098 | 3.53 | 0 | 3.53 | 0 | 9.117 | 9.236 | 7.655 | 0.082 |
| 1099 | 3.07 | 0 | 0.91 | 1 | 9.284 | 8.798 | 7.741 | 0.515 |
| 1101 | 5.64 | 0 | 5.64 | 0 | 9.803 | 9.466 | 8.156 | −0.101 |
| 1108 | 3.30 | 0 | 3.30 | 0 | 9.195 | 10.456 | 9.065 | −0.237 |
| 1109 | 3.78 | 0 | 3.78 | 0 | 11.008 | 10.051 | 8.273 | −1.120 |
| 1164 | 0.19 | 1 | 0.16 | 1 | 9.242 | 10.307 | 10.548 | 0.896 |
| 1167 | 1.49 | 1 | 0.45 | 1 | 9.809 | 9.105 | 8.784 | 0.687 |
| 1168 | 0.42 | 1 | 0.30 | 1 | 8.718 | 8.368 | 7.149 | 0.790 |
| 1169 | 1.71 | 1 | 1.22 | 1 | 11.512 | 8.108 | 7.507 | 0.125 |
| 1172 | 2.82 | 0 | 2.82 | 0 | 11.137 | 8.871 | 8.153 | −0.057 |
| 1173 | 0.87 | 1 | 0.79 | 1 | 11.324 | 9.914 | 8.514 | −0.950 |
| 1175 | 1.06 | 1 | 0.56 | 1 | 9.107 | 10.310 | 9.063 | −0.053 |
| 1179 | 2.53 | 0 | 2.53 | 0 | 9.506 | 9.437 | 8.461 | 0.260 |
| 1181 | 1.72 | 0 | 1.72 | 0 | 10.688 | 9.018 | 7.647 | −0.360 |
| 1184 | 4.74 | 0 | 2.97 | 1 | 10.812 | 8.979 | 7.922 | −0.187 |
| 1185 | 3.71 | 0 | 3.71 | 0 | 10.431 | 8.397 | 7.317 | 0.156 |
| 1186 | 3.43 | 0 | 3.43 | 0 | 8.688 | 8.944 | 8.552 | 1.164 |
| 1187 | 5.23 | 0 | 5.23 | 0 | 10.072 | 10.192 | 8.667 | −0.604 |
| 1189 | 5.13 | 0 | 5.13 | 0 | 10.109 | 9.212 | 7.967 | −0.097 |
| 1190 | 3.66 | 0 | 3.66 | 0 | 10.713 | 10.409 | 8.910 | −0.930 |
| 1192 | 0.16 | 1 | 0.16 | 1 | 8.825 | 9.903 | 8.061 | −0.199 |
| 1195 | 4.36 | 0 | 4.36 | 0 | 11.539 | 7.567 | 6.873 | 0.234 |
| 1197 | 3.13 | 0 | 3.13 | 0 | 10.287 | 10.365 | 9.549 | −0.275 |
| 1200 | 0.31 | 1 | 0.31 | 1 | 9.432 | 8.950 | 9.805 | 1.692 |
| 1206 | 6.51 | 0 | 6.51 | 0 | 10.410 | 9.946 | 8.925 | −0.323 |
| 1211 | 6.25 | 0 | 6.25 | 0 | 11.596 | 7.908 | 6.524 | −0.372 |
| 1215 | 5.35 | 0 | 5.35 | 0 | 10.504 | 9.061 | 7.550 | −0.392 |
| 1216 | 0.46 | 1 | 0.29 | 1 | 10.017 | 9.010 | 7.794 | 0.028 |
| 1219 | 0.51 | 1 | 0.51 | 1 | 10.614 | 10.014 | 8.619 | −0.683 |
| 1220 | 2.24 | 1 | 2.25 | 1 | 8.850 | 9.400 | 8.036 | 0.286 |
| 1221 | 3.94 | 0 | 3.95 | 0 | 8.777 | 7.489 | 6.672 | 1.334 |
| 1222 | 3.53 | 0 | 3.53 | 0 | 10.463 | 9.310 | 7.019 | −0.986 |
| 1224 | 3.22 | 0 | 2.11 | 1 | 9.751 | 9.505 | 8.453 | 0.082 |
| 1225 | 2.95 | 0 | 2.95 | 0 | 8.613 | 8.313 | 7.668 | 1.240 |
| 1226 | 0.08 | 1 | 0.08 | 1 | 9.229 | 8.851 | 7.950 | 0.625 |
| 1228 | 2.78 | 0 | 0.99 | 1 | 11.532 | 8.261 | 6.932 | −0.428 |

TABLE 3-continued

| Patient | Time to death or last follow up (years) | Status at last follow up (1 = dead, 0 = alive) | Time to death, progression, or last follow up (years) | Status at last follow up (1 = progressed or died, 0 = no progression) | Germinal Center Signature Average | Stromal-1 Signature Average | Stromal-2 Signature Average | Model Score |
|---|---|---|---|---|---|---|---|---|
| 1230 | 0.59 | 1 | 0.54 | 1 | 9.369 | 6.951 | 6.956 | 1.825 |
| 1231 | 1.41 | 0 | 1.41 | 0 | 10.248 | 8.788 | 8.011 | 0.303 |
| 1232 | 2.49 | 0 | 0.68 | 1 | 10.362 | 8.528 | 7.975 | 0.495 |
| 1233 | 2.50 | 0 | 2.50 | 0 | 9.239 | 10.581 | 8.470 | −0.784 |
| 1236 | 2.56 | 0 | 2.56 | 0 | 9.156 | 10.000 | 7.805 | −0.608 |
| 1238 | 0.16 | 1 | 0.16 | 1 | 9.488 | 9.055 | 8.256 | 0.517 |
| 1239 | 2.24 | 0 | 2.24 | 0 | 8.886 | 8.978 | 7.838 | 0.564 |
| 1240 | 1.48 | 0 | 1.48 | 0 | 10.474 | 9.073 | 7.702 | −0.288 |
| 1241 | 1.41 | 1 | 1.17 | 1 | 9.044 | 9.054 | 7.451 | 0.160 |
| 1251 | 2.72 | 0 | 2.72 | 0 | 8.410 | 8.687 | 7.082 | 0.549 |
| 1252 | 0.01 | 1 | 0.01 | 1 | 11.167 | 8.070 | 7.358 | 0.206 |
| 1255 | 5.17 | 0 | 5.17 | 0 | 9.501 | 9.411 | 7.887 | −0.099 |
| 1271 | 4.72 | 0 | 4.73 | 0 | 10.718 | 8.452 | 7.060 | −0.194 |
| 1272 | 5.68 | 0 | 5.68 | 0 | 9.161 | 9.080 | 7.668 | 0.231 |
| 1275 | 1.89 | 1 | 1.48 | 1 | 9.257 | 8.559 | 8.607 | 1.354 |
| 1277 | 5.06 | 0 | 5.07 | 0 | 11.091 | 9.938 | 8.274 | −1.038 |
| 1279 | 4.87 | 0 | 4.87 | 0 | 9.309 | 10.085 | 9.676 | 0.504 |
| 1281 | 3.36 | 0 | not available (n/a) | n/a | 9.535 | 9.969 | 9.090 | 0.132 |
| 1284 | 3.51 | 0 | 3.51 | 0 | 10.922 | 9.680 | 8.481 | −0.567 |
| 1288 | 1.54 | 0 | n/a | n/a | 9.430 | 8.896 | 8.037 | 0.554 |
| 1289 | 0.03 | 1 | 0.03 | 1 | 8.915 | 9.052 | 8.002 | 0.589 |
| 1290 | 5.23 | 0 | 5.23 | 0 | 10.432 | 10.426 | 8.154 | −1.340 |
| 1291 | 0.04 | 1 | 0.04 | 1 | 11.319 | 8.246 | 7.323 | −0.059 |
| 1292 | 0.10 | 1 | 0.10 | 1 | 8.667 | 8.764 | 8.110 | 1.058 |
| 1293 | 4.81 | 0 | 4.81 | 0 | 11.116 | 9.842 | 8.083 | −1.081 |
| 1294 | 0.53 | 1 | 0.53 | 1 | 10.138 | 10.181 | 8.501 | −0.733 |
| 1295 | 5.16 | 0 | 5.17 | 0 | 9.445 | 9.694 | 7.739 | −0.463 |
| 1296 | 4.79 | 0 | 4.79 | 0 | 10.228 | 9.064 | 8.852 | 0.600 |
| 1297 | 4.24 | 0 | 4.24 | 0 | 9.524 | 7.990 | 7.008 | 0.740 |
| 1298 | 4.56 | 0 | 4.56 | 0 | 9.022 | 9.000 | 7.695 | 0.389 |
| 1331 | 3.29 | 0 | 3.29 | 0 | 11.004 | 9.488 | 8.289 | −0.536 |
| 1334 | 2.87 | 0 | 2.87 | 0 | 11.434 | 9.509 | 8.109 | −0.859 |
| 1335 | 1.38 | 1 | 0.90 | 1 | 9.586 | 8.545 | 7.423 | 0.431 |
| 1336 | 2.44 | 0 | 2.44 | 0 | 10.844 | 9.704 | 7.706 | −1.082 |
| 1337 | 0.02 | 1 | 0.02 | 1 | 8.521 | 7.788 | 7.860 | 1.941 |
| 1449 | 1.62 | 0 | 1.62 | 0 | 9.604 | 8.463 | 8.030 | 0.917 |
| 1450 | 1.30 | 0 | 0.53 | 1 | 8.571 | 8.112 | 7.241 | 1.173 |
| 1451 | 1.84 | 0 | 1.85 | 0 | 10.637 | 9.205 | 7.759 | −0.452 |
| 1453 | 1.71 | 0 | 1.71 | 0 | 10.964 | 9.089 | 8.226 | −0.157 |
| 1454 | 0.62 | 0 | 0.62 | 0 | 11.106 | 8.514 | 7.604 | −0.052 |
| 1553 | 2.93 | 0 | 1.92 | 1 | 8.975 | 9.284 | 7.475 | −0.029 |
| 1612 | 5.37 | 0 | 5.37 | 0 | 10.526 | 9.471 | 7.809 | −0.643 |
| 1613 | 5.81 | 0 | n/a | n/a | 10.868 | 9.695 | 7.730 | −1.067 |
| 1614 | 4.36 | 1 | 4.36 | 1 | 10.358 | 9.226 | 8.765 | 0.322 |
| 1617 | 0.52 | 0 | 0.52 | 0 | 10.332 | 8.723 | 7.180 | −0.227 |
| 1618 | 1.70 | 0 | 0.98 | 1 | 11.233 | 8.956 | 7.852 | −0.387 |
| 1619 | 0.25 | 1 | 0.25 | 1 | 8.646 | 8.028 | 7.123 | 1.146 |
| 1620 | 2.17 | 0 | 2.17 | 0 | 11.647 | 8.385 | 7.343 | −0.325 |
| 1623 | 2.80 | 0 | 2.80 | 0 | 9.611 | 9.484 | 8.249 | 0.024 |
| 1626 | 1.76 | 0 | 1.76 | 0 | 11.236 | 9.495 | 8.108 | −0.763 |
| 1628 | 3.13 | 0 | 1.23 | 1 | 8.714 | 7.972 | 7.149 | 1.192 |
| 1645 | 2.85 | 0 | 2.85 | 0 | 10.146 | 9.476 | 8.914 | 0.258 |
| 1647 | 2.79 | 0 | 2.80 | 0 | 10.485 | 10.495 | 8.707 | −1.058 |
| 1650 | 0.75 | 1 | 0.75 | 1 | 8.830 | 7.346 | 6.486 | 1.333 |
| 1651 | 1.66 | 0 | 1.66 | 0 | 9.190 | 7.949 | 6.829 | 0.801 |
| 1652 | 1.64 | 0 | n/a | n/a | 8.798 | 8.943 | 8.331 | 0.969 |
| 1702 | 1.05 | 0 | 1.05 | 1 | 9.008 | 8.217 | 8.078 | 1.447 |
| 1703 | 0.70 | 1 | 0.70 | 1 | 9.499 | 8.637 | 7.790 | 0.621 |
| 1704 | 3.14 | 0 | 3.14 | 0 | 9.908 | 9.231 | 7.503 | −0.347 |
| 1705 | 3.94 | 0 | 3.94 | 0 | 8.933 | 8.445 | 8.187 | 1.321 |
| 1707 | 2.80 | 0 | 2.80 | 0 | 10.610 | 9.348 | 7.872 | −0.510 |
| 1742 | 3.27 | 0 | n/a | n/a | 10.033 | 8.715 | 7.412 | 0.063 |
| 1746 | 1.91 | 0 | 1.55 | 1 | 9.249 | 8.705 | 8.205 | 0.937 |
| 1747 | 1.48 | 0 | 1.48 | 0 | 10.162 | 8.866 | 7.602 | −0.016 |
| 1756 | 3.47 | 0 | 3.47 | 0 | 10.815 | 9.638 | 7.248 | −1.312 |
| 1761 | 0.23 | 1 | 0.23 | 1 | 9.842 | 10.192 | 8.664 | −0.511 |
| 1762 | 5.20 | 0 | 5.20 | 0 | 10.583 | 9.333 | 7.445 | −0.772 |
| 1763 | 5.51 | 0 | 5.51 | 0 | 8.917 | 8.925 | 8.084 | 0.771 |
| 1766 | 1.59 | 0 | 1.59 | 0 | 10.919 | 10.037 | 8.389 | −0.990 |
| 1782 | 1.09 | 0 | 1.09 | 0 | 10.753 | 9.600 | 8.332 | −0.516 |
| 1788 | 0.39 | 1 | 0.24 | 1 | 10.364 | 8.738 | 8.914 | 0.915 |
| 1861 | 0.56 | 1 | 0.19 | 1 | 9.728 | 8.604 | 7.594 | 0.427 |
| 1867 | 1.17 | 1 | 0.38 | 1 | 8.903 | 11.501 | 10.559 | −0.166 |
| 1916 | 1.41 | 0 | n/a | n/a | 9.295 | 11.197 | 11.508 | 0.619 |
| 1920 | 1.32 | 0 | 1.32 | 0 | 10.165 | 9.630 | 8.789 | 0.009 |

TABLE 3-continued

| Patient | Time to death or last follow up (years) | Status at last follow up (1 = dead, 0 = alive) | Time to death, progression, or last follow up (years) | Status at last follow up (1 = progressed or died, 0 = no progression) | Germinal Center Signature Average | Stromal-1 Signature Average | Stromal-2 Signature Average | Model Score |
|---|---|---|---|---|---|---|---|---|
| 1927 | 1.53 | 0 | 1.53 | 0 | 9.195 | 10.261 | 9.791 | 0.451 |
| 1928 | 0.72 | 0 | 0.72 | 0 | 9.769 | 8.510 | 7.330 | 0.328 |
| 1939 | 0.47 | 1 | 0.47 | 1 | 9.097 | 9.363 | 7.647 | −0.043 |
| 2002 | 1.29 | 0 | 1.30 | 0 | 9.469 | 9.542 | 8.600 | 0.262 |
| 2006 | 1.23 | 0 | 1.23 | 0 | 10.434 | 8.223 | 7.162 | 0.227 |
| 2067 | 2.18 | 0 | 2.18 | 0 | 10.244 | 11.186 | 9.391 | −1.197 |
| 2070 | 0.31 | 0 | 0.12 | 1 | 10.486 | 10.680 | 10.353 | −0.135 |
| 2162 | 0.38 | 1 | 0.38 | 1 | 10.934 | 10.020 | 7.960 | −1.268 |
| 2270 | 1.59 | 0 | 1.59 | 0 | 10.117 | 9.904 | 8.506 | −0.440 |
| 2271 | 1.60 | 0 | 1.60 | 0 | 8.995 | 9.349 | 8.261 | 0.428 |
| 2274 | 0.41 | 0 | 0.41 | 0 | 8.863 | 7.623 | 7.222 | 1.533 |
| 2283 | 1.19 | 0 | 1.19 | 0 | 10.501 | 8.361 | 6.741 | −0.226 |
| 2291 | 0.87 | 1 | 0.85 | 1 | 10.732 | 10.184 | 9.436 | −0.353 |
| 2299 | 0.93 | 0 | 0.93 | 0 | 10.661 | 9.905 | 8.189 | −0.883 |
| 2301 | 0.61 | 0 | 0.61 | 0 | 9.852 | 9.903 | 8.352 | −0.432 |
| 2306 | 0.68 | 0 | 0.68 | 0 | 8.586 | 8.759 | 8.191 | 1.151 |
| 2309 | 0.43 | 0 | 0.43 | 0 | 10.839 | 7.671 | 6.860 | 0.413 |
| 2311 | 0.80 | 0 | 0.80 | 0 | 10.901 | 7.797 | 6.912 | 0.294 |
| 2318 | 0.99 | 0 | 0.99 | 0 | 10.283 | 9.403 | 8.655 | 0.100 |
| 2321 | 0.82 | 0 | 0.82 | 0 | 9.691 | 8.956 | 7.404 | −0.044 |
| 2411 | 0.67 | 0 | 0.67 | 0 | 8.986 | 8.383 | 7.854 | 1.137 |
| 2415 | 0.62 | 0 | 0.62 | 0 | 9.296 | 10.509 | 9.551 | −0.005 |
| 2444 | 3.99 | 0 | 3.99 | 0 | 10.154 | 9.871 | 9.026 | −0.071 |
| 2445 | 3.36 | 0 | 3.36 | 0 | 8.788 | 8.184 | 7.964 | 1.497 |
| 2479 | 0.51 | 0 | 0.51 | 0 | 11.151 | 9.023 | 8.199 | −0.186 |
| 2482 | 4.54 | 0 | 4.54 | 0 | 10.373 | 9.847 | 8.208 | −0.691 |
| 2483 | 3.89 | 1 | 3.89 | 1 | 9.241 | 8.902 | 7.742 | 0.428 |
| 2484 | 2.69 | 1 | 1.90 | 1 | 10.279 | 9.619 | 8.312 | −0.349 |
| 2485 | 4.43 | 0 | 4.43 | 0 | 9.957 | 9.865 | 8.439 | −0.378 |
| 2486 | 4.37 | 0 | n/a | n/a | 10.698 | 10.203 | 8.041 | −1.301 |
| 2487 | 4.34 | 0 | 4.34 | 0 | 11.227 | 9.909 | 8.260 | −1.076 |
| 2488 | 4.20 | 0 | 4.21 | 0 | 9.510 | 8.709 | 7.615 | 0.426 |
| 2490 | 4.02 | 0 | 4.02 | 0 | 10.510 | 10.961 | 8.956 | −1.374 |
| 2491 | 0.50 | 1 | 0.25 | 1 | 9.047 | 8.554 | 7.624 | 0.784 |
| 2492 | 3.96 | 0 | 3.96 | 0 | 9.904 | 10.901 | 9.140 | −0.935 |
| 2497 | 3.44 | 0 | 3.44 | 0 | 9.221 | 9.438 | 8.065 | 0.111 |
| 2498 | 3.37 | 0 | 3.37 | 0 | 9.318 | 9.427 | 8.003 | 0.040 |
| 2500 | 3.31 | 0 | 3.31 | 0 | 11.014 | 9.406 | 7.375 | −1.074 |
| 2501 | 3.28 | 0 | n/a | n/a | 8.822 | 8.551 | 7.750 | 0.966 |
| 2503 | 2.99 | 0 | 2.99 | 0 | 8.301 | 7.967 | 6.929 | 1.222 |
| 2504 | 2.78 | 0 | 2.78 | 0 | 10.145 | 8.004 | 7.017 | 0.472 |
| 2505 | 2.76 | 0 | 2.76 | 0 | 11.036 | 8.442 | 7.136 | −0.266 |
| 2507 | 0.86 | 1 | 0.54 | 1 | 9.737 | 9.475 | 8.988 | 0.480 |
| 2508 | 2.58 | 0 | 2.58 | 0 | 8.678 | 9.389 | 8.230 | 0.498 |
| 2509 | 0.96 | 1 | 0.76 | 1 | 8.895 | 10.441 | 9.088 | −0.081 |
| 2511 | 1.55 | 1 | 1.06 | 1 | 9.225 | 9.267 | 9.191 | 1.042 |
| 2512 | 2.45 | 0 | 2.45 | 0 | 11.047 | 10.465 | 9.337 | −0.838 |
| 2513 | 0.61 | 1 | 0.61 | 1 | 10.855 | 10.378 | 8.395 | −1.305 |
| 2514 | 2.18 | 0 | 2.18 | 0 | 10.477 | 9.832 | 7.498 | −1.198 |
| 2515 | 2.13 | 0 | 2.13 | 0 | 9.295 | 10.519 | 9.788 | 0.145 |
| 2516 | 2.07 | 0 | 2.07 | 0 | 10.575 | 10.592 | 8.642 | −1.238 |
| 2517 | 2.04 | 0 | 0.76 | 1 | 9.385 | 9.163 | 8.328 | 0.498 |
| 2584 | 0.68 | 0 | 0.68 | 0 | 10.759 | 9.356 | 8.135 | −0.404 |
| 2599 | 4.05 | 0 | 4.05 | 0 | 10.629 | 9.158 | 7.724 | −0.425 |
| 2600 | 1.01 | 1 | 0.54 | 1 | 9.785 | 8.619 | 7.291 | 0.184 |
| 2601 | 1.22 | 1 | 0.88 | 1 | 9.385 | 8.044 | 7.178 | 0.859 |
| 2603 | 4.43 | 0 | 4.43 | 0 | 9.582 | 10.707 | 9.803 | −0.156 |
| 2604 | 0.84 | 0 | 0.36 | 1 | 9.844 | 10.511 | 8.382 | −1.026 |
| 2609 | 8.89 | 0 | 2.55 | 1 | 8.981 | 8.775 | 7.506 | 0.507 |
| 2610 | 0.74 | 0 | 0.74 | 0 | 10.793 | 8.964 | 7.421 | −0.502 |
| 2611 | 0.66 | 0 | 0.66 | 0 | 10.353 | 10.233 | 9.032 | −0.518 |
| 2612 | 1.17 | 1 | 1.13 | 1 | 10.290 | 9.028 | 8.287 | 0.230 |
| 2613 | 1.66 | 0 | 1.66 | 0 | 10.997 | 9.089 | 7.749 | −0.493 |
| 2614 | 0.21 | 1 | 0.21 | 1 | 8.768 | 7.850 | 7.100 | 1.261 |
| 2615 | 0.48 | 0 | 0.48 | 0 | 11.359 | 9.470 | 7.647 | −1.100 |
| 2639 | 10.29 | 0 | 10.30 | 0 | 11.085 | 10.385 | 8.003 | −1.674 |
| 2641 | 1.38 | 0 | 1.38 | 0 | 9.199 | 8.818 | 7.340 | 0.259 |
| 2642 | 3.67 | 0 | 3.67 | 0 | 10.731 | 8.777 | 7.167 | −0.458 |
| 2643 | 5.49 | 0 | 5.49 | 0 | 10.236 | 10.578 | 8.473 | −1.197 |
| 2645 | 0.19 | 0 | n/a | n/a | 11.130 | 9.997 | 8.254 | −1.129 |
| 2646 | 0.18 | 1 | 0.18 | 1 | 8.893 | 7.648 | 6.871 | 1.260 |
| 2648 | 0.25 | 0 | 0.25 | 0 | 8.855 | 7.745 | 7.060 | 1.303 |
| 2649 | 2.13 | 0 | 2.13 | 0 | 9.688 | 10.354 | 9.885 | 0.214 |
| 2650 | 2.43 | 0 | n/a | n/a | 10.007 | 10.052 | 8.861 | −0.305 |
| 2651 | 1.61 | 0 | n/a | n/a | 10.660 | 9.452 | 7.831 | −0.665 |

TABLE 3-continued

| Patient | Time to death or last follow up (years) | Status at last follow up (1 = dead, 0 = alive) | Time to death, progression, or last follow up (years) | Status at last follow up (1 = progressed or died, 0 = no progression) | Germinal Center Signature Average | Stromal-1 Signature Average | Stromal-2 Signature Average | Model Score |
|---|---|---|---|---|---|---|---|---|
| 2652 | 1.84 | 0 | 1.84 | 0 | 11.378 | 9.247 | 7.684 | −0.856 |
| 2653 | 1.88 | 0 | 1.88 | 0 | 11.182 | 9.638 | 7.781 | −1.106 |
| 2654 | 1.43 | 0 | 1.43 | 0 | 8.791 | 9.395 | 8.905 | 0.902 |
| 2813 | 3.97 | 0 | 3.97 | 0 | 10.701 | 9.366 | 8.258 | −0.306 |
| 2814 | 0.81 | 1 | 0.70 | 1 | 10.561 | 9.176 | 9.275 | 0.632 |

Figure 2C:
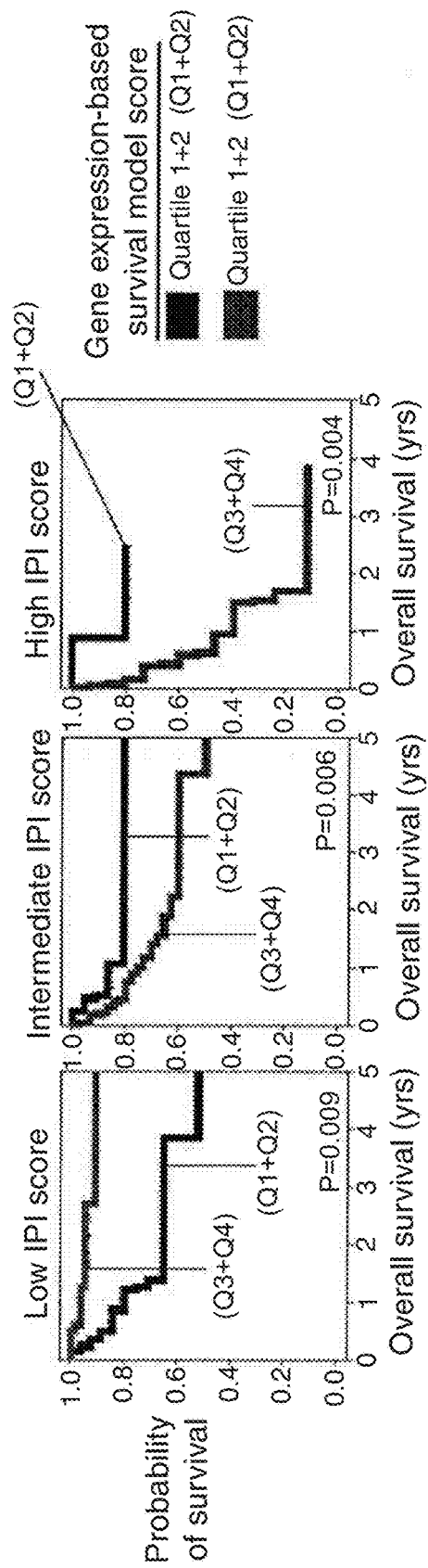
FIG. 2C is a series of three Kaplan-Meier estimates plots depicting the probability of overall survival versus time (in years) among R-CHOP treated DLBCL patients in the indicated low, intermediate, or high IPI risk groups. Patient samples were stratified according to the same survival predictor score used in FIG. 2B, except that the first and second quartiles were merged, and the third and fourth quartiles were merged.
Figure 10A:
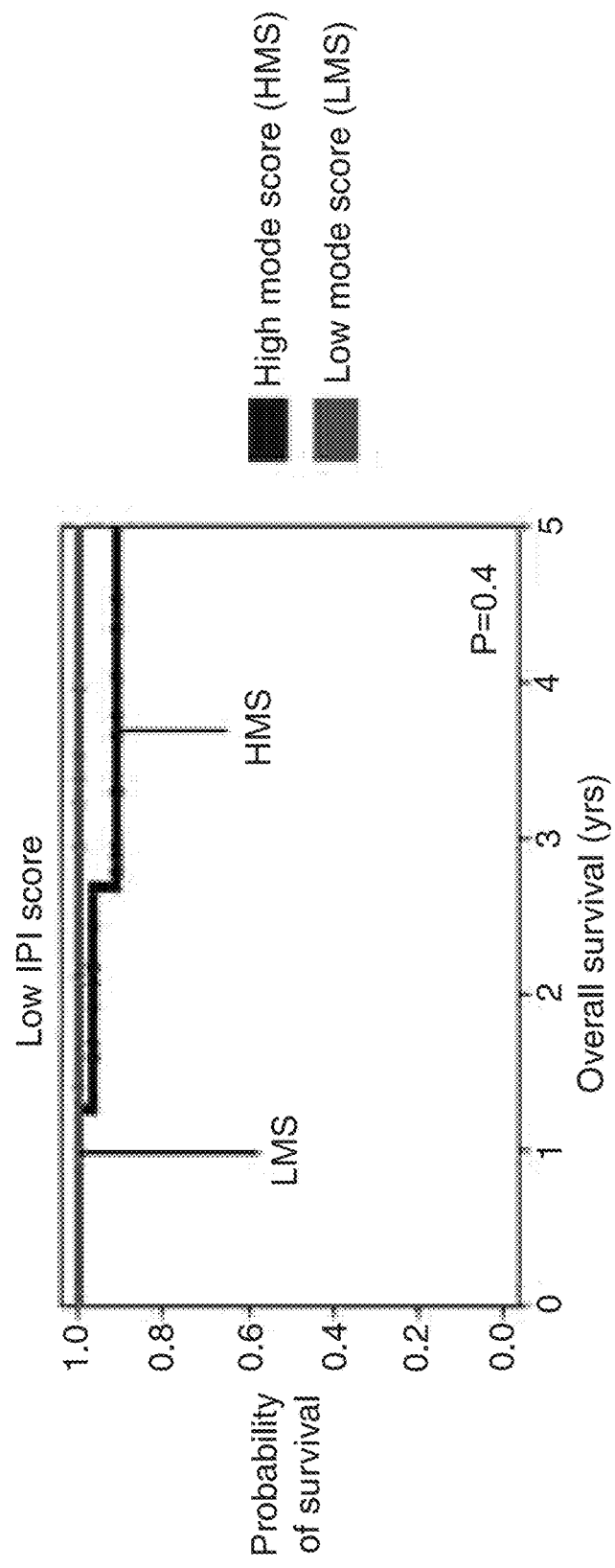
FIG. 10A is a Kaplan-Meier estimates plot depicting the overall survival among low revised International Prognostic Index (IPI) risk group patients stratified according to the gene expression-based outcome predictor score. After grouping patients into quartiles according to gene expression-based outcome predictor score, quartiles 1 and 2 were merged (Low Model Score), and quartiles 3 and 4 were merged (High Model Score).
Figure 10B:
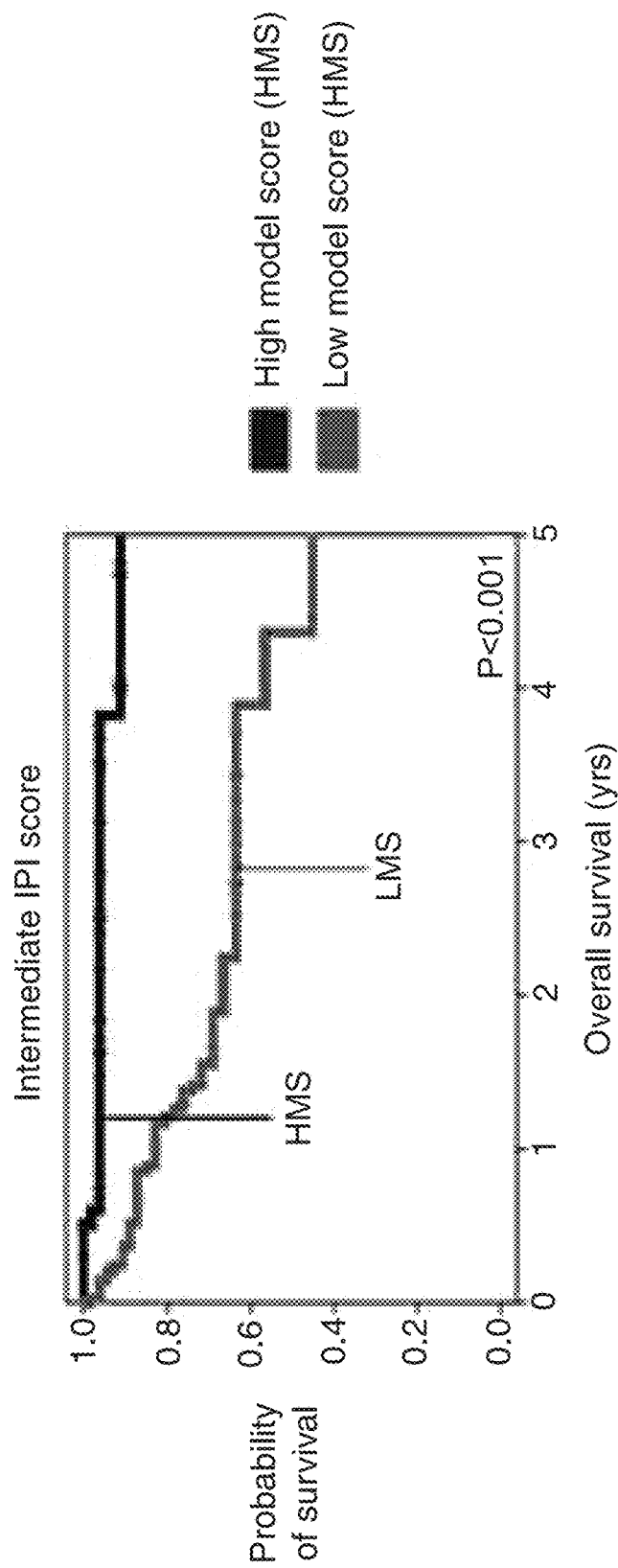
FIG. 10B is a Kaplan-Meier estimates plot depicting the overall survival among intermediate revised International Prognostic Index (IPI) risk group patients stratified according to the gene expression-based outcome predictor. After grouping patients into quartiles according to gene expression-based outcome predictor score, quartiles 1 and 2 were merged (Low Model Score), and quartiles 3 and 4 were merged (High Model Score).
Figure 10C:
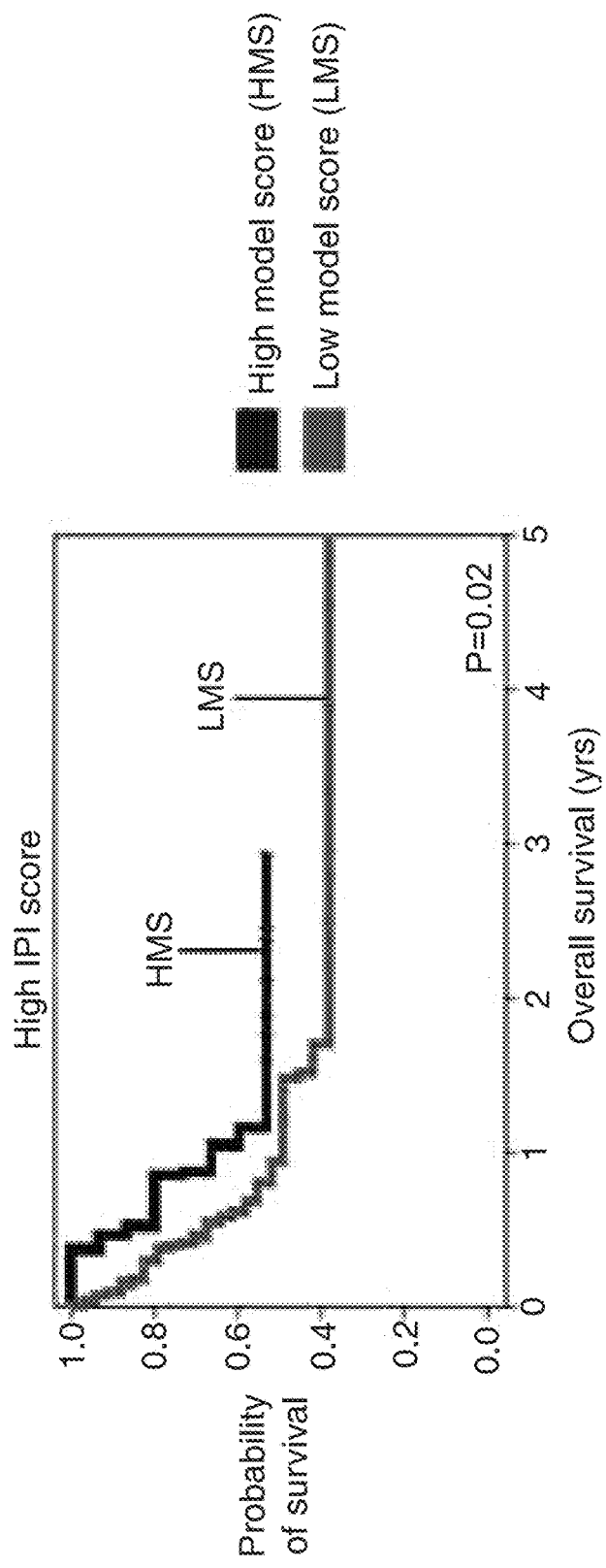
FIG. 10C is a Kaplan-Meier estimates plot depicting the overall survival among high revised International Prognostic Index (IPI) risk group patients stratified according to the gene expression-based outcome predictor. After grouping patients into quartiles according to gene expression-based outcome predictor score, quartiles 1 and 2 were merged (Low Model Score), and quartiles 3 and 4 were merged (High Model Score).

The International Prognostic Index (IPI), which is based on 5 clinical variables, predicts survival in both CHOP-treated and R-CHOP-treated patients (Shipp et al., *N. Engl. J. Med.*, 329:987-94 (1993); Sehn et al., *Blood*, 109: 1857-61 (2007)). The inventive gene expression-based survival model retained its prognostic significance among R-CHOP-treated patients segregated according to IPI into high, intermediate and low IPI risk groups, both as originally defined (Shipp et al., supra) (p<0.001) (FIG. 2C) and as recently modified for R-CHOP-treated DLBCL (Sehn et al., supra) (p<0.001) (FIG. 10).

The foregoing results indicate that the gene expression-based multivariate model can be used to identify large disparities in survival among patients with different DLBCL gene signature profiles. Thus, survival predictor scores were used to divide patients into least and most favorable quartile groups having 3-year progression-free survival rates of 33% and 84%, respectively. Given its statistical independence from the IPI, the gene expression-based survival predictor provides a complementary view of DLBCL variation that can be considered when analyzing data from DLBCL clinical trials. Additionally, the foregoing results indicate that whole-genome gene expression profiles in conjunction with the survival model described herein can be used to provide optimal predictions of expected survival outcomes for subjects suffering from DLBCL.

Example 3

This example demonstrates the use of a survival predictor score to predict the probability of progression free and overall survival outcomes at a period of time t following R-CHOP treatment in accordance with the invention.

RNA is isolated from a patient's DLBCL biopsy and hybridized to a U133+ array from Affymetrix (Santa Clara, Calif.). The array is scanned, and MAS 5.0 algorithm is applied to obtain signal values normalized to a target intensity of 500. Signal values are log 2 transformed to intensity values. For genes of interest with multiple probe sets, the intensity value of the multiple probe sets are averaged to obtain a single intensity value for each gene. The single intensity values of genes in the GCB signature are averaged to obtain a GCB signature average of 9.2. The single intensity values of genes in the stromal-1 signature are averaged to obtain a stromal-1 signature average of 8.5. The single intensity values of genes in the stromal-2 signature are averaged to obtain a stromal-2 signature average of 7.2.

The patient's survival predictor score is calculated using the following equation 8.11−[0.419*(GCB signature average)]−[1.015*(stromal-1 signature average)]+[0.675*(stromal-2 signature average)], such that the survival predictor score=8.11−[0.419*(9.2)]−[1.015*(8.5)]+[0.675*(7.2)]=0.389

Table 4 includes values from a progression free survival curve generated using baseline hazard functions calculated from the R-CHOP patient data described in Table 3. The curve was generated in accordance with the methods of Kalbfleisch and Prentice, *Biometrika*, 60: 267-279 (1973), which involves maximizing the full likelihood, under the assumption that the true scaling coefficients were equal to prior estimates. In Table 4, $F_0(t)$ is the probability of progression free survival for each indicated time period following R-CHOP treatment (t-RCHOP).

TABLE 4

| t-RCHOP (years) | $F_0(t)$ |
|---|---|
| 0.000 | 1.000 |
| 0.008 | 0.997 |
| 0.016 | 0.993 |
| 0.025 | 0.990 |
| 0.030 | 0.987 |
| 0.036 | 0.983 |
| 0.049 | 0.980 |
| 0.082 | 0.977 |
| 0.096 | 0.973 |
| 0.107 | 0.970 |
| 0.118 | 0.967 |
| 0.120 | 0.963 |
| 0.156 | 0.960 |
| 0.156 | 0.956 |
| 0.159 | 0.953 |
| 0.178 | 0.950 |
| 0.192 | 0.946 |
| 0.211 | 0.943 |
| 0.233 | 0.939 |
| 0.241 | 0.936 |
| 0.246 | 0.932 |
| 0.252 | 0.928 |
| 0.290 | 0.925 |
| 0.298 | 0.921 |
| 0.307 | 0.918 |
| 0.364 | 0.914 |
| 0.381 | 0.910 |
| 0.381 | 0.907 |
| 0.400 | 0.903 |
| 0.441 | 0.899 |
| 0.446 | 0.895 |
| 0.463 | 0.891 |
| 0.468 | 0.887 |
| 0.515 | 0.884 |
| 0.517 | 0.880 |
| 0.531 | 0.876 |
| 0.534 | 0.872 |
| 0.537 | 0.868 |
| 0.537 | 0.864 |
| 0.539 | 0.860 |
| 0.561 | 0.856 |
| 0.586 | 0.852 |
| 0.611 | 0.848 |
| 0.679 | 0.843 |
| 0.698 | 0.839 |
| 0.698 | 0.834 |
| 0.720 | 0.830 |
| 0.747 | 0.826 |
| 0.756 | 0.821 |

TABLE 4-continued

| t-RCHOP (years) | $F_0(t)$ |
|---|---|
| 0.761 | 0.816 |
| 0.767 | 0.812 |
| 0.786 | 0.807 |
| 0.849 | 0.803 |
| 0.879 | 0.798 |
| 0.884 | 0.793 |
| 0.898 | 0.789 |
| 0.912 | 0.784 |
| 0.977 | 0.779 |
| 0.986 | 0.774 |
| 1.046 | 0.770 |
| 1.057 | 0.765 |
| 1.076 | 0.760 |
| 1.128 | 0.755 |
| 1.166 | 0.750 |
| 1.216 | 0.745 |
| 1.227 | 0.740 |
| 1.270 | 0.735 |
| 1.481 | 0.729 |
| 1.547 | 0.724 |
| 1.624 | 0.718 |
| 1.900 | 0.711 |
| 1.919 | 0.705 |
| 2.105 | 0.699 |
| 2.231 | 0.692 |
| 2.245 | 0.685 |
| 2.352 | 0.678 |
| 2.546 | 0.671 |
| 2.968 | 0.662 |
| 3.890 | 0.648 |
| 4.364 | 0.623 |

The patient's probability of 2 year progression free survival is calculated using the equation: $P(PFS) = F_0(t)^{(exp(0.976*survival\ predictor\ score))}$, where $F_0(t)$ is the $F_0(t)$ value that corresponds to the largest time value smaller than 2 years in the progression free survival curve. In Table 4, the largest time value smaller than 2 is 1.919, and the corresponding $PF_0(t)$ value is 0.705. Accordingly, the patient's probability of 2 year progression free survival $P(PFS) = 0.705^{(exp(0.976*survival\ predictor\ score))} = 0.705^{1.462} = 0.600$ or about 60%.

Table 5 includes values from an overall survival curve generated using baseline hazard functions calculated from the R-CHOP patient data described in Table 3. The curve was made according to the method of Kalbfleisch and Prentice, *Biometrika*, 60: 267-279 (1973), which involves maximizing the full likelihood, under the assumption that the true scaling coefficients were equal to our estimates. In Table 5, $OS_0(t)$ is the probability of overall survival for each indicated time period following R-CHOP treatment (t-RCHOP).

TABLE 5

| t-RCHOP (years) | $OS_0(t)$ |
|---|---|
| 0.000 | 1.000 |
| 0.008 | 0.997 |
| 0.016 | 0.994 |
| 0.030 | 0.991 |
| 0.033 | 0.988 |
| 0.036 | 0.984 |
| 0.049 | 0.981 |
| 0.082 | 0.978 |
| 0.096 | 0.975 |
| 0.156 | 0.972 |
| 0.156 | 0.969 |
| 0.159 | 0.965 |
| 0.178 | 0.962 |
| 0.192 | 0.959 |
| 0.211 | 0.956 |
| 0.233 | 0.952 |
| 0.246 | 0.949 |
| 0.307 | 0.946 |
| 0.367 | 0.942 |
| 0.380 | 0.939 |
| 0.386 | 0.935 |
| 0.402 | 0.932 |
| 0.416 | 0.928 |
| 0.463 | 0.925 |
| 0.468 | 0.921 |
| 0.504 | 0.918 |
| 0.515 | 0.914 |
| 0.517 | 0.910 |
| 0.531 | 0.907 |
| 0.556 | 0.903 |
| 0.586 | 0.900 |
| 0.610 | 0.896 |
| 0.619 | 0.892 |
| 0.698 | 0.888 |
| 0.747 | 0.885 |
| 0.807 | 0.881 |
| 0.862 | 0.877 |
| 0.868 | 0.873 |
| 0.873 | 0.869 |
| 0.895 | 0.864 |
| 0.944 | 0.860 |
| 0.963 | 0.856 |
| 1.010 | 0.852 |
| 1.057 | 0.848 |
| 1.169 | 0.843 |
| 1.169 | 0.839 |
| 1.215 | 0.835 |
| 1.262 | 0.830 |
| 1.273 | 0.826 |
| 1.382 | 0.821 |
| 1.412 | 0.817 |
| 1.492 | 0.812 |
| 1.527 | 0.807 |
| 1.552 | 0.802 |
| 1.708 | 0.796 |
| 1.889 | 0.791 |
| 2.244 | 0.784 |
| 2.693 | 0.777 |
| 3.826 | 0.763 |
| 3.889 | 0.749 |
| 4.363 | 0.724 |

The patient's probability of 2 year overall survival is calculated using the equation: $P(OS) = OS_0(t)^{(exp(survival\ predictor\ score))}$, where $OS_0(t)$ is the value that corresponds to the largest time value in the overall survival curve which is smaller than 2 years. In Table 5, the largest time value smaller than 2 is 1.889, and the corresponding $OS_0(t)$ value is 0.791. Accordingly, the patient's probability of 2 year overall survival is $P(PFS) = 0.791^{(exp(0.389))} = 0.791^{1.4476} = 0.707$ or 70.7%.

Example 4

This example demonstrates the biological basis for DLBCL prognostic signatures.

Unless otherwise indicated, cohorts and methods of gene expression analysis are described in Examples 1 and 2. Furthermore, cell suspensions from three biopsies were separated by flow cytometry into a CD19+ malignant subpopulation and a CD19− non-malignant subpopulation. Gene expression profiling was performed following two rounds of linear amplification from total RNA (Dave et al., *N. Engl. J. Med.*, 351: 2159-69 (2004)). After MAS5.0 normalization, genes were selected that had a log 2 signal value greater than 7 in either the CD19+ or CD19− fractions in at least two of the sorted samples.

Figure 4A:
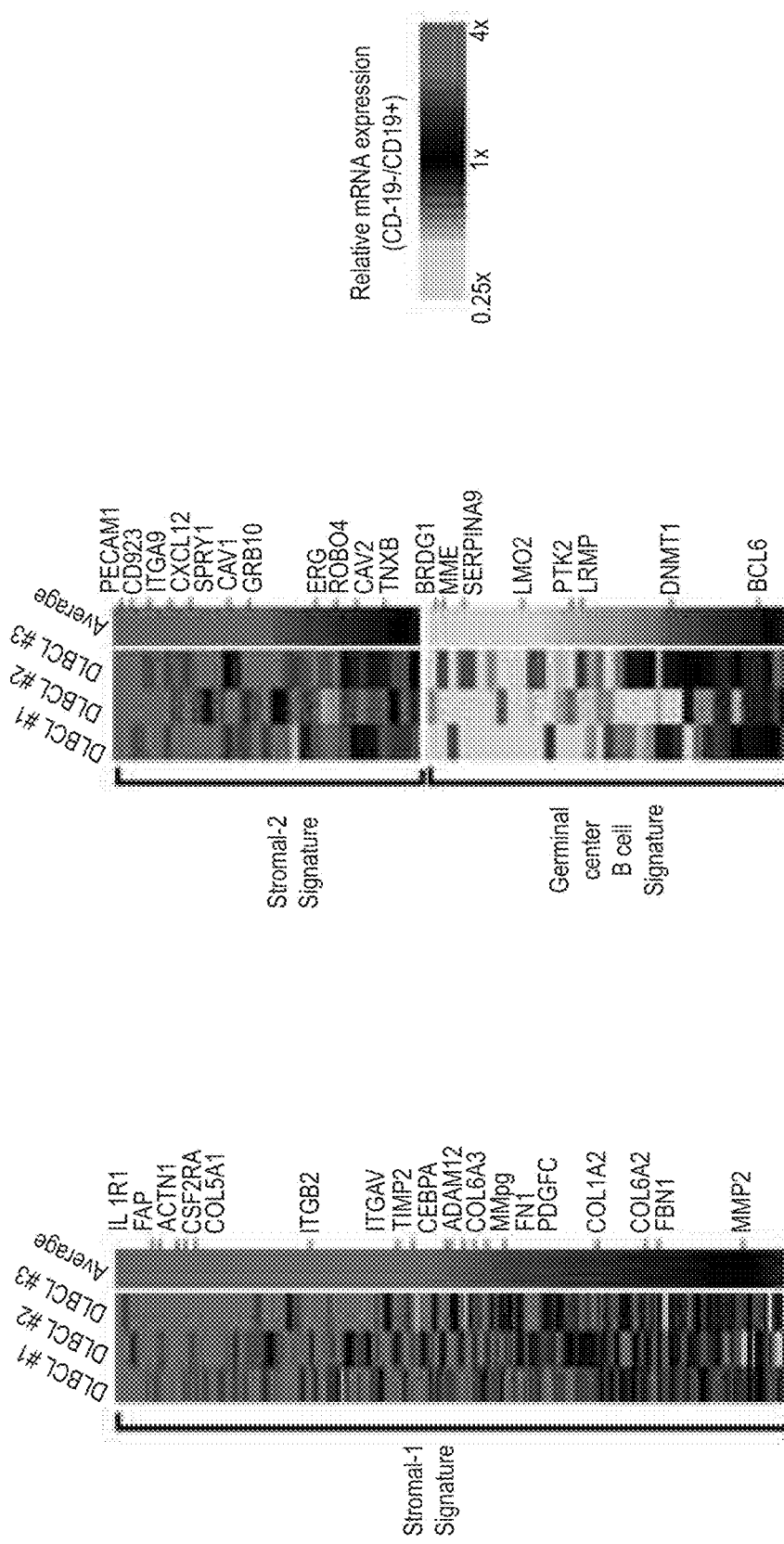
FIG. 4A depicts the relative gene expression of stromal-1, stromal-2, and germinal center B cell signatures in CD19+ malignant and CD19– non-malignant subpopulations of cells isolated from three biopsy specimens from patients with DLBCL. Stromal-1 and stromal-2 signature genes were more highly expressed in the non-malignant cells, whereas the germinal center B cell signature genes were more highly expressed in the malignant cells. The log 2 ratios of gene expression levels in the CD19– subpopulation to those in the CD19+ subpopulations are depicted according to the scale shown.

To assess whether the gene expression signatures in the final survival model of Example 2 were derived from the malignant lymphoma cells or from the host microenvironment, three DLBCL biopsy samples were fractionated into CD19+ malignant cells and CD19− non-malignant cells by flow sorting. Most germinal center B cell signature genes were more highly expressed in the malignant fraction, whereas genes from the stromal-1 and stromal-2 signatures were more highly expressed in the non-malignant stromal fraction (FIG. 4A), hence their name. Since these two signatures were synergistic in predicting survival, they were combined into a "stromal score" (FIG. 3), high values of which were associated with adverse outcome.

The germinal center B cell signature relates to the distinction between the ABC and GCB DLBCL subtypes (FIG. 3). By contrast, the genes defining the stromal-1 signature encodes components of the extracellular matrix, including fibronectin, osteonectin, various collagen and laminin isoforms, and the anti-angiogenic factor thrombospondin (FIG. 3 and Table 1). This signature also encodes modifiers of collagen synthesis (LOXL1, SERPINH1), proteins that remodel the extracellular matrix (MMP2, MMP9, MMP14, PLAU, TIMP2), and CTGF, a secreted protein that can initiate fibrotic responses (Frazier et al., *J. Invest. Dermatol.*, 107(3): 404-11 (1996)). In addition, the stromal-1 signature includes genes characteristically expressed in cells of the monocytic lineage, such as CEBPA and CSF2RA.

Figure 4B:
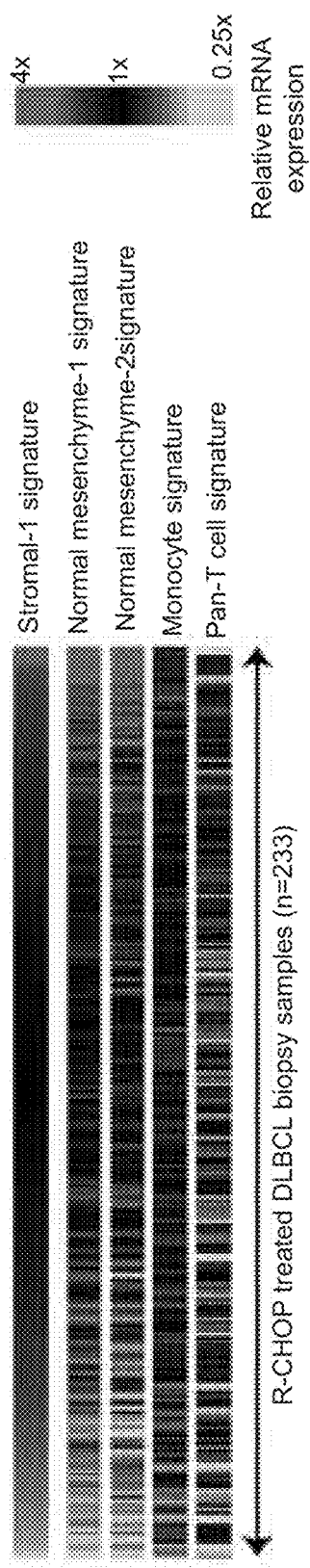
FIG. 4B depicts the results of gene enrichment analysis comparing the stromal-1 gene signature with mesenchyme-1 and mesenchyme-2 signatures (from normal mesenchymal origin cells), with a monocyte signature expressed more highly in normal blood monocytes than in blood B, T, and NK cells, and in a pan-T cell signature expressed more highly in blood T cells than in blood B cells, NK cells, and monocytes. While a relationship was seen between stromal-1 signature and mesenchyme-1, mesenchyme-2, and monocyte signatures, no relationship was observed between the stromal-1 signature and a pan-T cell signature expressed more highly in blood T cells than in blood B cells, NK cells, and monocytes. The relative levels of gene expression are depicted according to the scale shown.
Figure 11:
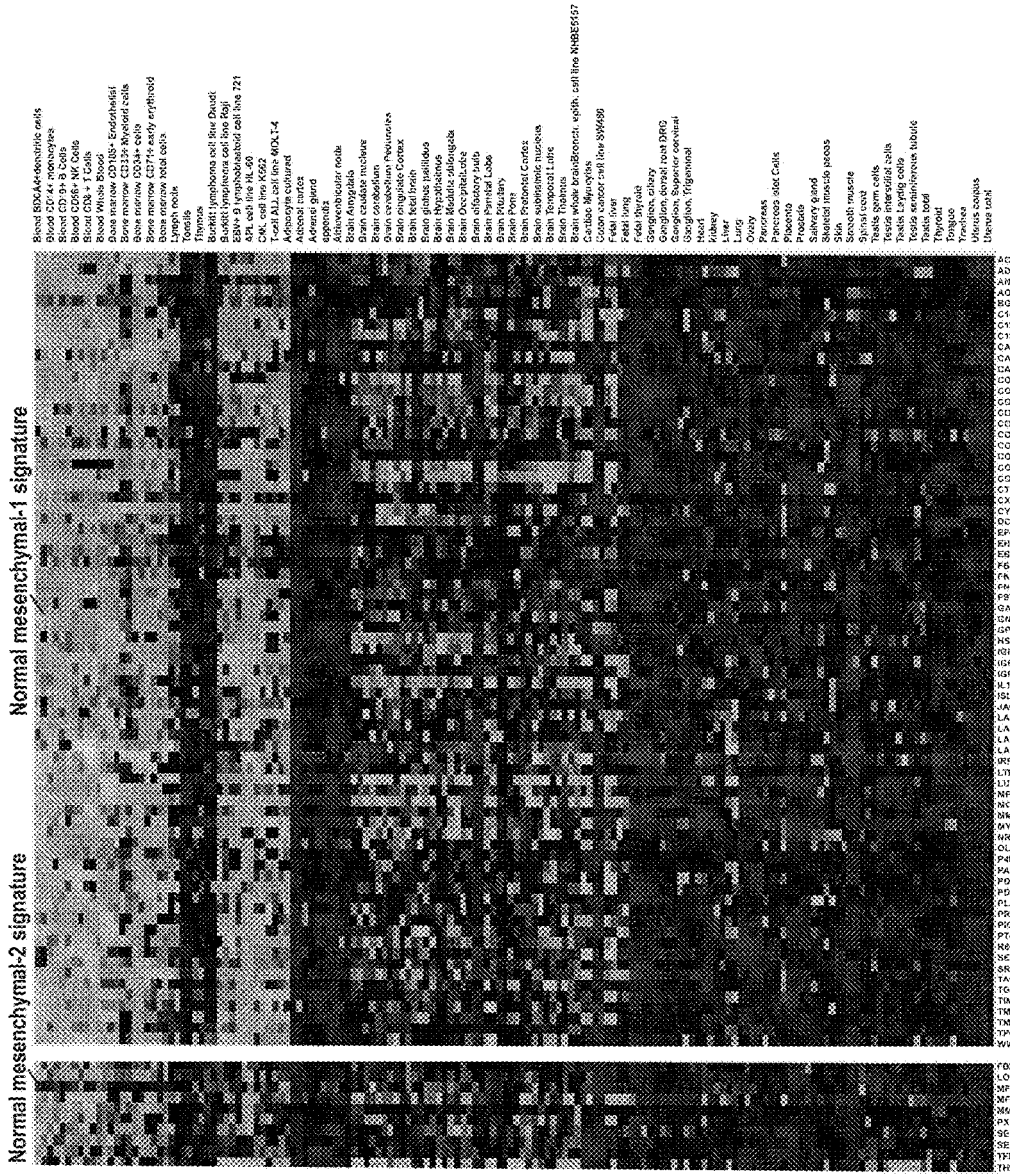
FIG. 11 depicts normal mesenchymal-1 and normal mesenchymal-2 signature gene expression in various normal tissues.

The stromal-1 signature is significantly related to several previously curated gene expression signatures (Shaffer et al., *Immunol. Rev.*, 210: 67-85 (2006)) based on gene set enrichment analysis (Subramanian et al., *Proc. Nat'l. Acad. Sci. USA*, 102(43): 15545-50 (2005)). Two of these signatures include genes that are coordinately expressed in normal mesenchymal tissues but not in hematopoietic subsets, many of which encode extracellular matrix proteins (false discovery rate (FDR)<0.001) (FIGS. 4B and 11) (Su et al., *Proc. Nat'l. Acad. Sci. USA*, 101: 6062-7 (2004)). Also enriched was a "monocyte" signature, comprised of genes that are more highly expressed in CD14+ blood monocytes than in B cells, T cells, or NK cells (FDR=0.014) (FIG. 4B). By contrast, a pan-T cell signature was not related to the stromal-1 signature (FIG. 4B). These findings suggest that high expression of the stromal-1 signature identifies tumors with vigorous extracellular matrix deposition and infiltration by cells in the monocytic lineage.

Figure 5A:
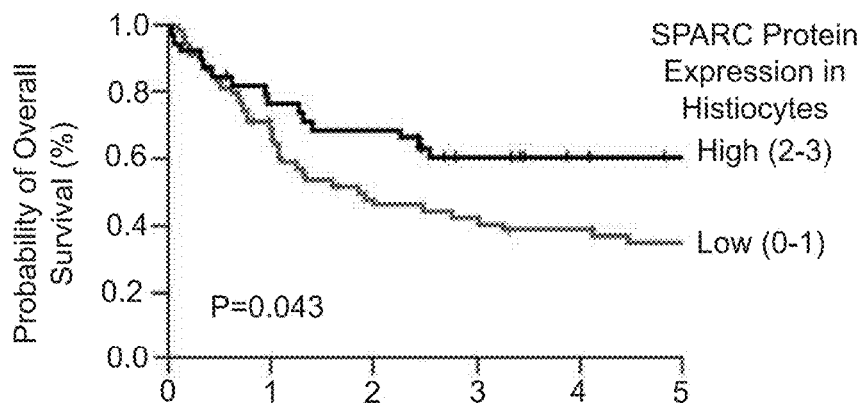
FIG. 5A is a Kaplan-Meier estimates plot depicting the probability of overall survival versus time (in years) in DLBCL cases segregated according to SPARC protein expression levels, as indicated.

In this regard, the stromal-1 signature gene product fibronectin was prominently localized by immunohistochemistry to fibrous strands running between the malignant cells in DLBCL biopsy samples, in keeping with its role in extracellular matrix formation. By contrast, the protein products of three other stromal-1 genes—MMP9, SPARC, and CTGF—were localized primarily in histiocytic cells that infiltrated the DLBCL biopsies. By immunofluorescence, SPARC and CTGF colocalized with CD68, which is a marker for cells in the monocytic lineage. As expected for a stromal-1 gene product, SPARC protein levels were associated with favorable overall survival (FIG. 5A).

The stromal-1 signature includes genes that are coordinately expressed in many normal mesenchymal tissues, most of which encode proteins that form or modify the extracellular matrix. The localization of fibronectin to fibrous strands insinuated between the malignant lymphoma cells suggests that the stromal-1 signature reflects the fibrotic nature of many DLBCL tumors. This fibrotic reaction may be related to another stromal-1 signature component, CTGF, which participates in many fibrotic responses and diseases, and promotes tumor growth and metastasis of epithelial cancers (Shi-Wen et al., *Cytokine Growth Factor Rev.*, 19: 133-44 (2008)).

The foregoing results also indicate that the stromal-1 signature reflects a monocyte-rich host reaction to the lymphoma that is associated with the abundant deposition of extracellular matrix. Tumors with high expression of the stromal-1 signature were infiltrated by cells of the myeloid lineage, which include cells that have been implicated in the pathogenesis of epithelial cancers, including tumor-associated macrophages, myeloid-derived suppressor cells, and Tie2-expressing monocytes (reviewed in Wels et al., *Genes Dev.*, 22: 559-74 (2008)). In animal models, these myeloid lineage cells promote tumor cell invasion by secreting matrix metalloproteinases such as MMP9, suppress T cell immune responses, and initiate angiogenesis.

Several stromal-2 signature genes encode well-known markers of endothelial cells. These include von-Willebrand factor (VWF) and CD31 (PECAM1), as well as other genes specifically expressed in endothelium such as EGFL7, MMRN2, GPR116, and SPARCL (Table 1). This signature also includes genes encoding key regulators of angiogenesis, such as, for example, KDR (VEGF receptor-2); Grb10, which mediates KDR signaling; integrin alpha 9, which enhances VEGF signaling; TEK, the receptor tyrosine kinase for the cytokine angiopoietin; ROBO4, an endothelial-specific molecular guidance molecule that regulates angiogenesis; and ERG, a transcription factor required for endothelial tube formation. The stromal-2 signature genes CAV1, CAV2, and EHD2 encode components of caveolae, which are specialized plasma membrane structures that are abundant in endothelial cells and required for angiogenesis (Frank et al., *Arterioscler. Thromb. Vasc. Biol.*, 23: 1161-8 (2003); Woodman et al., *Am. J. Pathol.*, 162: 2059-68 (2003)). Although the stromal-2 signature includes a large number of genes expressed in endothelial cells, other genes are expressed exclusively in adipocytes, including ADIPOQ, FABP4, RBP4, and PLIN.

Figure 5B:
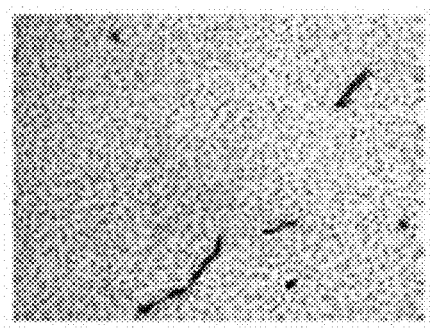
FIG. 5B is a pair of images showing the identification of tumor blood vessels by immunohistochemical analysis of CD34+ endothelial cells in representative DLBCL biopsies having low or high blood vessel density (CD34+ objects/$\mu M^2$), as indicated.
Figure 5B:
Figure 5C:
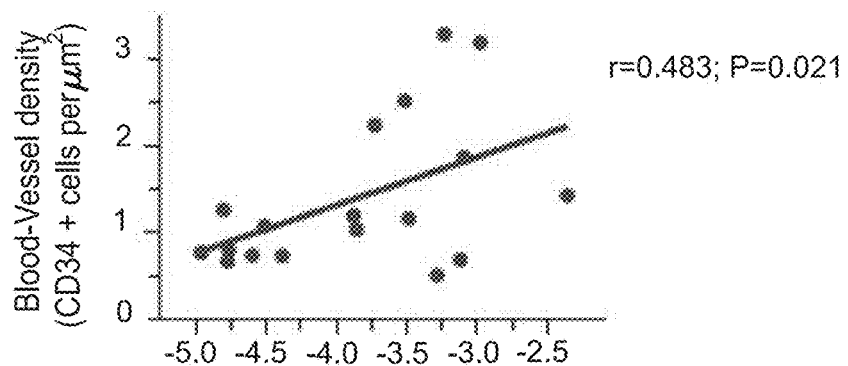
FIG. 5C is a plot depicting the correlation between the tumor blood vessel density and the stromal score in analyzed DLBCL biopsies.

Quantitative tests were done to determine whether expression of the stromal-2 signature relative to the stromal-1 signature (i.e., high stromal score) is related to high tumor blood vessel density, given the connection between many stromal-2 signature genes and angiogenesis. More specifically, the stromal-1 signature averages were subtracted from the stromal-2 signature average to thereby obtain a stromal score for each biopsy. Tests showed a quantitative measure of blood vessel density correlated significantly with the stromal score (r=0.483, p=0.019) (see FIGS. 5B and 5C), such that higher blood vessel densities correlated with higher stromal scores.

Thus, the stromal-1 and stromal-2 gene expression signatures reflect the character of the non-malignant cells in DLBCL tumors, and the stromal-2 signature may represent an "angiogenic switch" in which the progression of a hyperplastic lesion to a fully malignant tumor is accompanied by new blood vessel formation (Hanahan et al., *Cell*, 86: 353-64 (1996)). DLBCL tumors with high relative expression of the stromal-2 signature were associated with increased tumor blood vessel density and adverse survival. Significant macrophage infiltration in some DLBCL tumors may predispose to angiogenesis since, in experimental models, tumor-associated macrophages accumulate prior to the angiogenic switch and are required for the switch to occur (Lin et al., *Cancer Res.*, 66: 11238-46 (2006)). Additionally, CXCL12 (SDF-1), a stromal-2 signature component, is a chemokine secreted either by fibroblasts or endothelial cells that can promote angiogenesis by recruiting CXCR4+ endothelial precursor cells from the bone marrow (Orimo et al., *Cell,* 121: 335-48 (2005)). Moreover, an antagonist of angiogenesis, thrombospondin-2 (Kazerounian et al., *Cell Mol. Life Sci.,* 65: 700-12 (2008)), is a stromal-1 signature component, which may explain why tumors with low relative expression of this signature had an elevated blood vessel density. Furthermore, the expression of adipocyte-associated genes in DLBCL tumors with high stromal-2 signature expression may play a role in angiogenesis since some cells in adipose tissue may have the potential to differentiate into endothelial cells (Planat-Benard et al., *Circulation,* 109: 656-63 (2004)). Alternatively, the expression of adipose-associated genes may reflect the recruitment of bone marrow-derived mesenchymal stem cells, which home efficiently to tumors (Karnoub et al., *Nature,* 449: 557-63 (2007)) and can stabilize newly formed blood vessels (Au et al., *Blood,* 111: 4551-4558 (2008)).

The foregoing results indicate that the stromal-1 and stromal-2 gene signatures can be used to generate a stromal score that correlates with increased blood vessel density. Thus, the stromal score can be used to determine if a DLBCL patient is likely to benefit from administration of antiangiogenic therapy (alone, or in conjunction with another DLBCL therapeutic regimen).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09970059B2). An electronic copy of the "Sequence Listing" will also be available from the USPTO upon request and payment of the fee set forth in 37 CFR 1.19(b)(3).

The invention claimed is:

1. A method of treating a subject suffering from diffuse large B cell lymphoma (DLBCL), the method comprising:
    (1) predicting the survival outcome of the subject comprising:
        a) obtaining one or more DLBCL biopsy samples from a subject;
        b) isolating gene expression product from the one or more DLBCL biopsy samples;
        c) obtaining a gene expression profile from the gene expression product by detecting an expression level for each gene in a germinal center B cell (GCB) gene expression signature and a stromal-1 gene expression signature and a stromal-2 gene expression signature;
        d) determining a GCB signature value and a stromal-1 signature value and a stromal-2 gene signature value from the gene expression profile, and
        e) calculating a survival predictor score using the equation: survival predictor score=8.11−[0.419*(the GCB signature value)]−[1.015*(the stromal-1 signature value)]+[0.675*(the stromal-2 signature value)],
    wherein a lower survival predictor score indicates a more favorable survival outcome and a higher survival predictor score indicates a less favorable survival outcome for the subject; and
    (2) treating the subject with chemotherapy and Rituximab.

2. The method of claim 1, wherein the GCB signature value corresponds to the average of the expression levels of the genes in the GCB gene expression signature, the stromal-1 signature value corresponds to the average of the expression levels of the genes in the stromal-1 gene expression signature, and the stromal-2 signature value corresponds to the average of the expression levels of the genes in the stromal-2 gene expression signature.

3. The method of claim 1, wherein the one or more DLBCL samples are obtained from a subject designated for treatment with chemotherapy and Rituximab.

4. The method of claim 1, further comprising: (1)
f) tracking a survival outcome for the subject following treatment for DLBCL; and
g) generating a survival estimate curve that correlates the probability of the tracked survival outcome with time following treatment for DLBCL, wherein the survival curve also correlates tracked outcome over time with the survival predictor score for the subject.

5. The method of claim 4, wherein the survival outcome is overall survival.

6. The method of claim 4, wherein the survival outcome is progression free survival.

7. The method of claim 4, wherein the GCB signature value corresponds to the average of the expression levels of the genes in the GCB gene expression signature, the stromal-1 signature value corresponds to the average of the expression levels of the genes in the stromal-1 gene expression signature, and the stromal-2 signature value corresponds to the average of the expression levels of the genes in the stromal-2 gene expression signature.

8. The method of claim 1, further comprising: (1)
f) calculating the probability of a survival outcome for the subject beyond an amount of time t following treatment for DLBCL, wherein the subject's probability of the survival outcome P(SO) is calculated using the equation: P(SO)=SO0(t)(exp((s)*survival predictor score)), wherein SO0(t) is the probability of the survival outcome, which corresponds to the largest time value smaller than t in a survival outcome curve, and wherein (s) is a scale factor.

9. The method of claim 1, further comprising: (1)
f) calculating the probability of overall survival after time t for the subject, wherein the subject's probability of overall survival P(OS) is calculated using the equation: P(OS)=OS0(t)(exp(survival predictor score)), wherein OS0(t) is the probability of overall survival, which corresponds to the largest time value smaller than t in an overall survival curve.

10. The method of claim 1, further comprising: (1)
f) calculating the probability of progression free survival after time t for the subject, wherein the subject's probability of progression free survival P(PFS) is calculated using the equation P(PFS)=F0(t)(exp(0.976*survival predictor score)), wherein F0(t) is the probability of progression free survival, which corresponds to the largest time smaller than t in a survival curve.

11. The method of claim 8, wherein the GCB signature value corresponds to the average of the expression levels of the genes in the GCB gene expression signature, the stromal-1 signature value corresponds to the average of the expression levels of the genes in the stromal-1 gene expression signature, and the stromal-2 signature value corresponds to the average of the expression levels of the genes in the stromal-2 gene expression signature.

12. The method of claim 8, wherein the method further includes providing the subject with the calculated probability of the survival outcome after time t.

13. A method of treating a subject suffering from diffuse large B cell lymphoma (DLBCL), the method comprising:
(1) selecting the subject for antiangiogenic therapy of DLBCL comprising:
a) isolating gene expression product from one or more DLBCL biopsy samples from a subject;
b) obtaining a gene expression profile from the gene expression product by detecting an expression level for each gene in a stromal-1 signature and a stromal-2 signature;
c) determining the subject's stromal-1 signature value and stromal-2 signature value from the gene expression profile;
d) subtracting the stromal-1 signature value from the stromal-2 signature value to thereby obtain the subject's stromal score;
e) determining whether the subject's stromal score is higher or lower than a standard stromal score; wherein antiangiogenic therapy is indicated by a stromal score that is higher than a standard stromal score and antiangiogenic therapy is not indicated by a stromal score that is not higher than a standard stromal score; and
f) determining that the subject's stromal score that is higher than the standard stromal score; and
(2) treating the subject with antiangiogenic therapy.

14. The method of claim 13, wherein the stromal-1 signature value corresponds to the average of the expression levels of the genes in the stromal-1 gene expression signature and the stromal-2 signature value corresponds to the average of the expression levels of the genes in the stromal-2 gene expression signature.

15. The method of claim 9, wherein the GCB signature value corresponds to the average of the expression levels of the genes in the GCB gene expression signature, the stromal-1 signature value corresponds to the average of the expression levels of the genes in the stromal-1 gene expression signature, and the stromal-2 signature value corresponds to the average of the expression levels of the genes in the stromal-2 gene expression signature.

16. The method of claim 10, wherein the GCB signature value corresponds to the average of the expression levels of the genes in the GCB gene expression signature, the stromal-1 signature value corresponds to the average of the expression levels of the genes in the stromal-1 gene expression signature, and the stromal-2 signature value corresponds to the average of the expression levels of the genes in the stromal-2 gene expression signature.

* * * * *